(12) United States Patent
Emerick et al.

(10) Patent No.: US 10,227,584 B2
(45) Date of Patent: Mar. 12, 2019

(54) METHODS OF SEQUENCING NUCLEIC ACIDS IN MIXTURES AND COMPOSITIONS RELATED THERETO

(71) Applicants: Emory University, Atlanta, GA (US); The Johns Hopkins University, Baltimore, MD (US)

(72) Inventors: Mark C. Emerick, Columbia, MD (US); William S. Agnew, Atlanta, GA (US)

(73) Assignees: Emory University, Atlanta, GA (US); The Johns Hopkins University, Baltimore, MD (US)

( * ) Notice: Subject to any disclaimer, the term of this patent is extended or adjusted under 35 U.S.C. 154(b) by 147 days.

(21) Appl. No.: 14/768,749

(22) PCT Filed: Feb. 17, 2014

(86) PCT No.: PCT/US2014/016673
§ 371 (c)(1),
(2) Date: Aug. 18, 2015

(87) PCT Pub. No.: WO2014/130388
PCT Pub. Date: Aug. 28, 2014

(65) Prior Publication Data
US 2016/0046930 A1    Feb. 18, 2016

Related U.S. Application Data

(60) Provisional application No. 61/766,841, filed on Feb. 20, 2013.

(51) Int. Cl.
| | | |
|---|---|---|
| *C12Q 1/68* | (2018.01) | |
| *C07H 21/00* | (2006.01) | |
| *C12N 15/10* | (2006.01) | |
| *C12Q 1/6869* | (2018.01) | |

(52) U.S. Cl.
CPC ....... *C12N 15/1065* (2013.01); *C12Q 1/6869* (2013.01)

(58) Field of Classification Search
CPC ............ C12Q 1/68; C07H 21/00; C12P 19/34
See application file for complete search history.

(56) References Cited

U.S. PATENT DOCUMENTS

| | | | | |
|---|---|---|---|---|
| 5,424,413 A * | 6/1995 | Hogan | ............... | C12N 15/1068 435/6.1 |
| 5,605,793 A * | 2/1997 | Stemmer | .......... | C07K 14/43595 435/6.11 |
| 6,235,502 B1 * | 5/2001 | Weissman | ............ | C12Q 1/6827 435/6.1 |
| 6,350,595 B1 * | 2/2002 | Neuner | .................. | C07H 21/00 435/6.1 |
| 7,655,791 B2 | 2/2010 | Makarov et al. | | |
| 2001/0053519 A1 * | 12/2001 | Fodor | .................. | B01J 19/0046 435/6.11 |
| 2004/0180372 A1 * | 9/2004 | Nelson | ................. | C12Q 1/6862 435/6.12 |
| 2007/0031857 A1 * | 2/2007 | Makarov | ................. | C12P 19/34 435/6.18 |
| 2009/0298156 A1 * | 12/2009 | Black | ................... | C12N 9/1211 435/194 |
| 2010/0069263 A1 | 3/2010 | Shendure et al. | | |
| 2010/0330574 A1 | 12/2010 | Whitman et al. | | |
| 2011/0015096 A1 * | 1/2011 | Chiu | ................... | C12N 15/1093 506/16 |
| 2011/0092375 A1 * | 4/2011 | Zamore | ............. | C12N 15/1031 506/7 |
| 2011/0189677 A1 | 8/2011 | Adli et al. | | |
| 2012/0238457 A1 * | 9/2012 | Seitz | .................... | C12Q 1/6809 506/4 |
| 2012/0283145 A1 | 11/2012 | Wang | | |
| 2012/0309650 A1 | 12/2012 | Patel et al. | | |
| 2013/0261027 A1 * | 10/2013 | Li | ........................ | C12Q 1/6806 506/26 |
| 2013/0288244 A1 * | 10/2013 | Deciu | .................... | C12Q 1/683 435/6.11 |
| 2014/0155274 A1 * | 6/2014 | Xie | ....................... | C12Q 1/6853 506/2 |
| 2014/0213485 A1 * | 7/2014 | Weissman | .......... | C12N 15/1093 506/26 |

(Continued)

FOREIGN PATENT DOCUMENTS

| | | |
|---|---|---|
| DE | 10 2008 025 656 A1 | 12/2009 |
| JP | 2006-516410 | 7/2006 |

(Continued)

OTHER PUBLICATIONS

Bentley et al.,Accurate whole human genome sequencing using reversible terminator chemistry. Nature 456:53 (2008).*
Craig et al., Identification of genetic variants using bar-coded multiplexed sequencing. Nature Methods 5(10): 887(2008).*
Frank, DBARCRAWL and BARTAB: software tools for the design and implementation of barcoded primers for highly multiplexed DNA sequencing. BMC Bioinformatics 10 :362 (2009).*
Fullwood et al., Next-generation DNA sequencing of paired-end tags (PET) for transcriptome and genome analyses. Genome Research 19:521(2009).*
Haas et al.,Advancing RNA-Seq analysis. Nature Biotechnology 28(5):421 (May 2010).*

(Continued)

*Primary Examiner* — Ethan C Whisenant
(74) *Attorney, Agent, or Firm* — Klarquist Sparkman, LLP

(57) ABSTRACT

This disclosure relates to analyzing the end-to-end sequence and the relative distributions in heterogeneous mixtures of polynucleotides and methods and enabling reagents related thereto. In certain embodiments this method relates to the complete full length sequencing and quantitative profiling of mRNAs present in the transcriptomes of cells or tissues of but not limited to, higher multicellular organisms that possess interrupted genes subject to complex post-transcriptional RNA processing.

7 Claims, 27 Drawing Sheets

Specification includes a Sequence Listing.

(56) References Cited

U.S. PATENT DOCUMENTS

| | | | |
|---|---|---|---|
| 2015/0099671 A1* | 4/2015 | Moore | C12N 15/1096 506/26 |
| 2017/0058342 A1* | 3/2017 | Welsh | C12Q 1/6832 |
| 2017/0088832 A1* | 3/2017 | McEwan | C12Q 1/6806 |
| 2017/0088893 A1* | 3/2017 | Li | C12Q 1/6876 |
| 2017/0137806 A1* | 5/2017 | Jaitin | C12N 15/1065 |
| 2017/0253876 A1* | 9/2017 | Eberwine | C12N 15/113 |

FOREIGN PATENT DOCUMENTS

| | | |
|---|---|---|
| JP | 2008-253219 | 10/2008 |
| JP | 2008-545448 | 12/2008 |
| JP | 2012-080807 | 4/2012 |
| WO | WO 2004/070053 | 8/2004 |
| WO | WO 2007/145612 | 12/2007 |
| WO | WO 2010/097528 A1 | 8/2011 |
| WO | WO 2013/096802 A1 | 6/2013 |
| WO | WO 2014/071361 A1 | 5/2014 |

OTHER PUBLICATIONS

Halbritter et al., High-throughput mutation analysis in patients with a nephronophthisis-associated ciliopathy applying multiplexed barcoded array-based PCR amplification and next-generation sequencing. Journal of Medical Genetics 49: 756 (2012).*

Kozich et al., Development of a Dual-Index Sequencing Strategy and Curation Pipeline for Analyzing Amplicon Sequence Data on the MiSeq Illumina Sequencing Platform. Applied and Environmental Microbiology 79 (17) :5112 (Sep. 2013).*

Maekawa et al., Chapter 6: RNA Sequencing: From Sample Preparation to Analysis. Methods in Molecular Biology 1164 :51 (May 2014).*

Mamanova et al., Target-enrichment strategies for next generation sequencing. Nature Methods 7(2): 111 (Feb. 2010).*

Margulies et al., Genome Sequencing in Microfabricated High Density Picoliter Reactors. Nature 437(7057): 376 (2005).*

Metzker,M. L., Sequencing technologies—the next generation. Nature Reviews | Genetics 11:31 (Jan. 2010).*

Meyer et al., Illumina Sequencing Library Preparation for Highly Multiplexed Target Capture and Sequencing. Cold Spring Harbor Protoc. 2010 (6): 1.*

Nagalakshmi et al., The Transcriptional Landscape of the Yeast Genome Defined by RNA Sequencing. Science 320:1344 (Jun. 2008).*

Pan et al.,Two methods for full-length RNA sequencing for low quantities of cells and single cells. PNAS 110(2):594 (Jan. 2013).*

Parameswaran et al., A pyrosequencing-tailored nucleotide barcode design unveils opportunities for large-scale sample multiplexing. Nucleic Acids Research 35 (19): e130 (2007).*

Sharon et al., A single-molecule long-read survey of the human transcriptome. Nature Biotechnology 31(11): 1009 (Nov. 2013).*

Shendure et al.,Next-generation DNA sequencing. Nature Biotechnology 26(10): 1135 (Oct. 2008).*

Tang et al.,mRNA-Seq whole-transcriptome analysis of a single cell. Nature Methods 6(5) :317 (May 2009).*

Thelwell et al., Mode of action and application of Scorpion primers to mutation detection. Nucleic Acids Research 28 (19): 3752 (2000).*

Wang et al. RNA-Seq: a revolutionary tool for transcriptomics. 10 (1): 57 (Jan. 2009).*

Whitcombe et al., Detection of PCR products using selfprobing amplicons and fluorescence. Nature Biotechnology 17: 804 (Aug. 1999).*

International Search Report from parent PCT Application No. PCT/US2014/016673, four pages (dated May 22, 2014).

Yohda, "Principle and application of next generation sequencer," *Kagaku to Seibutsu, Chemistry and Biology* 47(3): 185-192 (in Japanese, with English translation), (2009).

Japanese Office Action issued in corresponding Japanese Patent Application No. 2015-558897, (in Japanese, with English language translation), dated Mar. 13, 2018.

* cited by examiner

Self-complementarity of type II marker blocks

Conformation of Tagging Reagent

| Tag Type | Tagging Reagent | |
|---|---|---|
| | one tailed | two tailed |
| I | | |
| II-ps | | |
| II-pa | | |
| II-t | | |

(a)

(b)

End-tagged read I (5' ends of library fragments) 100 bases

CAATANNNNANNNCNNNGNNNTNNNANNNGCGGCCGCAG – Marker Motif: 5' wrapper-SMID-3' wrapper

```
01 CAATAAAAGGACCTAGATATAACAGCTGCGGCCGCAGAGGTGGATATCTTGACCTACGTGGCTTGGAAGATAAGTGGTTTTCCCAAAAAACCGTGTTAT
02 CAATAAATATTTCATCGTTCTGATACGAGCGGCCGCAGAGGTGGATATCTTGACCTACGTGGCTTGGAAGATAAGTCCTTTTCCCAAAAAACCGTGTTAT
03 CAATAACCACGGCAGTGTGGTCTGACTAGCGGCCGCAGGGGTGGTGGGATGATTATTGTAATCATACTTGGGAACAGAAGTGATGAAAAAGGTATGTTAC
04 CAATAACAATGTCTTTGCGGTCTTATTTGCGGCCGCAGCTGGCAAGATCGGAAGAGCGGTTCAGCAAGAATGCCGAGACCGATCTCGGATGCCGGCTTCT
05 CAATACGAATGGCTTTGGTCTTGTATATGCGGCCGCAGCCCCTGAATCTCTACTTTTTTTTCTCTCATATAGATCGGAAGAGCGGTTCAGCAGGAATGCC
06 CAATACCAAGATGGCGTTATTCCACCCGCGGCCGCAGAGCTATGCTTTGACCCTTAACTCCTATGGCATGATGGGGGCCCTGGGAGAAGCCAGGCAGCA
07 CAATATCAATTTCACTGTGTTGCAAGCAGCGGCCGCAGGAACTCTGTTTTGATCAACTTTGGCCATTCGGACTAGATGTGGCTCCAGAAATGGAGAAGCA
08 CAATAACCAAGACTGGGCGTTTTGATAAGCGGCCGCAGCCCTGAAACCGTCAACTCTCGTGGCTCGAAAAAGGGGCTCGGGGGGAGGGGGAAGTGGTCCA
09 CAATATGTATAGCAACGAGTTCATAAGTGCGGCCGCAGCCATGGATTGTTCCCTTAGTACTGCACGCCTTTTCTATGGAACTTTTTCAAATTATCTAAAT
10 CAATAATTATCGCTTAGATATTTGAGTCGCGGCCGCAGCTGATTCCTTAGAACTATGTGCATACCATAGTTTTATGTAATACTTGGAAAGTGTTCAATTT
11 CAATACATAAGTCTCTGTCGTTAAATTCGCGGCCGCAGCCCCTGAAACCGTCAACTCTCGTAATTCAAGTCTTTTTTTTTTTTTTTTTTTTTTTTTTTTT
12 CAATAGTGAATTCACGGACTGGTATTCGCGGCCGCAGCCCCCTGAAACCGTCAACTCTCGTGGCTGAACTTCTGCCTTCCCAATGGCTTTCGGATAATG
13 CAATAGGAAACGCGTGGTTATTGTACTAGCGGCCGCAGCTGTCTGCCCTCATAGGGCTTTCAGTCTAGTGGTAGGGACTGAAAAAATTCATGTGTGAGAA
14 CAATAGAAAAAGCGCAGGATTTGAATAGCGGCCGCAGGGGCAGCGGAGGTTCCTGGGGGAATCAAAGAGAAATGTGCCTCATTTTCCATTTGAGAAAATG
15 CAATACTAATCGCTAGGTTTTCTACGAGCGGCCGCAGATAACTACAGTTCAAACAAAGGAAATTAAAATGAGATTAAAGATCGGAAGAGCGGTTCAGCA
```

Mate-pairs read II (complement to 3' ends of above reads) 100 bases

```
01 ATCATCATCACACGAATTGGCAAAAACTAGAAACCAATCGCTATGCTATCAGAAGTCAGGATAGTGGGTATCCTTAGGCAAAGCTGGGAGTGGAGAGGGCA
02 AGTAGGCTTGTCTGTTAGGAGGACAGCAAACCTGGCATCAATATGCTGAATTTGCAGGTTTAGCAAACATTTCAGAATTTCTGCTTTTGTTGATGATCGA
03 CACCCTTTAGGGAAAAGTTATTTTGTTTACATTATTATAAGGGATTTGTGATGTCTGTAAAGTGTAACCTTTCTGCGGCCGCAGCTTTAACCCCATAGCA
04 CATTTACTTTTCCCTGCGGCCGCTACTGCGAGGCCCCAGTGTTCTATATTGAGATCGGAAGAGCGTCGTGTAGGGAAAGAGTGTAGATCTCGGTGGTCGG
05 TTTACTAATTGATTACTTTGTGAAGAAGAGAAGGCGCAACAACAACAATGATGAAGTCAATGCCAATAACTTAGAATGGTTATCAAGTCTGTGGGACTGG
06 GGACCAGCCGCCGCGCCTGGTCCCATCTTTCTAGATACATGTAGATATGTTTATTTTTATATGAAACTATGGGAAGGGATTCTATAATTTCCCAGATTCTA
07 AGAAATGTATACTTGAATTCTGCGGCCGCAATTTTCAATGCTCTGAAGTACTTATTGAGATCGGAAGAGCGTCGTGTAGGGAAAGAGTGTAGATCTCGGT
08 TTCTTAAGCAACATTCTTCTCTTCCCTAATAGCTACAATATGATACAGTACGCAACAGCTCACTTGAAAGTGCTAGAATCAAGGATCTTAAACCCAAAGT
09 TTAATGCACATCTGTTTTGCTGTTTTTTTGAGCAGTGTGCAGTGTAGGGTTCATGATAAATCATTGAACCACATGTGTAACAACTGAATGCCACTGAAAC
10 TTTTTAAAGTAATAGCTATCAGTAATAGCTGAGTGTTTTTTTTCCCTAATATTTCCTTGTGCAATTCAGACTTAAGCATCGAGTTTTTACCATCTTCCA
11 CTGAAACCGTCAACTCTCGTGGCTCGAAACAGGGGCTGCGGCCGCAAGTATGACAACAGCGAATTTATTATTGAGATCGGAAGAGCGTCGTGTAGGGAAA
12 ACCTTTATTCAACATTTCATCAGCCTGCGGCCGCCCATTTATAGTGCCGCGTCCTAAGTATTGAGATCGGAAGAGCGTCGTGTAGGGAAAGAGTGTAGATC
13 TTTTTTTTCTAAATCATTAGGTAAGAAATGACGCACATGAGAATAGTCCTTTTGTTTCTCATCTTCCTGAAAAGTCTTGTCTCTGGTTTTATTTGAAAGTG
14 TGCTTCCCCCAAAATGTATTTTATTTTATGCTACCATCTTAGTGGAAAGTCTGTAAGTTGTTAAAGCAACTGTTTACATTTCTGGGTAATGTTTTTTATT
15 TTTTTGTATTCTTACGTTTCTCTGCTTTGTAGTTGTGGCTGTACTTAAAGAAATACAGAATTTCATATATTTAAAAATGTTTAAAATGTGACCCACAGAA
```

FIGURE 7H read I [Marker Sequence]
[CAATATCCAGTCCGTGGACTTTTAAACTGCGGCCGCAG] AACTGGGAGACAAGAGCGGGCTCTCTCCTGAGATAAGACAAGTTTAACGTGAAGACCTTTTG >gb|BC106054.1| <u>Homo sapiens aldehyde dehydrogenase 18 family,</u>  (3297 nt)
rev-comp initn: 310 initn1: 310 opt: 310 Z-score: 391.3 bits: 81.6 E(632894): 1e-13
banded Smith-Waterman score: 310; 100% identity (100% similar) in 62 nt overlap (62-1:2494-2555)

```
              60        50        40        30        20        10
QUERY-  CAAAGGTCTTCACGTTAAACTTGTCTTATCTCAGGAGAGAGCCCGCTCTTGTCTCCCAGTT
        ::::::::::::::::::::::::::::::::::::::::::::::::::::::::::::
gb|BC1 TTTCCAAAAGGTCTTCACGTTAAACTTGTCTTATCTCAGGAGAGAGCCCGCTCTTGTCTCCCAGTTCCTGGTAGGGTCTGGCTGTTGGAAAGTGTACC
         2490      2500      2510      2520      2530      2540      2550      2560      2570      2580
``` read II
TCAGAGAAACACCAACTGAAAAGAGCCAGGAAAACCCGGGAATTTTCCAAAAGGTCTTCACGTTAAACTTGTCTTATCTCAGGAGAGAGCCCGCTCTTGT >gb|BC143930.1| <u>Homo sapiens aldehyde dehydrogenase 18 family,</u>  (3178 nt)
rev-comp initn: 500 initn1: 500 opt: 500 Z-score: 636.3 bits: 127.6 E(632857): 2.3e-27
banded Smith-Waterman score: 500; 100% identity (100% similar) in 100 nt overlap (1-100:2547-2646)

```
                                          10        20        30        40        50        60
QUERY-                            TCAGAGAAACACCAACTGAAAAGAGCCAGGAAAACCCGGGAATTTTCCAAAAGGTCTTCA
                                  ::::::::::::::::::::::::::::::::::::::::::::::::::::::::::::
gb|BC1 ATGGAAGTTTAAAATATCTTCATGAGAACCTCCCTATTCCTCAGAGAAACACCAACTGAAAAGAGCCAGGAAAACCCGGGAATTTTCCAAAAGGTCTTCA
         2510      2520      2530      2540      2550      2560      2670      2680      2690      2700

70        80        90       100
QUERY-  CGTTAAACTTGTCTTATCTCAGGAGAGAGCCCGCTCTTGT
        ::::::::::::::::::::::::::::::::::::::::
gb|BC1 CGTTAAACTTGTCTTATCTCAGGAGAGAGCCCGCTCTTGTCTCCCAGTTCCTGGTAGGGTCTGCCTGTTGGAAAGTGTACCTGGATGCTTCTGGGCTCCG
         2710      2720      2730      2740      2750      2760      2770      2780      2790      2800 gb|BC1 TTTGGCAATAGCAATCTTGCCTGATGTGCACAGTCTGGCT
         2810      2820      2830      2840
``` read I [Marker Sequence]
[CAATATTTAAATCTTTGTGTTTGAAACAGCGGCCGCAG] GGGTGCAGGTACACATGAGTTAGAGAGCTGGTGAGACAGTTGGGAACTCTTTGTGCTTGTAG >gb|AF063605.1| <u>Homo sapiens brain my047 protein mRNA</u>, complete cds  (2701 nt)
rev-comp initn: 295 initn1: 295 opt: 295 Z-score: 357.6 bits: 75.8 E(632894): 9.2e-12
banded Smith-Waterman score: 295; 100% identity (100% similar) in 59 nt overlap (40-98:2300-2358)

```
        20        30        40        50        60        70        80        90       100
QUERY-  TTTGAAACAGCGGCCGCAGGGGTGCAGGTACACATGAGTTAGAGAGCTGGTGAGACAGTTGGGGAACTCTTTGTGCTTGTAG
        ::::::::::::::::::::::::::::::::::::::::::::::::::::::::::::
gb|af0 GTTCAGATTTCAAGAGGAAGGTGCAGGTACACATGAGTTAGAGAGCTGGTGAGACAGTTGGGGAACTCTTTGTGCTTGTGATCTACTGGACTTTTTTTTT
         2290      2300      2310      2320      2330      2340      2350      2360      2370      2380
``` read II
ACAAGCACAAAGAGTTCCCAACTGTCTCACCAGCTCTCTAACTCATGTGTACCTGCACCCCTGCGGCCGCTGTTTCAAACACAAAGATTTAAATATTGAG >gb|AF063605.1| <u>Homo sapiens brain my047 protein mRNA</u>, complete cds  (2701 nt)
rev-comp initn: 295 initn1: 295 opt: 295 Z-score: 352.7 bits: 74.9 E(632857): 1.7e-11
banded Smith-Waterman score: 295; 100% identity (100% similar) in 59 nt overlap (59-1:2300-2358)

```
        80        70        60        50        40        30        20        10
QUERY-  GTTTGAAACAGCGGCCGCAGGGGTGCAGGTACACATGAGTTAGAGAGCTGGTGAGACAGTTGGGAACTCTTTGTGCTTGT
                                  ::::::::::::::::::::::::::::::::::::::::::::::::::::::::::
gb|af0 ATGTTCAGATTTCAAGAGGAAGGTGCAGGTACACATGAGTTAGAGAGCTGGTGAGACAGTTGGGAACTCTTTGTGCTTGTGATCTACTGGACTTTT
         2280      2290      2300      2310      2320      2330      2340      2360      2370      2380
```

FIGURE 7I

| T | A(150) | A(200) | N(150) | N(200) | cvg(150) | cvg(200) |
|---|---|---|---|---|---|---|
| 500 | 10 | 7.5 | 3.59 | 4.5 | 2.38 | 1.79 |
| 1,000 | 20 | 15 | 43.1 | 22.7 | 6.46 | 4.54 |
| 2,000 | 40 | 30 | 131 | 85 | 9.79 | 8.9 |
| 3,000 | 60 | 45 | 230 | 154 | 11.5 | 10.3 |
| 4,000 | 80 | 60 | 337 | 230 | 12.6 | 11.5 |
| 5,000 | 100 | 75 | 450 | 309 | 13.5 | 12.4 |
| 6,000 | 120 | 90 | 568 | 393 | 14.2 | 13.1 |
| 8,000 | 160 | 120 | 815 | 568 | 15.3 | 14.2 |
| 10,000 | 180 | 150 | 1074 | 752 | 16.1 | 15 |

$r = 3$ for all examples $\quad k = 5 \quad A = rT/kL$

SEQUENCE LISTING

```
<160> NUMBER OF SEQ ID NOS: 25

<210> SEQ ID NO 1
<211> LENGTH: 83
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: misc_feature
<222> LOCATION: (33)..(35)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t

<400> SEQUENCE: 1 gcagccctg acagccctg nnnannncnn ngnnntnnna nnngctcttc gagctcttcg      60
tttttttttt tttttttttt ttv                                            83

<210> SEQ ID NO 2
<211> LENGTH: 58
<212> TYPE: DNA
<213> ORGANISM: Artificial Sequence
```

```
<220> FEATURE:
<223> OTHER INFORMATION: Synthetic polynucleotide

<400> SEQUENCE: 2
aatgatacgg cgaccaccga gatctacact ctttccctac acgacgctct tccgatct      58

<210> SEQ ID NO 3
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 3
aatgatacgg cgaccaccga gatctacact ctttccctac acgacgctct tccgatctca    60
ata                                                                   63

<210> SEQ ID NO 4
<211> LENGTH: 238
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (62)..(64)
<223> OTHER INFORMATION: n is a, c, g, or t
<220> FEATURE:
<221> NAME/KEY: misc_feature
<222> LOCATION: (66)..(68)
<223> OTHER INFORMATION: n is a, c, g, or t
<220> FEATURE:
<221> NAME/KEY: misc_feature
<222> LOCATION: (70)..(72)
<223> OTHER INFORMATION: n is a, c, g, or t
<220> FEATURE:
<221> NAME/KEY: misc_feature
<222> LOCATION: (74)..(76)
<223> OTHER INFORMATION: n is a, c, g, or t
<220> FEATURE:
<221> NAME/KEY: misc_feature
<222> LOCATION: (78)..(80)
<223> OTHER INFORMATION: n is a, c, g, or t
<220> FEATURE:
<221> NAME/KEY: misc_feature
<222> LOCATION: (82)..(84)
<223> OTHER INFORMATION: n is a, c, g, or t
<220> FEATURE:
<221> NAME/KEY: misc_feature
<222> LOCATION: (155)..(157)
<223> OTHER INFORMATION: n is a, c, g, or t
<220> FEATURE:
<221> NAME/KEY: misc_feature
<222> LOCATION: (159)..(161)
<223> OTHER INFORMATION: n is a, c, g, or t
<220> FEATURE:
<221> NAME/KEY: misc_feature
<222> LOCATION: (163)..(165)
<223> OTHER INFORMATION: n is a, c, g, or t
<220> FEATURE:
<221> NAME/KEY: misc_feature
<222> LOCATION: (167)..(169)
<223> OTHER INFORMATION: n is a, c, g, or t
<220> FEATURE:
<221> NAME/KEY: misc_feature
<222> LOCATION: (171)..(173)
<223> OTHER INFORMATION: n is a, c, g, or t
<220> FEATURE:
<221> NAME/KEY: misc_feature
<222> LOCATION: (175)..(177)
<223> OTHER INFORMATION: n is a, c, g, or t

<400> SEQUENCE: 4
```

```
tttttttttt tttttttttt tttacactct ttccctacac gacgctcttc cgatctcaat    60
annnannncn nngnnntnnn annngcggcc gcaaatgcag ccCctgaaac cgtcaactct   120
cgtggctcga aacagggget gggactgcgg ccgcnnntnn nannncnnng nnntnnntat   180
tgagatcgga agagcgtcgt gtagggaaag agtgttttt tttttttttt tttttttv     238
```

```
<210> SEQ ID NO 5
<211> LENGTH: 47
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (26)..(28)
<223> OTHER INFORMATION: n is a, c, g, or t

<400> SEQUENCE: 5
caatannnan nncnnngnnn tnnnannngc ggccgcaaat gcagccc                  47

<210> SEQ ID NO 6
<211> LENGTH: 47
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (26)..(28)
<223> OTHER INFORMATION: n is a, c, g, or t

<400> SEQUENCE: 6
gttatnnntn nngnnncnnn annntnnncg ccggcgtcag ggtcggg                  47
```

<210> SEQ ID NO 7
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (26)..(28)
<223> OTHER INFORMATION: n is a, c, g, or t

<400> SEQUENCE: 7
caatannnan nncnnngnnn tnnnannngc ggccgcag                              38

<210> SEQ ID NO 8
<211> LENGTH: 1500
<212> TYPE: DNA
<213> ORGANISM: Artificial Sequence
<220> FEATURE:
<223> OTHER INFORMATION: Synthetic polynucleotide

<400> SEQUENCE: 8
caataaaaag gacctagata taacagctgc ggccgcagag gtggatatct tgacctacgt      60
ggcttggaag ataagtggtt ttcccaaaaa accgtgttat caataaccac ggcagtgtgg     120
tctgactagc ggccgcaggg gtggtgggat gattattgta atcatacttg gaacagaag     180 tgatgaaaaa ggtatgttac caataacaat gtctttgcgg tcttatttgc ggccgcagct    240
ggcaagatcg gaagagcggt tcagcaagaa tgccgagacc gatctcggat gccggcttct    300
caatacgaat ggctttggtc ttgtatatgc ggccgcagcc cctgaatctc tactttttt     360 tctctcatat agatcggaag agcggttcag caggaatgcc caataccaag atcggcgtta    420
ttccacccgc ggccgcagag ctatgctttg accttaact cctatggcat gatggggcc     480 ctgggagaag ccaggcagca caataccaag atcggcgtta ttccacccgc ggccgcagcc    540
cctaccgtca actctcgtgg ctcgaaacag gaatgatgga gggaagggac cgggactgcc    600
caatatcaat ttcactgtgt tgcaagcagc ggccgcagga actctgtttt gatcaacttt    660
ggccattcgg actagatgtg gctccagaaa tggagaagca caataaccaa gactgggcgt    720
tttgataagc ggccgcagcc ctgaaaccgt caactctcgt ggctcgaaaa aggggctcgg    780 ggggagggg aagtggtcca caatatgtat agcaacgagt tcataagtgc ggccgcagcc     840
atggattgtt cccttagtac tgcacgcctt ttctatggaa ctttttcaaa ttatctaaat    900
caataattat cgcttagata tttgagtcgc ggccgcagct gattccttag aactatgtgc    960

| | |
|---|---:|
| ataccatagt tttatgtaat acttggaaag tgttcaattt caatacataa gtctctgtcg | 1020 |
| ttaaattcgc ggccgcagcc cctgaaaccg tcaactctcg taattcaagt ctttttttt | 1080 |
| tttttttttt tttttttttt caatagtgaa ttcacggact tggtattcgc ggccgcagcc | 1140 |
| ccctgaaacc gtcaactctc gtggctgaac ttctgccttc ccaatggctt tcggataatg | 1200 |
| caataggaaa cgcgtggtta ttgtactagc ggccgcagct gtctgccctc atagggcttt | 1260 |
| cagtctagtg gtagggactg aaaaaattca tgtgtgagaa caatagaaaa aaccggagga | 1320 |
| tttgaatagc ggccgcaggg gagcggaggt tcctggggga atcaaagaga aatgtgcctc | 1380 |
| attttccatt tgagaaaatg caatactaat cgctaggttt ttctacgagc ggccgcagat | 1440 |
| aactacagtt caaacaaagg aaattaaaat gagattaaag atcggaagag cggttcagca | 1500 |

<210> SEQ ID NO 9
<211> LENGTH: 1500
<212> TYPE: DNA
<213> ORGANISM: Artificial Sequence
<220> FEATURE:
<223> OTHER INFORMATION: Synthetic polynucleotide

<400> SEQUENCE: 9

| | |
|---|---:|
| atcatcatca cacgaattgg caaaaactag aaaccaatcg ctatgctatc agaagtcagg | 60 |
| atagtgggta tccttaggaa agctgggagt ggagagggca gtaggcttg tctgttagga | 120 |
| ggacagcaaa cctggcatca atatgctgaa tttgcaggtt tagcaaacat ttcagaattt | 180 |
| ctgcttttgt tgatgatcga cacccttag ggaaagttat ttttgtttac attattataa | 240 |
| gggatttgtg atgtctgtaa agtgtaacct ttctgcggcc gcagctttaa ccccatagca | 300 |
| catttacttt tccctgcggc cgctactgcg aggccccagt gttctatatt gagatcggaa | 360 |
| gagcgtcgtg tagggaaaga gtgtagatct cggtggtcgg tttactaatt gattactttg | 420 |
| tgaagaagag aaggcgcaac aacaacaatg atgaagtcaa tgccaataac ttagaatggt | 480 |
| tatcaagtct gtgggactgg ggaccagccg ccgcgcctgg tccatctttc tagatacatg | 540 |
| tagatatgtt tattttata tgaaactatg ggaagggatt ctataatttc ccagattcta | 600 |
| agaaatgtat acttgaattc tgcggccgca attttcaatg ctctgaagta cttattgaga | 660 |
| tcggaagagc gtcgtgtagg gaaagagtgt agatctcggt ttcttaagca acattcttct | 720 |
| cttccctaat agctacaata tgatacagta cgcaacagct cacttgaaag tgctagaatc | 780 |
| aaggatctta aacccaaagt ttaatgcaca tctgtttgc tgttttttg agcagtgtgc | 840 |
| agtgtagggt tcatgataaa tcattgaacc acatgtgtaa caactgaatg ccactgaaac | 900 |
| tttttaaagt aatagctatc agtaatagct gagtgttttt tttccctaat attttccttg | 960 |
| tgcaattcag acttaagcat cgagttttta ccatcttcca ctgaaaccgt caactctcgt | 1020 |
| ggctcgaaac aggggctgcg gccgcaagta tgacaacagc gaatttatta ttgagatcgg | 1080 |
| aagagcgtcg tgtagggaaa accttttattc aacatttcat cagcctgcgg ccgccattta | 1140 |
| tagtgccgcg tcctaagtat tgagatcgga agagcgtcgt gtagggaaag agtgtagatc | 1200 |
| ttttttttcta aatcattagg taagaaatga cgcacatgag aatagtcctt tgtttctca | 1260 |
| tcttcctgaa aagtcttgtc tctggttta tttgaaagtg tgcttccccc aaaatgtatt | 1320 |
| ttattttatg ctaccatctt agtggaaagt ctgtaagttg ttaaagcaac tgtttacatt | 1380 |
| tctgggtaat gttttttatt ttttgtatt cttacgtttc tctgctttgt agttgtggct | 1440 |
| gtacttaaag aaatacagaa tttcatatat ttaaaaatgt ttaaaatgtg acccacagaa | 1500 |

```
<210> SEQ ID NO 10
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 10
caatatccag tccgtggact tttaaactgc ggccgcagaa ctgggagaca agagcgggct    60
ctctcctgag ataagacaag tttaacgtga agacctttg                         100

<210> SEQ ID NO 11
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 11
caaaaggtct tcacgttaaa cttgtcttat ctcaggagag agcccgctct tgtctcccag    60
tt                                                                 62

<210> SEQ ID NO 12
<211> LENGTH: 159
<212> TYPE: DNA
<213> ORGANISM: Homo sapiens

<400> SEQUENCE: 12
acaccaactg aaaagagcca ggaaaacccg ggaattttcc aaaaggtctt cacgttaaac    60
ttgtcttatc tcaggagaga gcccgctctt gtctcccagt tcctggtagg gtctgcctgt   120
tggaaagtgt acctggatgc ttctgggctc cgtttggca                         159

<210> SEQ ID NO 13
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 13
tcagagaaac accaactgaa aagagccagg aaaacccggg aattttccaa aaggtcttca    60
cgttaaactt gtcttatctc aggagagagc cgctcttgt                         100

<210> SEQ ID NO 14
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 14
tcagagaaac accaactgaa aagagccagg aaaacccggg aattttccaa aaggtcttca    60
cgttaaactt gtcttatctc aggagagagc cgctcttgt                         100

<210> SEQ ID NO 15
<211> LENGTH: 240
<212> TYPE: DNA
<213> ORGANISM: Homo sapiens

<400> SEQUENCE: 15
atggaagttt aaaatatctt catgagaacc tccctattcc tcagagaaac accaactgaa    60
```

```
aagagccagg aaaacccggg aattttccaa aaggtcttca cgttaaactt gtcttatctc    120
aggagagagc ccgctcttgt ctcccagttc ctggtagggt ctgcctgttg gaaagtgtac    180
ctggatgctt ctgggctccg tttggcaata gcaatcttgg ctgatgtgca cagtctggct    240

<210> SEQ ID NO 16
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 16
caatatttaa atctttgtgt ttgaaacagc ggccgcaggg gtgcaggtac acatgagtta     60
gagagctggt gagacagttg ggaactcttt gtgcttgtag                          100

<210> SEQ ID NO 17
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 17
caatatttaa atctttgtgt ttgaaacagc ggccgcaggg gtgcaggtac acatgagtta     60
gagagctggt gagacagttg ggaactcttt gtgcttgtag                          100

<210> SEQ ID NO 18
<211> LENGTH: 160
<212> TYPE: DNA
<213> ORGANISM: Homo sapiens

<400> SEQUENCE: 18
agtggcttgt ggtattataa tgttcagatt tcaagaggaa ggtgcaggta cacatgagtt     60
agagagctgg tgagacagtt gggaactctt tgtgcttgtg atctactgga cttttttttt    120
gcaggaagtg cattctctgg tccttcccta ttttctgttc                          160

<210> SEQ ID NO 19
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 19
acaagcacaa agagttccca actgtctcac cagctctcta actcatgtgt acctgcaccc     60
ctgcggccgc tgtttcaaac acaaagattt aaatattgag                          100

<210> SEQ ID NO 20
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 20
tcaatattta atctttgtgt tttgaaacag cggccgcagg ggtgcaggta cacatgagtt     60
agagagctgg tgagacagtt gggaactctt tgtgcttgt                            99

<210> SEQ ID NO 21
<211> LENGTH: 160
```

```
<212> TYPE: DNA
<213> ORGANISM: Homo sapiens

<400> SEQUENCE: 21
agtggcttgt ggtattataa tgttcagatt tcaagaggaa ggtgcaggta cacatgagtt      60
agagagctgg tgagacagtt gggaactctt tgtgcttgtg atctactgga cttttttttt     120
gcaggaagtg cattctctgg tccttcccta ttttctgttc                           160

<210> SEQ ID NO 22
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 22
aaaaaaaaaa aaaaaaaaaa aaaaaaaaaa a                                     31

<210> SEQ ID NO 23
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 23
aaaaaaaaaa aaaaaaaaaa aaaaaa                                           26

<210> SEQ ID NO 24
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 24
tttttttttt tttttttttt tttttt                                           26

<210> SEQ ID NO 25
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 25
tttttttttt tt                                                          12
```

METHODS OF SEQUENCING NUCLEIC ACIDS IN MIXTURES AND COMPOSITIONS RELATED THERETO

CROSS REFERENCE TO RELATED APPLICATIONS

This is the U.S. National Stage of International Application No. PCT/US2014/016673, filed Feb. 17, 2015, which was published in English under PCT Article 21(2), which in turn claims the benefit of U.S. Provisional Application No. 61/766,841, filed Feb. 20, 2013, hereby incorporated by reference in its entirety.

BACKGROUND

An individual gene can often give rise to new proteins in different cells or stages of differentiation, including cells not normally encountered in the life cycle of the organism (e.g., cancer cells; cells in culture; cells in developmental neuro-anatomical anomalies). The different proteins arise from differential patterns of transcription activation and post-transcriptional RNA processing of the messenger RNA (mRNA) that specifies the protein in the expressing cell.

The population of mRNA "transcripts" that are found in a cell is referred to herein as the "transcriptome." The state of the art for transcriptome sequencing is "RNA-Seq." See *Nature Methods* (2008) 5, 621-628. In this approach, mRNAs isolated from a tissue or cell culture are reverse transcribed into complementary DNA (cDNA), and the cDNA is processed and amplified to produce a library of short fragments which are sequenced. mRNA in the cell cannot be profiled by overlapping the sequence of the cDNA fragments and aligning them to a sequence in the genome. The population of most likely mRNAs is, instead, assembled with the use of complex statistical algorithms, the validity of which is an active subject of ongoing of research. RNA-Seq does provide information regarding the tissue-specific 'exome,' comprising genomic sequences retained in messenger RNAs, including segments specifying protein coding domains.

RNA-Seq methods do not retain certain information about sequence variants largely because individual mRNA transcripts typically include several variable regions, usually separated by a distance far in excess of the sequencer cDNA read lengths. Which combinations of variable regions are found on the same mRNA transcript is thus unclear.

Consider for illustration a gene that encodes a protein with two "optional" domains separated by 1500 nucleotides: a calcium binding domain (C) near the amino terminus and a calmodulin-binding domain (M) on the carboxyl terminus. The transcripts of this gene may be alternatively spliced to retain both domains (CM), only one domain (cM or Cm) or neither (cm) in the final mRNA. The expressed protein may have four very different physiological behaviors depending on which domains are present. If an RNA-Seq experiment reveals both variations of both domains, one is entirely without recourse to deduce which transcripts are actually present in the original mRNA pool: the data support any of the following sets of transcripts: {CM, cm}, {cM, Cm}, {CM, cm, cM, Cm}, etc. This is because the long region connecting domains C and M contains the same sequence in all transcript variants.

The challenge for large scale cDNA sequencing, as demonstrated in the previous description, is intrinsically linked to the biology of genes of higher species. The uncertainty as to which messages will be expressed in a given cell or stage of cellular differentiation is matched by the uncertainty with which short reads from highly parallel cDNA sequencing can be assigned to particular transcripts. Thus, there is a need to capture more information in the biochemical conduit between genome and proteome.

Fu et al., report molecular indexing enables quantitative targeted RNA sequencing and reveals poor efficiencies in standard library preparations. Proc Natl Acad Sci USA. 2014, 111(5):1891-6.

Certain methods have been described as potentially providing large scale transcriptome sequencing. These are limited in their application. Zamore et al., PCT Publication WO 2011/049955 entitled "Deducing Exon Connectivity by RNA-Templated DNA Ligation/Sequencing," provide certain sequencing methods including a method in which RNA is annealed to oligomers complementary to known alternative splice junctions each bearing a randomized bar code. This is followed by ligation and subsequent sequencing. The method is limited as it requires prior knowledge of the exon junctions and does not sequence each mRNA in its entirety.

Parallel tagged sequencing (PTS) is also a molecular bar-coding method. See Meyer et al., Nature Protocols, 2007 3, 267-278. The method relies on attaching sample-specific barcoding adapters, which include sequence tags and a restriction site, to blunt-end repaired DNA samples by ligation and strand-displacement. Using the tag sequences, the sample source of each DNA sequence is traced.

Parameswaran et al., Nucleic Acids Res., 2007, 35(19): e130, published a method to increase barcode diversity combinatorially to enable pooled sequencing of libraries from sample sources. Only the sample-specific tags are used. Individual transcripts are not distinguishable, or fully sequenced.

Craig et al., Nat Methods., 2008, 5(10): 887-893 describe a method for multiplexed sequencing of targeted regions of the human genome on the Illumina Genome Analyzer using degenerate indexed DNA sequence barcodes ligated to fragmented DNA prior to sequencing.

Halbritter et al. report high-throughput mutation analysis in patients with a nephronophthisis-associated ciliopathy applying multiplexed barcoded array-based PCR amplification and next-generation sequencing. See J Med Genet. 2012, 49:756-767.

Sharon et al. report a single-molecule long-read survey of the human transcriptome. Nat Biotechnol, 2013, 31:1009-14.

References cited herein are not an admission of prior art.

SUMMARY

This disclosure relates to obtaining full-length (end-to-end) sequences of individual polynucleotides present in a heterogeneous mixture. It further relates to the design, synthesis and methods of preparing specialized reagents that enable such analyses. In certain embodiments, the disclosure relates to completely sequencing and quantifying mRNAs in the transcriptomes of a cell or tissue of a higher multicellular organism. Disclosed methods allow efficient, economical, sequencing of full-length mRNAs specifying the molecular phenotype of cells and tissues of higher multicellular organisms. In certain embodiments, the disclosure relates to commercial kits comprising reagents and methods of application for conducting such analyses.

In certain embodiments, the disclosure relates to methods comprising a) mixing a sample and a group of tagging polynucleotides, wherein the sample comprises a mixture of nucleic acids of different length and/or different sequence, wherein the tagging polynucleotides individually comprise overlapping sequences and a part with random sequences, and wherein the mixing is done under conditions such that the tagging polynucleotides bind the nucleic acids to form nucleic acids individually tagged with random sequences; b) replicating the nucleic acid mixture of individually tagged with random sequences into a mixture of homopolymers, wherein the homopolymers comprise a repeating nucleic acid and a repeating sequence tag; c) breaking the homopolymers, e.g., by enzymatic fragmentation, heating, shearing, sonicating, or exposure to one or more restriction enzymes, providing homopolymer fragments; and d) sequencing the homopolymer fragments. The homopolymer fragments are typically less than 1000, 2000, or 5000 nucleotide bases long. In certain embodiments, breaking the homopolymers is done randomly. In certain embodiments, breaking the homopolymers is done with a restriction nuclease or equivalent agent that cleaves a site within the overlapping sequences on the tagging polynucleotides providing cleaved homopolymer fragments.

In certain embodiments, the method further comprises the steps of mixing the homopolymer fragments with a restriction nuclease that cleaves a site within the overlapping sequences on the tagging polynucleotides providing cleaved homopolymer fragments with a tagging sequence on one end and a random internal break point of the target nucleic acid on the other.

In certain embodiments, the method further comprises the step of sequencing the cleaved homopolymer fragments.

In certain embodiments, the method further comprises the step of identifying tagged sequences within the homopolymer fragments, separating identical sequences within the part of random sequences, and reconstructing a nucleic acid sequence that was in the sample from the associated random internal sequences of the target nucleic acids.

In certain embodiments, the tagging polynucleotides comprise a palindromic sequence configured to self-hybridize into a double stranded segment wherein the double stranded segment comprises a restriction site. Typically, the restriction site is a rare restriction site.

In certain embodiments, the disclosure relates to kits comprising a tagging polynucleotide disclosed herein and optionally a reverse transcriptase other viral reverse transcriptase, or any comparable enzymes of other origins that creates a double stranded nucleic acid from a single stranded RNA, nucleotides, and other reagents disclosed herein. In certain embodiments, the kit comprises instructions detailing methods disclosed herein.

In certain embodiments, a unique label is associated with each nucleic acid in a sample of nucleic acids. In some embodiments, the unique label includes a source molecule identifier (SMID). In certain embodiments, individual nucleic acids are replicated as long, tandem homopolymers including, at every junction/subunit repeat, a unique identifying sequence. In certain embodiments of step c), homopolymers are randomly fragmented, and in some embodiments, selectively cleaved to provide fragments that include a SMID. In certain embodiments, the SMID and the random break sequence are sequenced together, typically in parallel redundant fashion, and sequences are segregated according to molecular source. In some embodiments, these sequences are analyzed by overlapping reads to provide the consensus sequence of the full-length mRNA source molecule. In certain embodiments the sequences are analyzed by alignment with gene sequences recalled from established gene databases and compared with exon boundaries reported in established gene databases. In certain embodiments the sequences are analyzed by alignment with sequences retrieved from transcript databases. In certain embodiments the sequences are analyzed by alignment with non-coding cDNA sequences retrieved from cDNA databases. In some embodiments, the disclosure provides a method to quantify mRNAs in a sample, including sequence variants derived from every gene activated for transcription.

In certain embodiments, the disclosure relates to methods for full length sequencing of a plurality of heterogeneous polynucleotides of varying length and composition in solution together. Typically the heterogeneous polynucleotides are RNAs, e.g., mRNA or micro-RNA. Typically, the mRNAs are mature and capped mRNAs. In certain embodiments, the heterogeneous polynucleotides are microbial and viral genomes.

In certain embodiments, the disclosure relates to methods comprising: a) providing double stranded nucleic acid fragments, typically of less than 1000, 2000, or 5000 nucleotides, comprising a tagging part and a target part, wherein the tagging part comprises a segment of overlapping sequences and a segment of varying sequences, wherein the overlapping sequences comprise a first primer site and a restriction site; b) mixing the double stranded fragments with a restriction enzyme to the restriction site providing cleaved fragments; c) mixing the cleaved fragments with an enzyme under conditions such that the cleaved fragments form circular fragments; d) breaking the circular fragments at random points providing sheared fragments; e) ligating an adaptor to the ends of the double stranded nucleic acids wherein the adaptor comprises a second primer site providing an adaptor nucleic acid conjugate; f) amplifying the adaptor nucleic acid conjugates with primers to the first and second primer sites, wherein the first primer comprises a first capture sequence on the 5' end and the second primer comprises a second capture sequence on the 5' end to provide a capture target tagged conjugate; and g) sequencing the capture target tag conjugate.

In certain embodiments, the segment of varying sequences is between the first primer site and the target part. In certain embodiments, the first primer site is between the segment of varying sequences and the target part. In certain embodiments, the restriction site is between the segment of varying sequences and the first primer site. In certain embodiments, the segment of varying sequences is between the restriction site and the first primer site. In certain embodiments, the nucleic acid fragments comprises two segments of varying sequences wherein the varying segments are identical sequences and the restriction site is between the identical sequences.

In certain embodiments, the disclosure relates to methods comprising a) mixing a sample and a group of tagging polynucleotides, wherein the sample comprises a mixture of nucleic acids of different length and/or different sequence, wherein the tagging polynucleotides individually comprise overlapping sequences and a part with random sequences, and wherein the mixing is done under conditions such that the tagging polynucleotides bind the nucleic acids to form nucleic acids individually tagged with random sequences; b) replicating the nucleic acid mixture individually tagged with random sequences into a mixture of homopolymers, wherein the homopolymers comprise a repeating nucleic acid and a repeating sequence tag; c) breaking the homopolymers at random points providing homopolymer fragments; d) mixing the homopolymer fragments with a restriction nuclease that cleaves a site correlated to the overlapping sequences on the tagging polynucleotides providing cleaved homopolymer fragments; and e) sequencing the cleaved homopolymer fragments.

In certain embodiments, the method further comprises identifying tagged sequences within the homopolymer fragments, separating identical sequences within the part of random sequences, and reconstructing a nucleic acid sequence that was in the sample. In further embodiments, the tagging polynucleotides comprise a palindromic sequence configured to self-hybridize into a double stranded segment wherein the double stranded segment comprises a restriction site. Typically, the restriction site is a rare restriction site. The tagging polynucleotides may bind the nucleic acids covalently or non-covalently.

In certain embodiments, the disclosure relates to methods comprising a) mixing a sample and a group of tagging polynucleotides, wherein the sample comprises a mixture of nucleic acids of different length and/or different sequence, wherein the tagging polynucleotides individually comprise overlapping sequences and a part with random sequences and wherein the tagging polynucleotides comprise a palindromic sequence configured to self-hybridize into a double stranded segment wherein the double stranded segment comprises a restriction site, wherein the part with random sequences is within the double stranded segment, and wherein the mixing is done under conditions such that the tagging polynucleotides bind the nucleic acids to form nucleic acids individually tagged with random sequences; b) replicating the nucleic acid mixture individually tagged with random sequences into a mixture of homopolymers, wherein the homopolymers comprises a repeating nucleic acid and a repeating sequence tag, to produce homopolymer fragments; c) mixing the homopolymer fragments with a restriction nuclease that cleaves a site correlated to the overlapping sequences on the tagging polynucleotides providing cleaved homopolymer fragments; and d) sequence the cleaved homopolymer fragments.

In certain embodiments, the disclosure relates to methods comprising: a) mixing more than 3, 4, 5, 10, 100, or 1000 unique mRNA of a different size and/or sequence with hairpin polynucleotides comprising a poly-T tail of greater than 4, 5, 6, 7, 8, 9, or 10 nucleotide, wherein the hairpin polynucleotides comprise a segment of varying sequences within a double stranded part of the hairpin and a restriction site within the double stranded part of the hairpin, under conditions such that hairpin mRNA conjugates are formed; b) mixing the hairpin mRNA conjugates with replication reagents under conditions such that cDNA complements are formed; c) circularizing the cDNA complements; d) amplifying the cDNA complements by mixing with primers and replication reagents forming double stranded homopolymers with a unique mRNA sequences and a unique sequence segment; e) mixing the double stranded homopolymers with a restriction enzyme to the restriction site in the hairpin polynucleotide sequence forming fragments, or mixing with a sequence-specific chemical agent with a cleavage site in the hairpin polynucleotide sequence forming fragments; and f) sequencing the fragments.

In certain embodiments, the disclosure relates to methods comprising a) mixing more than 3, 4, 5, 10, 100, or 1000 unique circularized mRNA of a different size and/or sequence with hairpin polynucleotides comprising a poly-T tail of greater than 4, 5, 6, 7, 8, 9, or 10 nucleotide, wherein the hairpin polynucleotides comprise a segment of varying sequences within a double stranded part of the hairpin and a restriction site within the double stranded part of the hairpin, under conditions such that hairpin mRNA conjugates are formed; b) mixing the hairpin mRNA conjugates with replication reagents under conditions such that circular cDNA complements are formed; c) amplifying the circular cDNA complements by mixing with primers and replication reagents forming double stranded homopolymers with a unique mRNA sequences and a unique sequence segment; e) mixing the double stranded homopolymers with a restriction enzyme to the restriction site in the hairpin polynucleotide sequence forming fragments or mixing with a sequence-specific chemical agent with a cleavage site in the hairpin polynucleotide sequence forming fragments; and f) sequencing the fragments.

In certain embodiments, the methods disclosure herein further comprise the step of grouping the unique sequence segments to reconstruct the mRNA sequences and recording the sequences on a computer.

In certain embodiments, the disclosure relates to methods of amplifying a plurality of mRNA in a sample comprising: a) mixing a plurality of tagging polynucleotides with a sample comprising a plurality of mRNAs under conditions such that the tagging polynucleotides hybridize to the mRNAs forming mRNA tagging reagent nucleic acids, wherein the tagging reagent polynucleotides comprise a poly-T sequence, a sequence-identifiable area of random sequences that are not substantially identical, and a restriction site; b) mixing the mRNA tagging reagent nucleic acids with a reverse transcriptase under conditions such that complementary tagged nucleic acids are formed; c) circularizing the complementary tagged nucleic acids, providing tagged circular complementary nucleic acids, and e) amplifying the circular complementary tagged nucleic acids, providing amplified complementary nucleic acids tagged according to the mRNA source molecules. Typically, the restriction site is a rare restriction site.

In certain embodiments, circularizing complementary tagged nucleic acids provides circular single stranded complementary tagged nucleic acids. In certain embodiments, circularizing the single stranded complementary tagged nucleic acids comprises mixing the single stranded complementary tagged nucleic acids with a ligase that cannot ligate double stranded nucleic acids. In certain embodiments, amplifying the circular complementary tagged nucleic acids comprises generating repeating sequences of the complementary tagged nucleic acids. In certain embodiments generating repeating sequences of complementary tagged nucleic acids comprises mixing the circular single stranded complementary tagged nucleic acid with a polymerase and primers, wherein the polymerase displaces double-stranded nucleic acids from a template during nucleic acid syntheses. In certain embodiments, the primers are random sequences, or hybridize to an area on the tagging polynucleotide or hybridize to sequences derived from a target gene or derived from members of a target multi-gene family or from members of multiple multi-gene families. In certain embodiments, the primers are random sequences selected from pentamers, hexamers, heptamers, and combinations thereof.

In certain embodiments, the disclosure contemplates methods comprising the step of breaking amplified complementary tagged nucleic acids into segments comprising the sequence-identifiable areas.

In certain embodiments, breaking the amplified complementary tagged nucleic acids comprises random and/or specific breaks by physical disruption and/or chemical disruption within predetermined sites in the tagging reagent sequence. In certain embodiments, the segments are less than 2000, 1000, or 500 nucleotides. In certain embodiments the methods disclosed herein comprise the step(s) of sequencing the amplified complementary tagging nucleic acid segments, storing the sequenced segments on a computer, and analyzing the sequence-identifiable areas and overlapping unique random sequences to generate individual mRNA sequences in the sample; and identifying a pattern of individual mRNA sequences in the sample. The pattern can be correlated to a phenotype of the sample. In certain embodiments, the sample comprises diseased cells, such as cancer cells.

In certain embodiments, the disclosure relates to tagging reagents such as type I, type II-$ps_1$; type II-$ps_2$; type II-$pa_1$; type II-$pa_2$ and; type II-t. In certain embodiments, the tagging reagent comprises a first sequence-identifiable area of random sequences and a second sequence-identifiable area of random sequences and a poly-T segment. In some embodiments, the second sequence-identifiable area is the reverse complement of the first sequence identifiable area. Typically the tagging reagent further comprises a palindromic sequence forming a restriction site sequence, wherein the palindromic sequence is positioned between the first sequence identifiable area of random sequences and the second sequence identifiable area of random sequences. In some embodiments, the tagging reagent comprises a loop sequence with a primer site sequence of more than 5 or 10 nucleotides. In some embodiments, the tagging reagent polynucleotide comprises a primer site between the poly-T sequence and the first sequence-identifiable area of random sequences.

In certain embodiments, the disclosure relates to compositions comprising a mixture of polynucleotides each individually comprising overlapping sequences, a part with random sequences, a part with poly-T of greater than 5, 10, or 15 nucleotides, and a restriction site. In some embodiments, the poly-T is about the 3' end and the part with random sequences is between the poly-T and a restriction site. In some embodiments, polynucleotides comprise a palindromic sequence configured to self-hybridize into a double stranded segment wherein the double stranded segment comprises a restriction site. In some embodiments, the part with random sequences is within the double stranded segment. In some embodiments, the poly-T is about the 3' end and a second poly-T is about the 5' end. Typically, the restriction site is a rare restriction site. Typically, the part with random sequences comprises random base sites or sequences intersperse with overlapping sequences.

In certain embodiments, the disclosure relates to compositions comprising mixture of polynucleotides each individually comprising overlapping sequences, a part with random sequences, a second part duplicating the same random sequences, a part with poly-T of greater than 5, 10, or 15 nucleotides, and a restriction site between the part with random sequences and the second part duplicating the same random sequences.

In certain embodiments, the disclosure contemplates compositions comprising a polynucleotide mixture wherein a part of the sequence in the individual nucleotides comprise substantially overlapping sequences and a part of the sequence in the individual nucleotides comprise substantially non-overlapping sequences, wherein the individual nucleotides comprise a sequence of repeating nucleotides with thymine or uracil bases of greater than 5, 10, 15, or 20 nucleotides, and wherein the substantially overlapping sequences comprise a rare restriction site. Typically, the individual nucleotides comprise greater than 50, 100, or 150 nucleotide bases. Typically, the individual nucleotides comprise less than 500, 1000, 2000, 5000, or 10,000 nucleotide bases. In some embodiments, the polynucleotide mixture further comprises palindromic nucleotides having a part with overlapping and non-overlapping sequences. Typically the palindrome creates a structure that forms a hairpin wherein more than 10, 20, 50 base pair sequences hybridize to each other.

In certain embodiments, the disclosure contemplates compositions comprising a polynucleotide mixture wherein a part of the sequence in the individual nucleotides comprise substantially overlapping sequences and a part of the sequence in the individual nucleotides comprise substantially non-overlapping sequences, wherein the individual nucleotides comprise a sequence of repeating nucleotides with adenine bases of greater than 10, 15, or 20 nucleotides and wherein part of the overlapping sequences are a palindrome in the individual nucleotides. In some embodiments, a part of the non-overlapping sequences are a palindrome in the individual nucleotides. In some embodiments, a part of the overlapping sequences are not the reverse complement in the individual nucleotides.

In certain embodiments, the disclosure relates to loop primers RNA-second strand primers, PCR-primers, adapters, single stranded, truncated, and isolated nucleic acids disclosed herein.

In certain embodiments, the disclosure relates to methods for the solution or solid phase synthesis of reagents disclosed herein. In certain embodiments, the disclosure relates to methods of using reagents disclosed herein in combination with massively parallel genome sequencing technology including analyses of the statistical structures and compositions of transcriptomes; the isolation of molecular variants identified by massively parallel sequencing.

In certain embodiments, the disclosure relates to methods of isolating target nucleic acids comprising: a) providing fragmented double stranded nucleic acids comprising a tagging part and a target part, wherein the tagging part comprises a segment of overlapping sequences and a segment of varying sequences, wherein the overlapping sequences comprise a first primer site and a second primer site, wherein the segment of varying sequence is between the first and the second primer sites, wherein the first primer site and second primer site are the same sequence on opposite strands of the nucleic acids; b) ligating an adaptor to the ends of the double stranded nucleic acids wherein the adaptor comprises a third primer site providing an adaptor nucleic acid conjugate; c) amplifying the target part by mixing the adaptor nucleic acid conjugate, a first primer, a second primer, and replication reagents under conditions such that the first primer hybridizes to the first and second primer site, and the third primer hybridizes to the second primer site providing isolated nucleic acids between the primer sites comprising the varying sequence and the target part.

In certain embodiments, the nucleic acids comprise a restriction site within the overlapping sequences and the methods further comprise the step of mixing the nucleic acids with a restriction enzyme to the restriction site providing cleaved nucleic acids prior to ligating an adaptor to the cleaved double stranded nucleic acids. In some embodiments, the restriction site is between the varying sequences and the primer sites, and in some embodiments, the restriction site is between two identical varying sequences.

In certain embodiments, the disclosure relates to methods of amplifying a plurality of mRNA in a sample comprising a) mixing a plurality of tagging polynucleotides with a sample comprising a plurality of mRNAs under conditions such that the tagging reagent polynucleotides hybridize to the mRNAs forming a mRNA tagging reagent nucleic acids, wherein the tags comprise a palindromic sequence forming a restriction site sequence, a first sequence-identifiable area of random sequences, a second-sequence identifiable area of random sequences, and a poly-T segment about one end, wherein the second sequence-identifiable area is the reverse complement of the first sequence identifiable area, and wherein the palindromic sequence is positioned between the first and the second sequence-identifiable area of random sequences; b) mixing the mRNA tagging reagent nucleic acids with a reverse transcriptase under conditions such that complementary tagged nucleic acids are formed; c) separating the complementary tagged nucleic acids from the mRNA providing single stranded complementary-joiner nucleic acids; d) circularizing the single stranded complementary tagged nucleic acids providing circular complementary tagged nucleic acids, and e) amplifying the circular complementary tagged nucleic acids providing amplified complementary joiner nucleic acids f) breaking amplified complementary tagged nucleic acids into segments comprising the sequence identifiable areas by mixing with a restriction enzyme.

In certain embodiments, the methods disclosed herein comprise conjugating a label to the ends of the segments providing label bound amplified complementary tagged nucleic acid segments. In some embodiments, the label is biotin. In certain embodiments, the method further comprises the steps of circularizing and fragmenting the segments; purifying the segments by mixing the label bound amplified complementary tagged nucleic acid segments with a substrate that binds the label; and releasing the amplified complementary tagged nucleic acid segments and sequencing the segments.

In certain embodiments, the disclosure relates to methods of producing a nucleic acid comprising: a) mixing a primer and replicating reagents with starting hairpin polynucleotides comprising a 3' poly-T, an overlapping sequence, a part with random sequences, and a loop, wherein the primer is to the loop sequence, to form a partially double stranded and partially single stranded nucleic acid; and b) mixing the partially double stranded and partially single stranded nucleic acid with a poly-A primer and replicating agents to form an entirely double stranded nucleic acid. In certain embodiments, the method further comprises the step of cleaving the poly-A primer to provide double stranded nucleic acids with a poly-T tail. In certain embodiments, the method further comprises the step of denaturing the double stranded nucleic acids to form hairpin nucleic acids with a poly-T tail and the starting hairpin polynucleotides. Typically, the starting hairpin polynucleotides are conjugated to a solid support.

In certain embodiments, the disclosure contemplates solid supports made by the above method comprising hairpin polynucleotide as described herein.

In certain embodiments, the disclosure relates to methods of producing a polynucleotide comprising a) mixing a template polynucleotide which is a substantially double stranded nucleic acid except for a loop sequence, a primer to a loop sequence primer site, and a polymerase, wherein the template polynucleotide comprises a loop sequence primer site and a second primer site within the double stranded nucleic acid, wherein the polymerase displaces double-stranded nucleic acids from the template during nucleic acid syntheses, to form a partially double-stranded and single-stranded nucleic acid; b) mixing the partially double-stranded and single-stranded nucleic acid with a primer to the second primer site, and a polymerase, wherein the polymerase displaces double-stranded nucleic acids from the template during nucleic acid syntheses, to form a double-stranded nucleic acid; and c) heating the double stranded nucleic acid to denature, release an polynucleotide, and reform the template polynucleotide. In certain embodiments, the template polynucleotide is conjugated to a solid support; the template polynucleotide comprises a poly-A segment about one end; the primer site for second strand synthesis is adjacent to the poly-A segment; the template polynucleotide comprises a first area of identifiable random sequences adjacent to the primer site for second strand synthesis; and the template comprises a palindromic sequence comprising a restriction site adjacent to the loop sequence. In certain embodiments, the palindromic sequence is adjacent to the first area of identifiable random sequences.

In certain embodiments, the disclosure relates to the analysis of molecular phenotype of cells or tissues, the analysis of diseased cells or tissues, and the establishment of transcriptomic databases.

In certain embodiments, methods disclosed herein comprise the processing of tagged oligonucleotides in such a way as to amplify and then fragment copies of each in such a way that the original tag is replicated in association with the internal fragments produced and computational recovery of the associative information required to reconstruct the sequences and relative numbers of oligonucleotides in the original heterogeneous solution.

This step has been modified by introducing the annealing site for PCR Primer 1.0 into the Marker sequence. Instead of the proprietary forked adapter, a modified adapter attaches a segment complementary only to PCR Primer 2.0 to the 3' ends of the fragment. As a result (a) only Streptavidin captured junctional sequences containing Markers are amplified; (b) the Marker sequence (including SMID) is sequenced at the beginning of the Phase I reads, extending into the Marker-junction with the enzymatic fragmentation or sonication random break point. Phase II reports a read sequence from the second random break site produced by nebulization. Two internal sequences, therefore, are selectively reported in association with the SMID containing Marker, identifying their original source molecule. Tagging reagents differ in respect to their ability to report the sense of the source molecule strand. The Figure elements presented here describe the amplification reactions used with type I, type II-p and type II-t Markers.

Figure 6A:
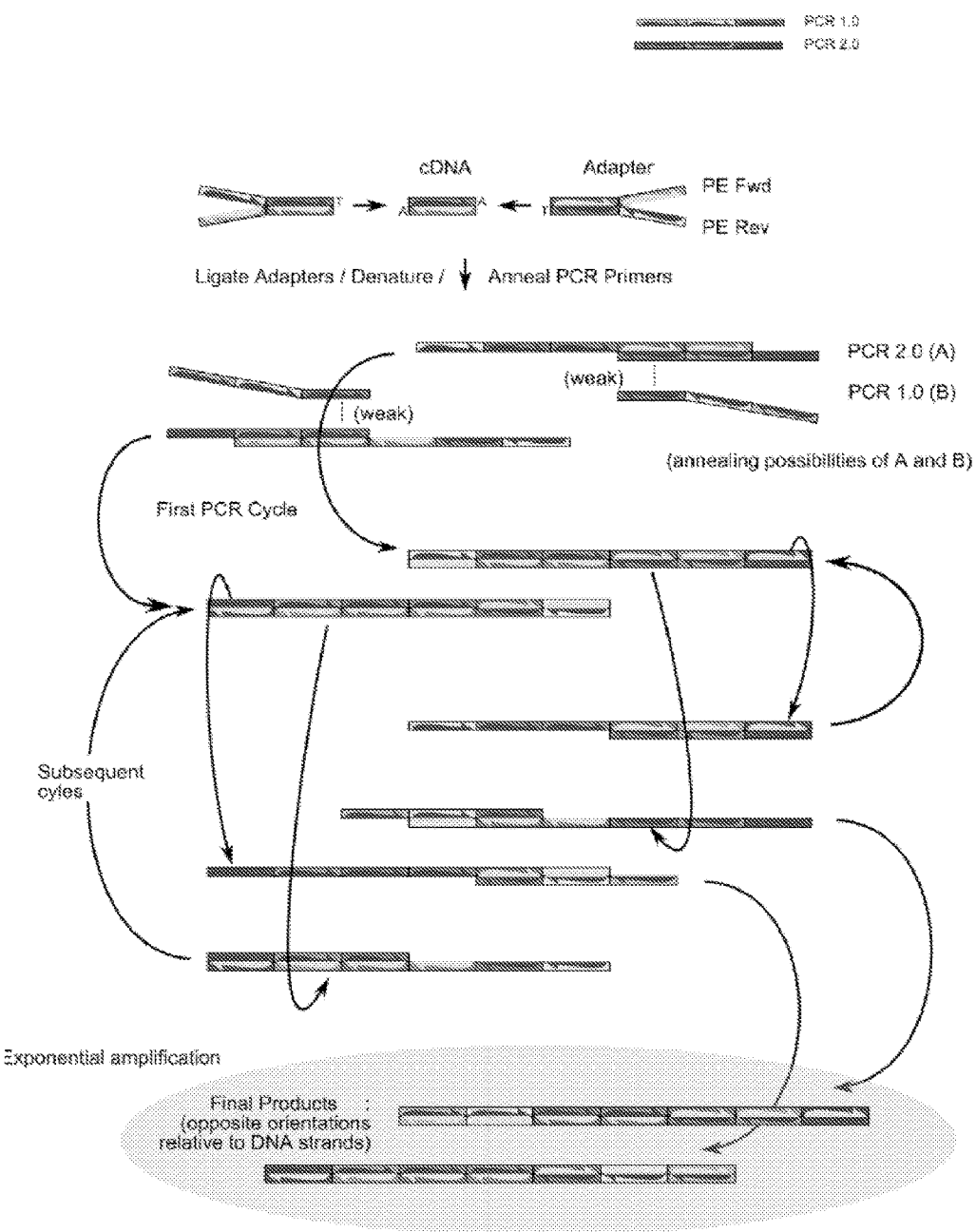
FIG. 6A schematically illustrates selective amplification of Marker-bearing fragments. A) In the standard protocol, captured junctions are A-tailed and ligated to Illumina forked adaptors (PCR Primer 1.0; PCR Primer 2.0) that allow for PCR amplification that increases the abundance of each fragment and simultaneously introduces unique paired ends containing, in addition to PCR primer sites, capture, cluster synthesis, A and B type restriction site sequences together with the sequencing primers.
Figure 6B:
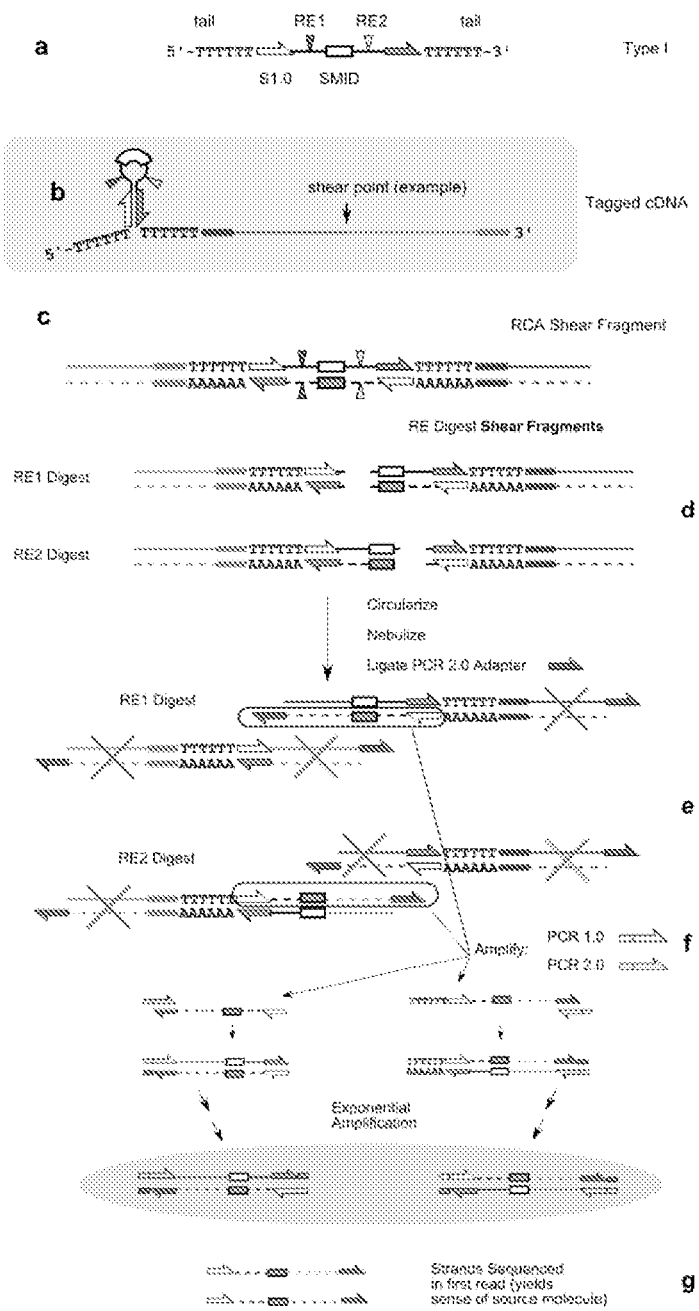

FIG. 6B. a) Type I Marker-Blocks possess two types of restriction sites on the 5' and 3' sides of the SMID. b) After cDNA synthesis and amplification, cDNAs are subjected to enzymatic fragmentation or random fragmentation by sonication; location of shear sites shown symbolically. c) Sample fragments are illustrated. d) Following enzymatic fragmentation or sonication, fragments are divided into aliquots, cleaved with one or the other of the restriction enzymes and recombined (modification of 5B). e) Fragments are end repaired, biotinylated, circularized, nebulized and junctional fragments captured on Streptavidin beads. They are then A-tailed and ligated at the 3' end to a modified adapter possessing only annealing sites for PCR Primer 2.0. f) Amplification is performed with Primer 1.0, which interacts with the complementary sequence in the Marker, and Primer 2.0, which anneals to the 3' adapter at the random-break point. The result of amplification is that only segments possessing a Marker on one end and a random break point on the other are represented in the final mate-pair Library. g) The first sequence reads of the mate-pair Library yield the Marker (wrapper and associated SMID sequences) and the sense of the source molecule strand.

Figure 6C:
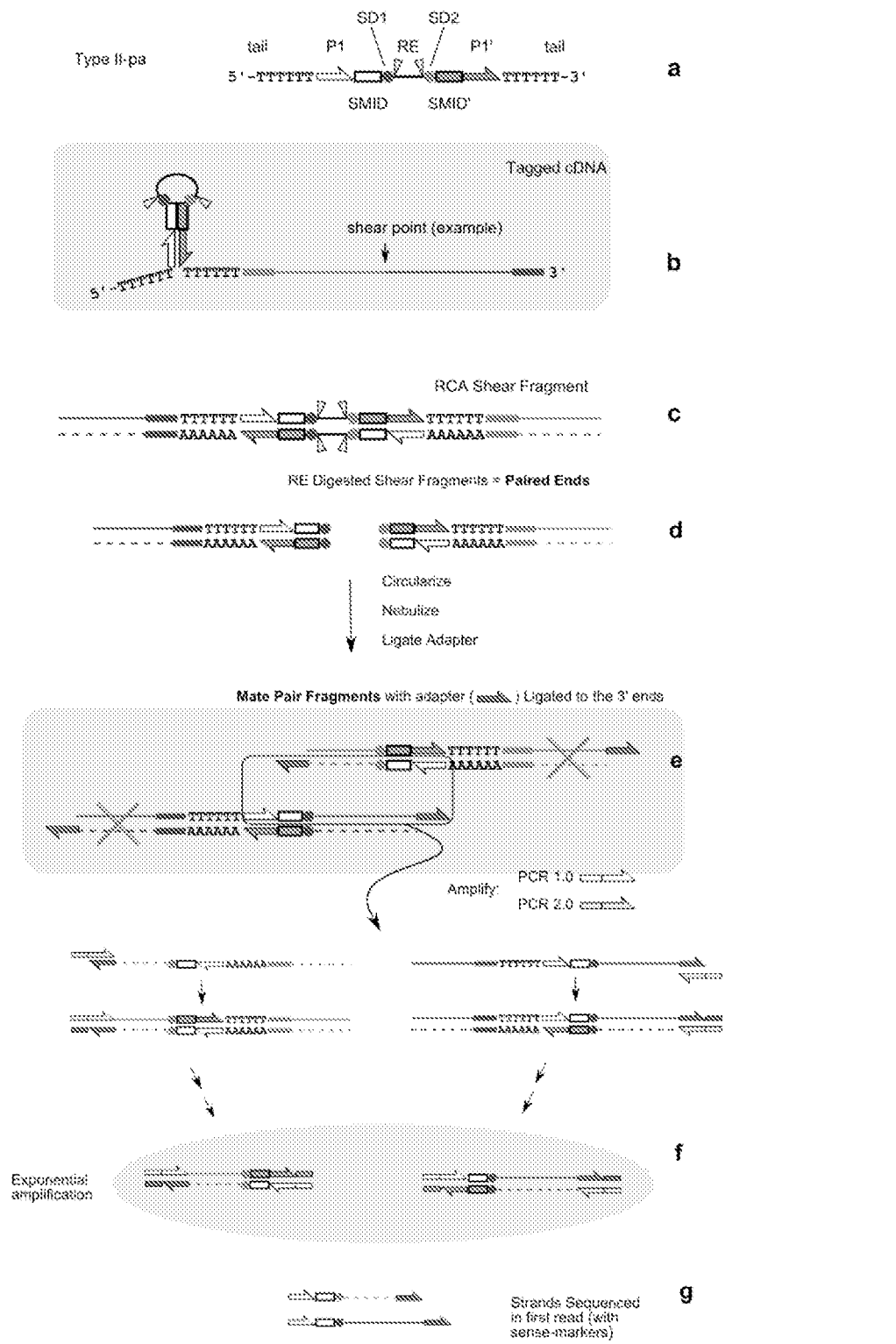

FIG. 6C. Type II-pa and type II-ps tagged cDNAs are processed in the same way; type II-pa processing is illustrated. a) Type II Marker-Blocks possess two copies of a rare restriction site in the loop between duplicate SMIDs, together with two sequences, that of PCR Primer 1.0 and its complement. b) cDNA is synthesized, amplified and fragmented (enzymatic fragmentation or sonication); random break sites shown symbolically. c) fragments shown schematically. d) the segment between SMIDs is removed by restriction enzyme cleavage. Fragments are end repaired, biotinylated, ligated into circles, nebulized and junctional fragments captured on Streptavidin beads. Circularization brings random or non-random break sites produced by enzymatic fragmentation or sonication into proximity of the SMID or SMID complement. e) Captured biotinylated junctional nebulization fragments are end-repaired, A tailed and ligated at the 3' end to a modified adapter complementary only to PCR Primer 2.0. f) PCR is performed with PCR Primer 1.0, or a modified version of this primer, that interacts with its complementary site in the Marker-Block, and with PCR Primer 2.0 that interacts with the random-break site associated adapter. g) The result of this amplification is (a) only Marker-bearing fragments comprise the mate-pair Library; (b) Marker sequences are selectively reported in the initial read, followed by an internal break sequence from the initial fragmentation (enzymatic fragmentation or sonication); (c) the mate-pair sequence derives from the second random beak site produced by nebulization. Essentially all read pairs from the mate-pair Library are indexed according to the source molecule from which they are derived. For type II-pa tagged molecules, the sense of the source molecule strand is indicated by the asymmetrical markers (circle symbols); for type II-ps tagged molecules, this information is not available.

Figure 6D:
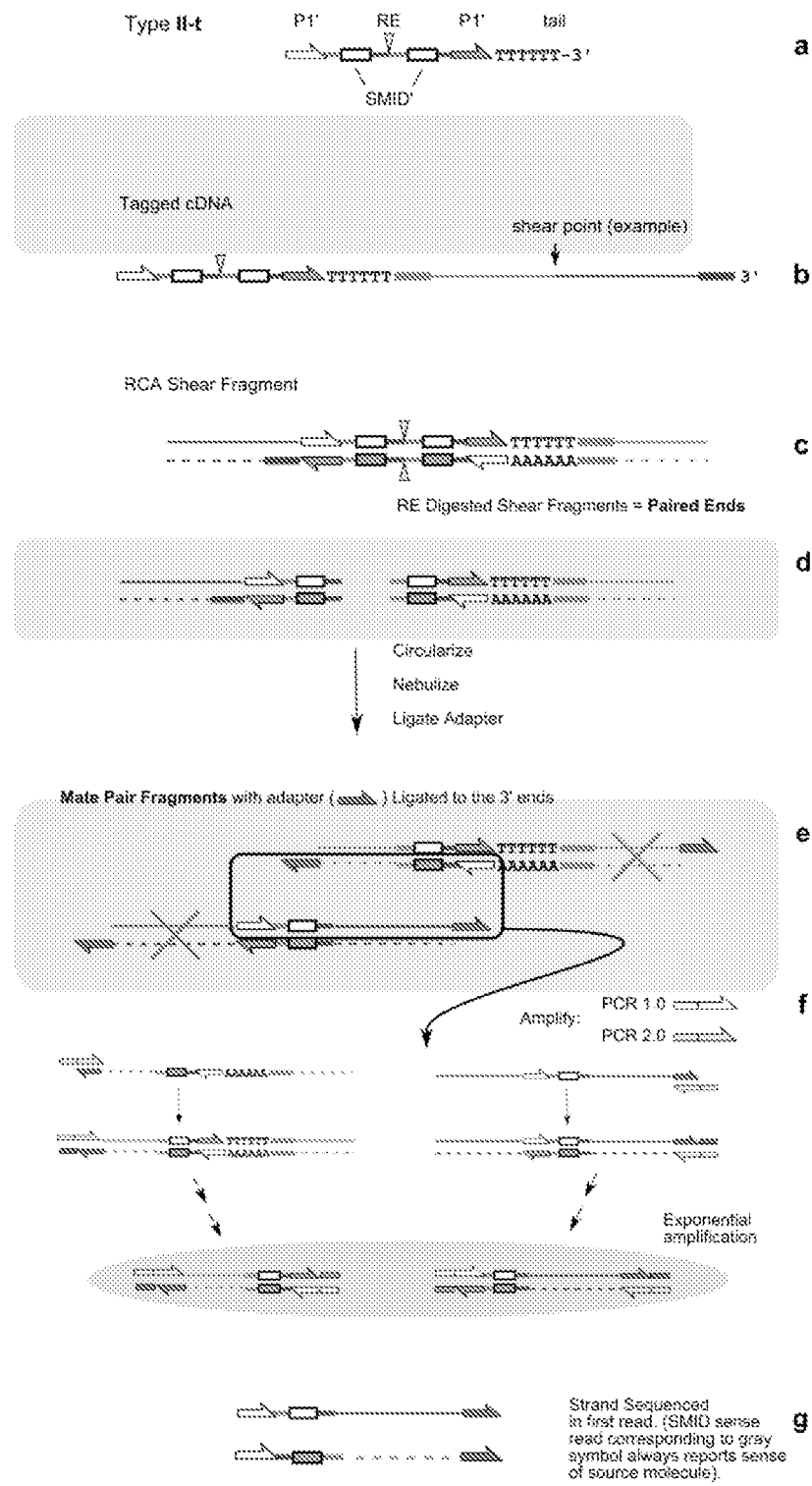

FIG. 6D. a-f) Library production is performed as for type II-p markers, but the fate of the SMID orientation is illustrated. g) The marker sequence (or its complement) is revealed in the first read, followed by a junction corresponding to the enzymatic fragmentation or sonication break site; the mate-pair sequence reveals the nebulization break site, as above. Each read pair may be reported as the sequenced read or its complement. Type II-t markers have the useful attribute that the complement of the tagging reagent Marker (distinguished by wrapper sequences and check bases) is uniquely associated with the sequence of the source molecule strand. Direct isolation of cDNA constructs: Type II reagents generate cDNAs flanked at both 3' and 5' ends with identical Marker sequences; full-length cDNAs from a specific source molecule can be thus be rescued directly from an aliquot saved from the enzymatic fragmentation or sonicated sample by Marker- (e.g. SMID)-directed PCR and subcloning.

Figure 7A:
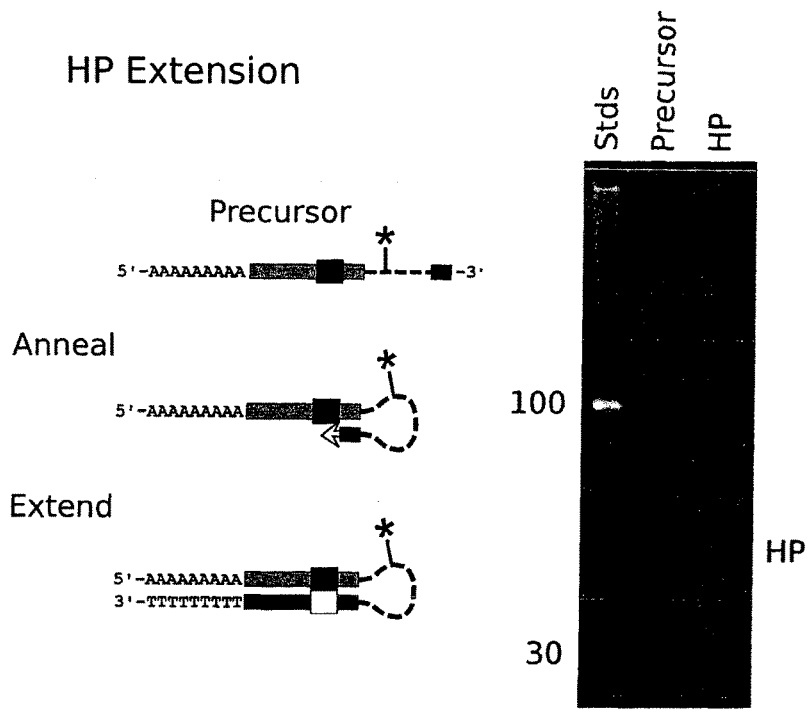
FIG. 7A). (2) Synthesis of 3Q from HP. This second reaction is also mediated by Phi 29 DNA polymerase. Loop primer anneals to the open loop of HP to prime a copy of the 5' portion of HP (1Q), freeing the 3' end as single stranded DNA to permit reaction (3). Loop primer is generally, but not without exception, non-phosphorylated at the 5' terminus. The 1Q-HP complex is designated 3Q. (3). TRS-HP complex. This reaction is performed simultaneously with reaction (2), mediated by the same enzyme. 2SP RNA Protector Primer is annealed to the 3' end of 3Q to protect the terminus from exonuclease activity of Phi 29 and to prime synthesis of an RNA chimeric TRS-HP duplex, with release of free 1Q from 3Q. Following inactivation of Phi 29, RNAse H removes the RNA moiety. This reaction is typically quantitative. (4) 1Q, reaction primers and enzymes may be removed by gel or other purification of TRS-HP. 1Q and excess reaction primers may be removed by 3'→5' exonuclease activity of Phi 29. (In the event 1Q is retained as a contaminant capable of priming cDNA synthesis, the resulting product will not circularize in subsequent reactions due to the absence of a 5' phosphoryl group.) Transient denaturation irreversibly separates the single stranded HP and TRS DNAs. Because of the strong internal complementarity, self-annealing quantitatively dominates re-association of the two strands, prohibiting reformation of the complex. As an equimolar by-product, HP is of no consequence, being inert either in respect to cDNA priming or circularization in library preparation. Reactions (2) and (3) are typically quantitative (c.f., FIG. 7B). Type II-pa/$HP_1$ or type II-ps/HP product reagents are pure and used directly to synthesize tagged cDNA.

FIG. 7A shows results of HP Extension (4% Agarose gel). Oligo-J precursor is extended with DNA polymerase Phi 29. The precursor band is light and diffuse due to (a) conformational equilibrium between clamped and extended forms and (b) poor binding of EthidiumBr by single stranded DNA. In contrast, after extension HP is evident as a bright band of higher apparent molecular weight owing to a more rigid double stranded configuration.

Figure 7B:
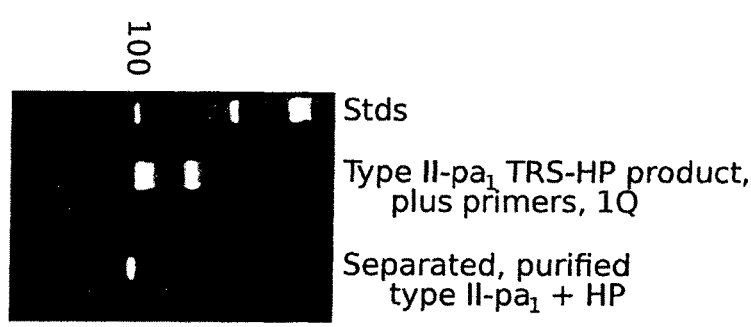

FIG. 7B shows results of synthesis of type II-$ps_1$ TRS (4% Agarose gel). After synthesis, gel purification and separation of strands, this material, produced in free solution (no solid phase) is an equimolar mix of separate TRS and HP. HP is inert in respect to priming cDNA synthesis or circularization prior to RCA: (after circularization, HP is eliminated by exonuclease I and II treatment following circularization). Conversion is typically quantitative.

Figure 7C:
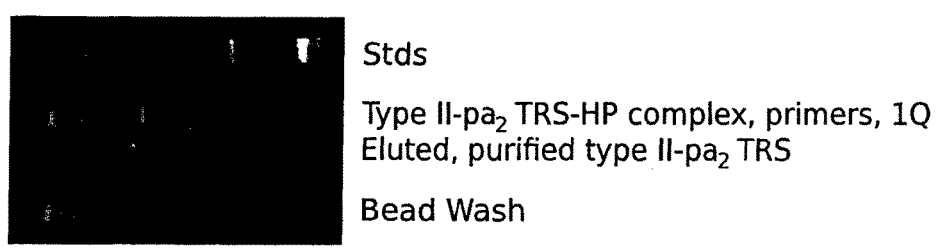

FIG. 7C shows results of synthesis of II-$ps_2$ (4% Agarose gel). Following HP-TRS synthesis, adsorption to Streptavidin beads and washing removes 1Q, reagent primers and enzyme; transient heating and denaturation frees pure TRS from the solid phase, with biotinylated HP retained on beads. This reaction is typically quantitative.

Figure 7D:
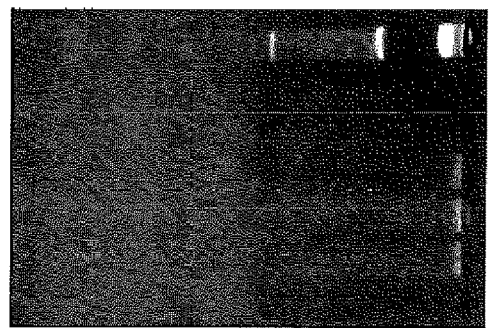

FIG. 7D shows results of cDNA synthesis primed by type I, type II-$ps_1$ and type II-$ps_2$ tagging reagents (4% Agarose gel). Poly-A mRNA from Human Embryonic Kidney (HEK-293) cells was reverse transcribed with a limited amount (0.25 pmol) of each of the tagging reagents. The large cDNAs are clustered at the top of the gel. Each cDNA band corresponds to a sufficient number of molecules (~150,000,000,000) to massively report the mRNA population present in the cells.

Figure 7E:
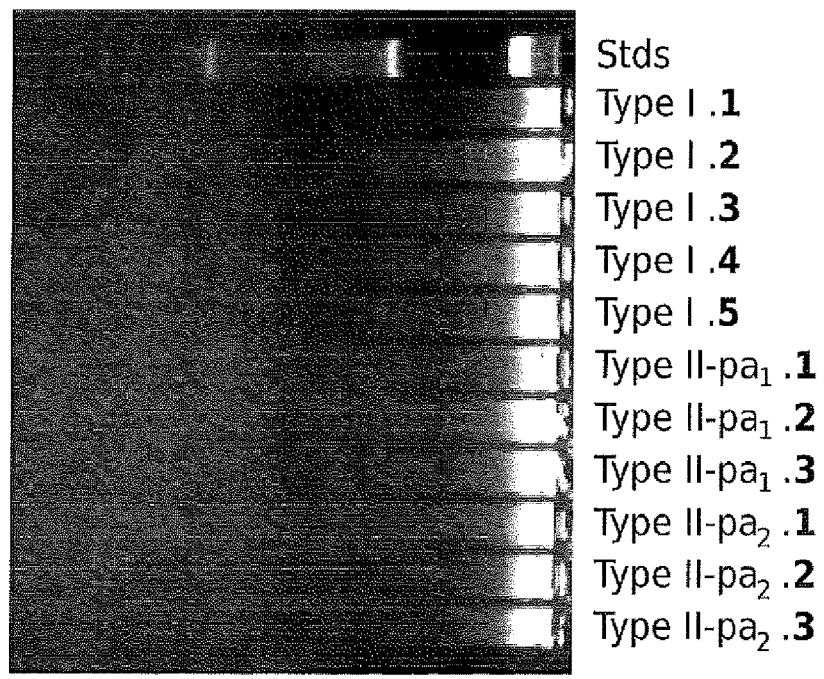

FIG. 7E shows results of RCA of circularized cDNAs from type I, type II-$ps_1$ and type II-$ps_2$ tagging reagents (4% Agarose gel). Small aliquots of cDNA produced as in (D) were subjected to RCA with thiophosphoryl random hexamers and Phi 29 DNA polymerase and a small aliquot run on the gel. The large concatemers are trapped at the top of the gels. These reactions are highly reproducible; each RCA reaction may be sufficient for the preparation of multiple libraries.

Figure 7F:
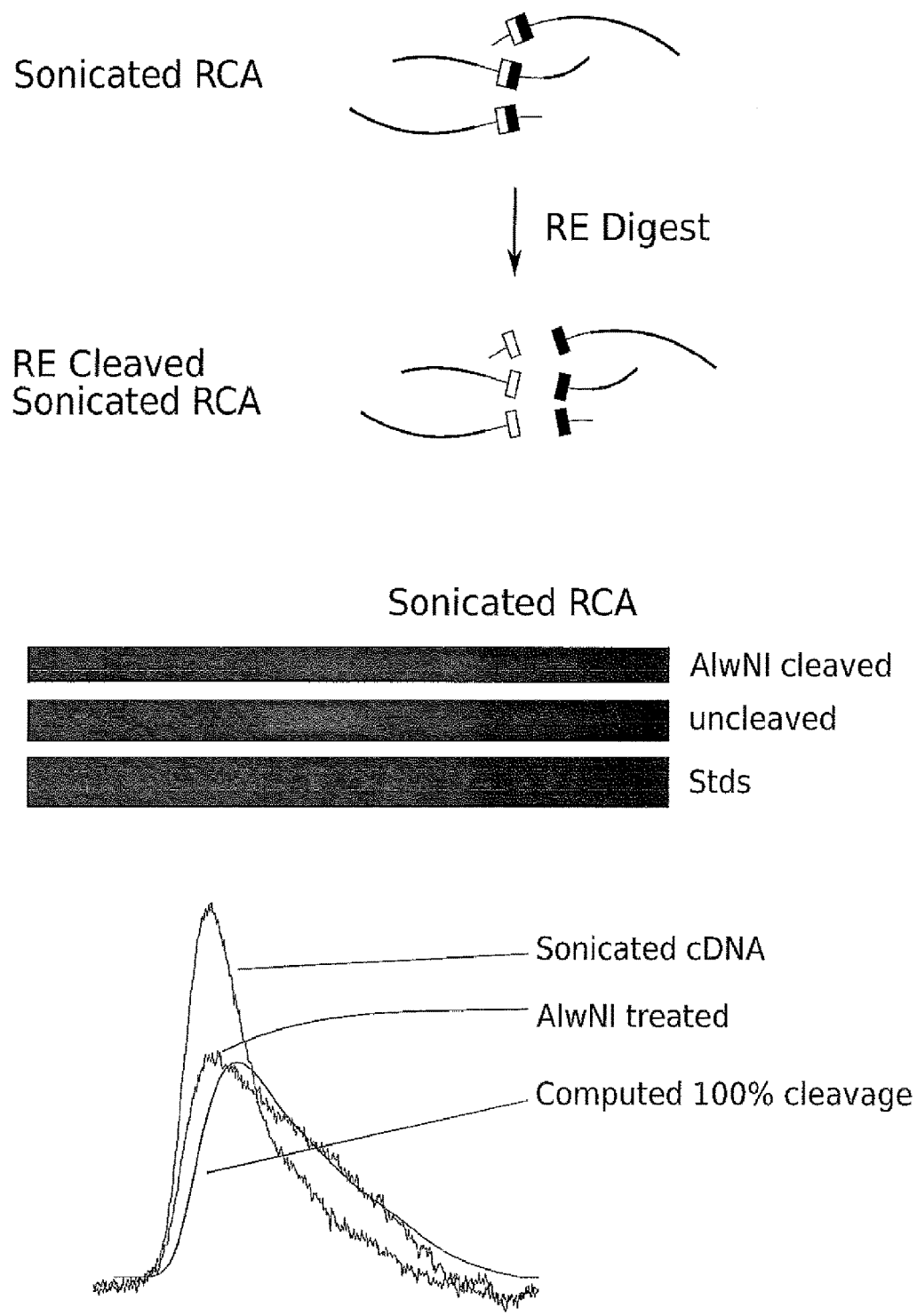

FIG. 7F shows results of enzymatic fragmentation or sonication and Restriction Enzyme Cleavage of Debranched RCA Products (1% Agarose gel). Homopolymers are initially undergo enzymatic fragmentation or sonicated to generate fragments averaging~4 kbp, run on the gel. A molecular weight shift is noted following cleavage with the rare restriction enzyme AlwN1 to remove the segment between duplicate Markers. The graph illustrates scans of the gels before and after enzyme treatment. The solid line predicts the size distribution for 100% cleavage; the small offset reflects the fact that the mathematical modeling does not estimate fragments that may lack an internal tag.

Figure 7G:
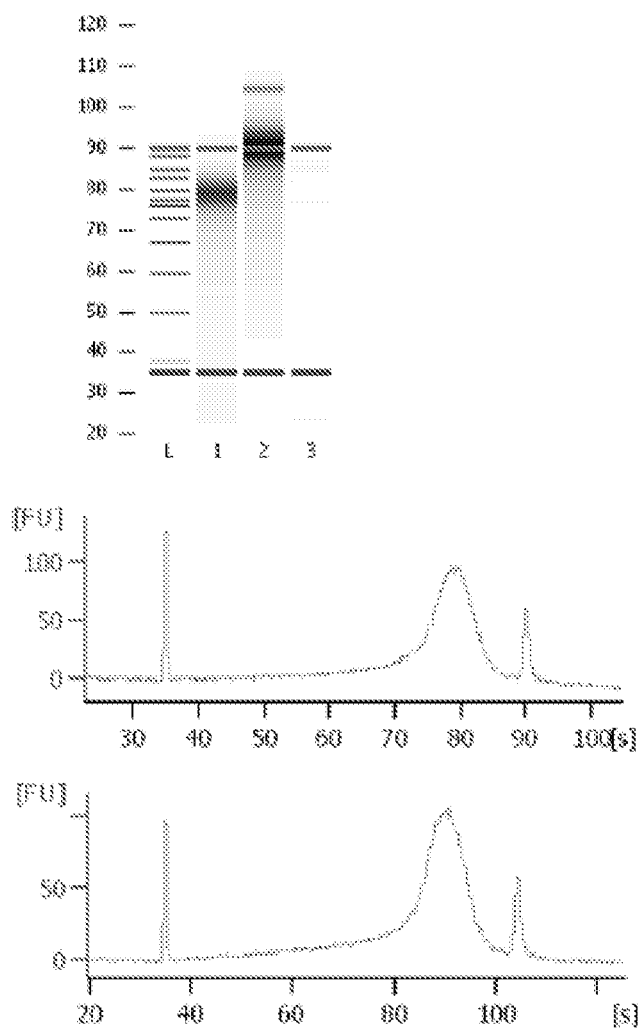

FIG. 7G shows results of replicate gels and gel scans of mate-pair Library generated with PCR amplification of junctional fragments (Agilent analytical gels). In this case, PCR was primed from a primer site within a type II-$ps_1$ tag and a terminal PCR 2.0 site in a terminal adapter ligated to the random break site. A sequencing run performed with this library using one of the 15 experimental chambers of the High Seq instrument yielded 174,000,000 read pairs.

FIG. 7H-7I show results of end-tagged read pairs generated by High Seq sequencing of the above end-tagged mate-pair library. (1) Examples of mate-pair reads from end-tagged sequences picked at random are displayed; Markers are highlighted for 5' and 3' wrappers and check bases in read I. Corresponding read II sequences are shown below. A sequencing error in a check base is shown in red. SEQ ID NOs: 7 (Marker Motif: 5'wrapper-SMD-3'wrapper), 8 (read I) and 9 (read II) are shown in these figures.

These data demonstrate that steps of the protocol achieve their desired ends, specifically: (a) tagging reagent synthesis succeeded in generating Markers of the intended sequences and diversity carried through to the mate-pair library; (b) cDNA synthesis tagged individual mRNAs from the tissue sample (cultured Human Embryonic Kidney (HEK 293) cells)—a survey of 30,000 read pairs identified more than 4,000 genes expressed in the cells); (c) cleavage of the di-tagged type II-$pa_1$ reagent used was efficient; (d) the reactions brought together the unique SMID for the source molecule with internal cDNA sequences; (e) the modification of the Illumina mate-pair protocol produced an end-tagged mate-pair library, facilitating identification of the Marker sequences; (f) mate-pair sequences match with a high efficiency and fidelity the products of known genes and not intergenic DNA sequences; (g) data may be sorted according to source molecules identified with unique SMIDs. (2) mate-pair matches from blast searches Example I. In this example, mRNA from the gene for *Homo sapiens* aldehyde dehydrogenase was tagged. Because sequenced fragments are amplified from within the Marker sequence, which on average will in the middle of the nebulized fragment, the 163 bases of cDNA sequence (63 from read I, 100 from read II) often overlap in this library which was generated with 300-400 bp nebulization fragments. This overlap is indicated by highlighted query sequences. (3) mate-pair matches from blast searches Example II. In this second example, in which mRNA for the gene for *Homo sapiens* brain my047 protein was tagged, a comparable degree of overlap is observed. Although use of somewhat larger products of nebulization used in PCR amplification may increase useable sequence, some overlap is desirable to control for decreasing fidelity in calling bases at the end of long sequencing cycles (here 100 bp).

Figure 8A:
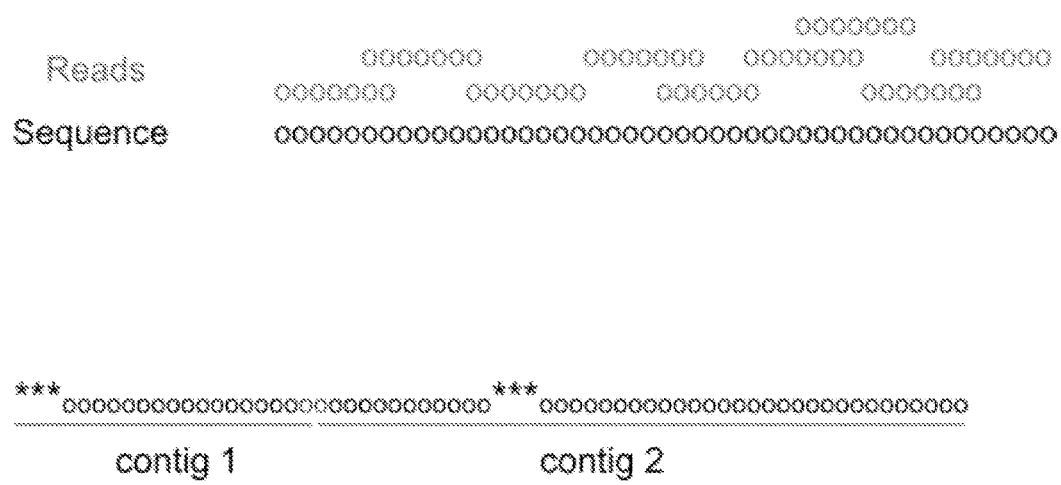

FIG. 8A schematically illustrates the assembly of sequence-reads into overlapping contigs, and a template covered by two contigs, a minimum that will assure that of a template comprising three tandem cDNA sequences can be constructed without gaps.

Figure 8B:
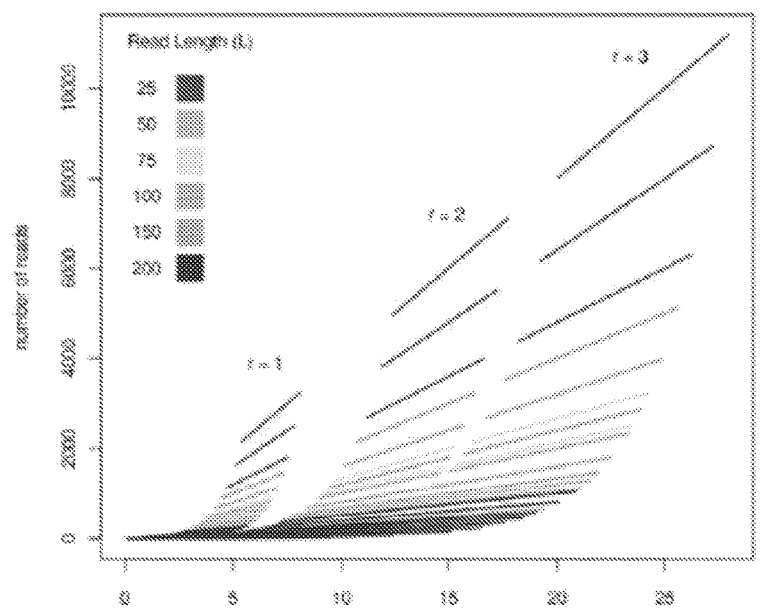

FIG. 8B is graphical representation that plots the number of reads versus coverage for the parameters computed. This shows overall behavior. Each line segment connects points for five values of k (1, 2, 3, 5, and 10) contigs per total sequence—including repeats) for one transcript length (T), one transcript repeat value (r), and one read length (L). The three repeat levels (r) segregate the plot into three groups: (r=1), (r=2) and (r=3). This shows how coverage of a single transcript increases if the transcript is copied in tandem but covered by a fixed number of contigs. The larger transcripts are on top, as more reads are required to cover them.

Figures 8C, 8D:
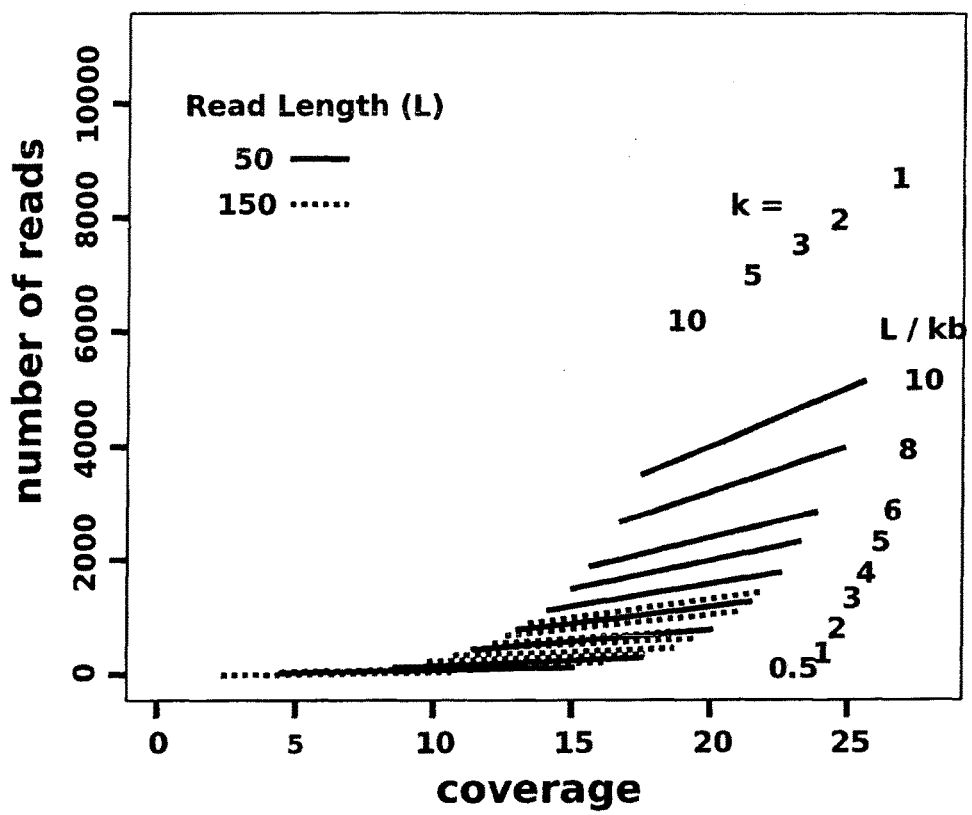

FIG. 8C is a graphical representation that plots a subset of the data to demonstrate the effects of read length on the total coverage to capture the entire transcript sequence. The red curves plot values for nine transcript lengths with 5 contig values each at fixed read length (50 bp) and repeat number (3). The blue curves are the same, but with a longer read-length (150 bp). Longer transcripts require reading 3.5 to 4-fold more bases with 50 bp reads than with 150 bp reads for the same level of assurance of covering the transcript.

FIG. 8D is a table relating read length, transcript length, coverage, and read number. This abridged table of the relationships of the number of reads for particular depth of coverage on read-length, the number of contigs per read length, repeat levels and transcript length allows estimates of the relationship between mate-pair read number generated in an experiment and the number of cDNAs of a given size that will be fully sequenced with a particular depth of coverage.

Figure 9:
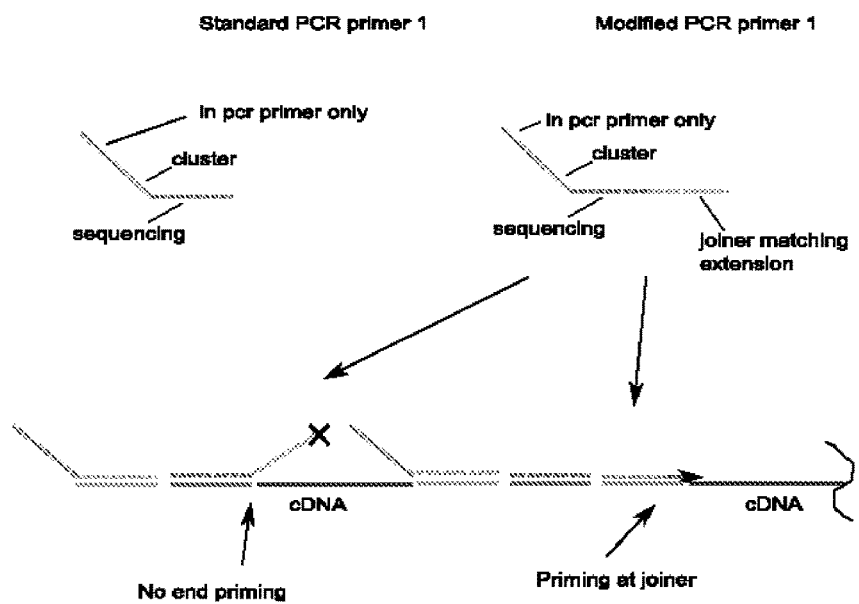

FIG. 9 illustrates an embodiment of a modified primer. Improvement in yield of mate-pair sequences containing the SMID can be obtained by using a primer directed against the tag (joiner) in the PCR step of library production. This further insures the SMID sequence will be about the end of essentially every library fragment so that one of the pair of reads will yield the SMID in the tag sequence. Therefore, one substitutes the modified primer for the A primer of the Illumina reagent in the standard mate-pair or end-pair protocol.

Figure 10:
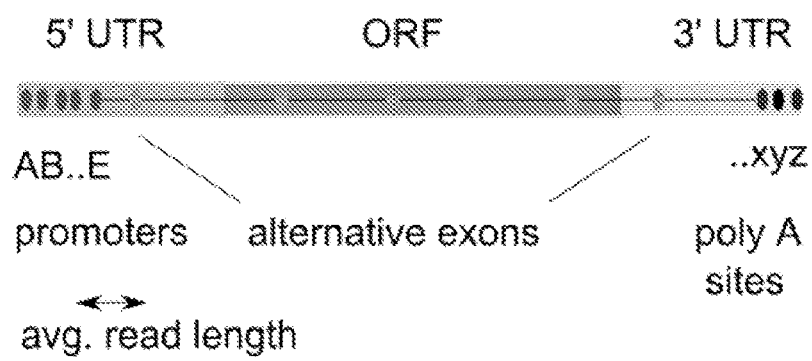

FIG. 10 illustrates alternative transcriptomes that might arise from a hypothetical gene subject to variations in 5' and 3' UTR due to use of alternative promoters and alternative consensus sites of RNA chain termination and polyadenylation, and variations in both UTR and ORF due to alternative RNA splicing Symbols A-E denote variable 3' UTR segments associated with alternative promoters; x-z reflect different 3' UTR segments associated with alternative termination and polyadenylation sites; green symbols represent alternatively spliced exons, whose retention or deletion is signified by the presence of 1 or 0 in the matrices of variants within parentheses. The dotted lines signify the hypothetical ORF.

Figure 11A:
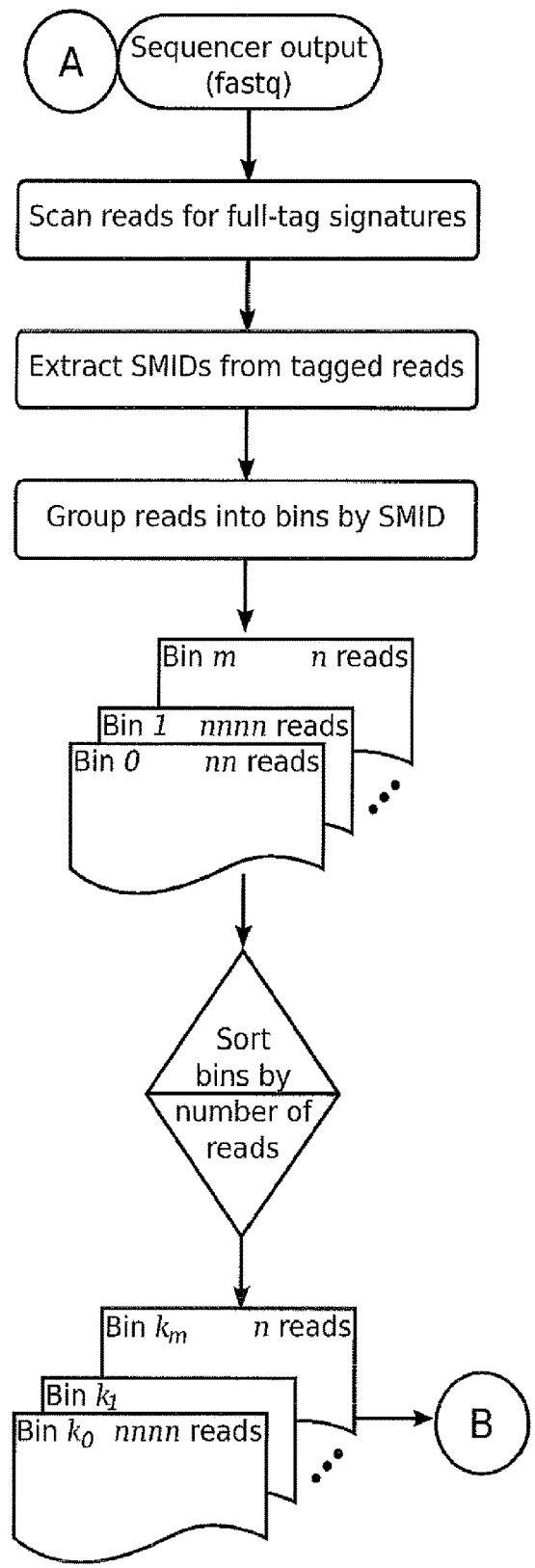
Figure 11B:
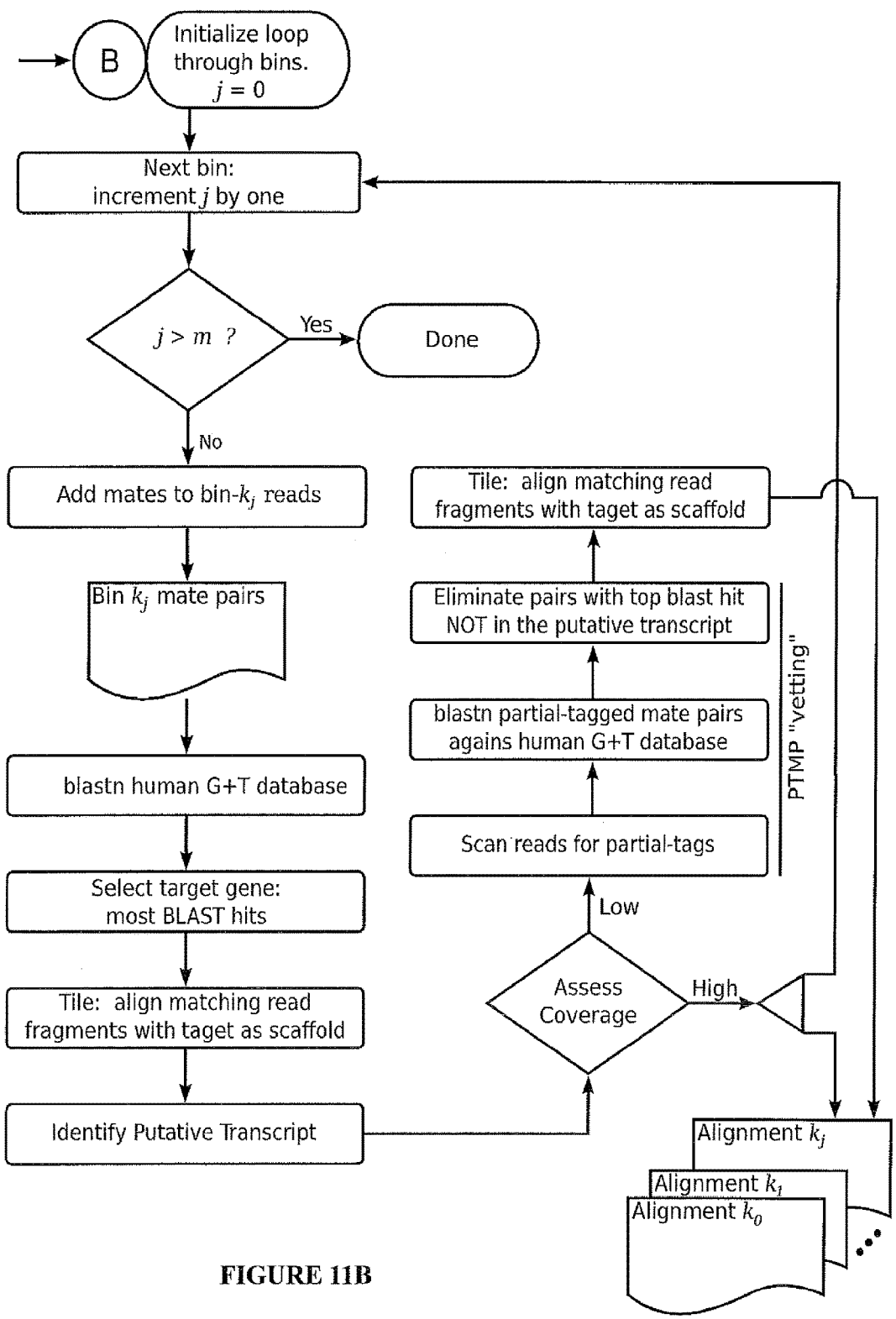

FIGS. 11A and 11B show flow charts for computational analysis of data returned from a sequencing run. G+T symbolizes genomic and transcript databases; PTMP signifies partially tagged Mate Pairs which may arise from library fragments possessing broken or otherwise partially sequenced SMIDs, or SMIDs with a small number of PCR or sequencing errors, whose identification can be shown to exceed a specified probability threshold (viz p<10-9) based on both SMID sequence and association with a particular gene transcript.

Figure 12:
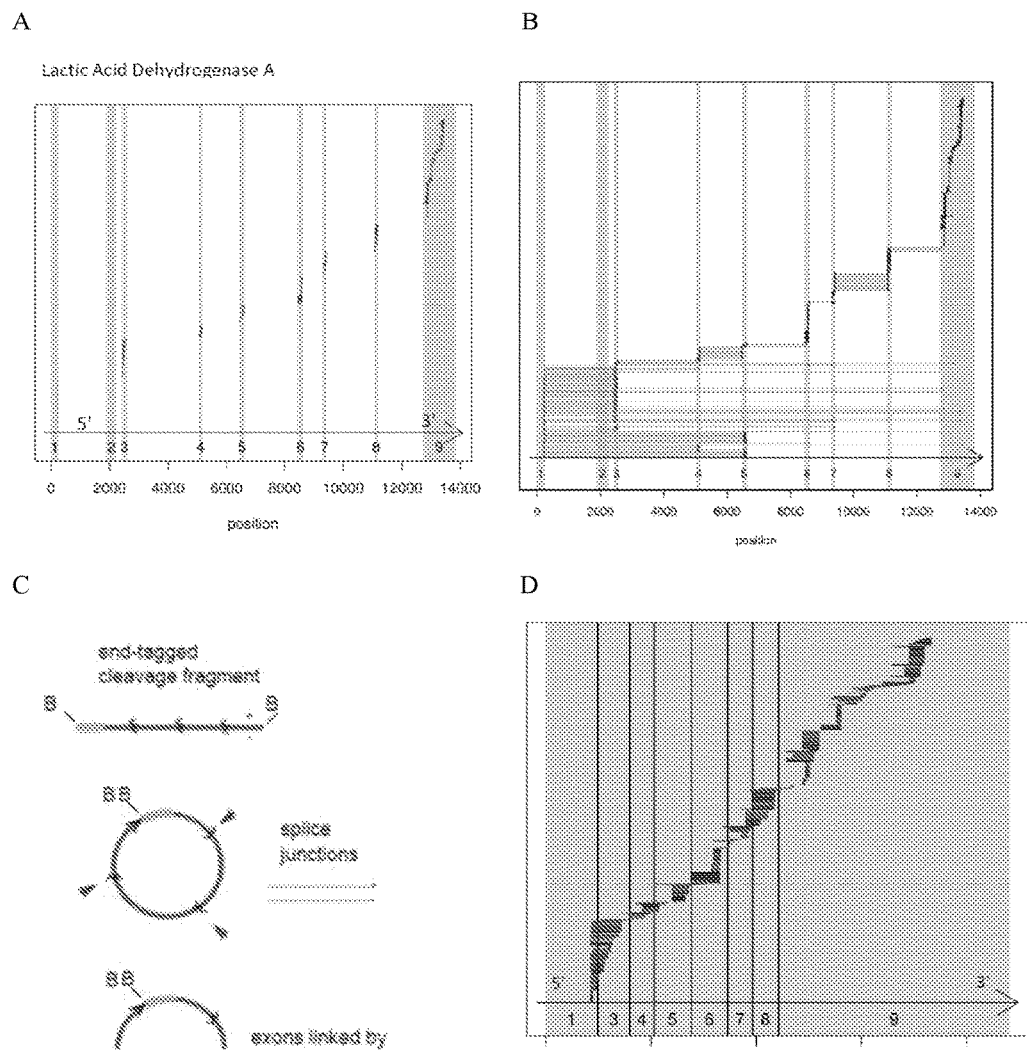

FIG. 12 shows illustrates a full-length messenger RNA sequenced in a prototype experiment from tagged cDNA homopolymers prepared from human embryonic kidney cell lines and analyzed by Illumina HiSeq 2000 Mate Pair sequencing (Nature. 2008 456(7218): 53-59). Panel A illustrates the total sequence of the Lactic Acid Dehydrogenase A gene tiled with mate-pair reads, each labeled with a replica of a SMID incorporated into a primary cDNA molecule by reverse transcription; RefSeq annotated exon boundaries are denoted; end sequences were validated by inspection. Panel B illustrates connectivity of reads. Thin horizontal lines connect segments to a single read that match disjoint segments of the chromosome. In many cases, the intervening genomic sequence is an intron that has been spliced out, and the two flanking pieces are actually a continuous sequence in the read. In other cases the connected sequences are actually separated within the read; these arise from distant cDNA sequences brought together in the mate-pair library preparation. The two kinds of linkages are illustrated in panel C. Panel D illustrates alignment of the same reads over the deduced messenger RNA (which lacks exon 2) showing coverage of all intramolecular splice junctions. Throughout, colors pertain to the sense of the messenger RNA reported in the sequenced Mate Pair.

SEQUENCE LISTING

The Sequence Listing is submitted as an ASCII text file [6975-95588-11_Sequence_Listing.txt, Oct. 27, 2015, 13.0 KB], which is incorporated by reference herein.

DETAILED DESCRIPTION

The methods described herein overcome certain limitations of RNASeq. The limitations of RNA-Seq, as well as whole genome sequencing or 'exome sequencing' strategies to predict or explain cell and tissue phenotypes is captured the schematic depicted in FIG. 10 of two alternative transcriptomes that could arise from a single hypothetical interrupted gene. It is evident that, even quantifying expression frequencies of individual alternatively spliced segments (here identical in the two transcriptomes), exome sequencing cannot distinguish scenarios in which totally different proteins are expressed—distinct structural contexts in which disease mutations may affect function.

One can define the information that tends to be missed in RNA-Seq and generic exome sequencing strategies: consider an array of alternative RNAs arising in a complex tissue from a hypothetical gene g, with multiple UTR's derived from alternative 5' sites of transcription activation and 3' consensus polyadenylation sites, and both UTR and ORF segments subject to alternative RNA splicing, (or RNA editing). Assume the variants in a comprehensive survey comprise linear combinations of n variable segments ('exons,' broadly defined), in order 5' to 3' on the chromosome, $X=(e_1, e_2, \ldots, e_n)$. The sequence of the $i^{th}$ messenger variant, $s_i$ is specified by $s_i = (a_{i1}e_1 + a_{i2}e_2 \ldots a_{ij}e_j + \ldots a_{in}e_n)$ where $a_{ij}$ is a retention coefficient which is 0 or 1 when the exon $e_1$ is deleted or retained, respectively, or more simply $$s_i = a_{ig} \cdot X_g$$

where $a_{ig}$ is the vector of retention coefficients for the $i^{th}$ message of gene g and $X_g$ refers to the set of retained exons of g.

Recognizing that even a large survey of splice variants may be incomplete—e.g., that unexamined cell types may introduce additional variations in $X_g$, this term is replaced by the genomic sequence within the gene boundaries, written in a different fashion (symbolized by $\Psi_g$). $\Psi_g$ signifies a matrix like $X_g$, but comprising all conceivable contiguous segments from all ordered bases within the gene boundaries that might lie between splicing acceptor and donor sites. Thus, $$s_i = a_{ig} \times \Psi_g$$

This relationship formally segregates information in the messenger code that derives from the genome sequence of g (embodied in $\Psi_g$) from cellular instructions ($a_{ig}$) arising from highly regulated RNA processing in the cell in which the variant is expressed (sometimes called the 'interactome'). Both informational contributions specify the structure and molecular properties of proteins; they must be subject to variation and natural selection. A protein coding gene may evolve in multiple directions simultaneously to produce proteins mediating different biological processes.

The transcriptome, $\tau$, is sometimes taken as the distribution of relative gene expression levels: $\tau = (p_1, \ldots, p_g, \ldots, p_N)$, where N is the number of genes; $p_g = n_g / \Sigma_{g=1}^N n_g$; and $n_g$ is the total number of message molecules for all variants of gene g.

In turn, each gene has its own transcriptome, $\tau_g = (q_{g1}, \ldots, q_{gk})$ where k is the number of message variants of gene g; $q_{gi} = n_{gi} / \Sigma_{i=1}^k n_{gi}$; and $n_{gi}$ is the number of message molecules for variant i. Absorbing actual gene sequence elements into $\tau_g$ reconstitutes the transcriptome as a weighted inventory of variant sequences, e.g the form of information usually desired. In this rendering, $$\tau = \sum_{g=1}^N p_g \left( \sum_{i=1}^{k_g} q_{gi} \cdot (a_{ig} \cdot \Psi_g) \right) = \sum_{g=1}^N p_g \cdot \tau_g.$$

RNASeq, optimally performed, captures all information expressed from $\Psi_g$ and some individual splice junctions, but not longer range linkages. RNASeq generally employs complex statistical algorithms to predict most likely expressed variants, but cannot capture $a_{ig}$ experimentally; it is, a computationally intensive, uncertain strategy, whereas direct sequencing provides a 'ground truth' dataset against which RNASeq algorithms must in any case be validated. Similarly genome sequencing of 'the' exome, by design, omits information that specifies $a_{ig}$, and thus cannot determine explicitly which proteins (or functional RNAs) may be expressed in cells or tissues. The technology disclosed here is designed specifically to capture the intramolecular linkage information and relative variant distributions required to describe the transcriptome.

The challenge for large scale cDNA sequencing, as demonstrated in the previous description, is intrinsically linked to the biology of genes of higher species and their differences from the classical cistronic gene model. The scale of the disparity is easily inferred: viz, the bacterium *Escherischia coli*, a single celled organism of roughly the dimensions of a mitochondrion and limited phenotypic diversity, possesses (varying with strain)~4,700 cistronic protein and functional RNA coding genes. By contrast, the fertilized human ovum, with only slightly more than 4 times as many 'interrupted genes,' gives rise to 100 trillion cells, each vastly more complex than a bacterium, to form the tissues, organs and organ systems (including the 100 billion neurons and 100 trillion synapses of the human brain). The informational non-equivalence of cistronic and 'interrupted' genes is evident.

In a typical embodiment of this disclosure, every mRNA is labeled at the time of reverse transcription with a unique tagging reagent containing a copy or copies of a source molecule identifier (SMID). Following reverse transcription, the full-length, tagged cDNAs are subjected to a series of steps that yield a library of overlapping fragments in which each fragment bears a copy of the original SMID. Alignment comparisons against curated gene sequences can identify new and confirm previously annotated exons.

This library may be sequenced with any of several existing shotgun sequencing platforms to yield both the label for the specific source molecule and a random sequence derived from that molecule. Sequence pairs are then segregated into groups ('bins') specific for each source cDNA molecule, followed by assembly of the full-length, end-to-end sequence of that cDNA.

Typically, the methods allow complete sequencing, at a predetermined level of coverage (e.g., 5×, 10×, 25×, etc.) of every molecule in the sample: the accuracy resulting from higher depth of coverage permits detection of single base mutations, single nucleotide polymorphisms (SNPs), or sites of RNA editing. The distribution of unique identifiers allows the reconstruction of the structure of the original mRNA population. Complete sequences, including 5' untranslated regions (UTRs), open reading frames (ORFs), and 3' UTRs are generated, including silent or missense mutations. This can permit correlation of control of transcription activation and post-transcriptional assembly of sequence elements. Intermediate steps in the protocol preserve full-length samples of the original cDNA pool that may be used to immediately clone copies of any particular source mRNAs detected by sequencing. Such clones can be characterized by heterologous expression, or used to prepare molecular probes. Library construction can be performed as to allow the simultaneous profiling of multiple transcriptomes from various tissue sources. Thus, mRNAs from multiple tumors from the same patient, or from different stages of development, or disease progression, can be processed in the same experiment, with the data to be sorted after sequencing (multiplexing).

Beyond sequencing mRNAs, and the resulting applications for basic and clinical research, the technology described herein has other potential uses: sequencing heterogeneous genomes of retroviruses evolving during the course of disease progression in a patient; monitoring the recombination of human and animal virus elements in animal reservoirs, as underlies the generation of variations of influenza; analyzing the dynamics of gene swapping associated with drug resistance or toxin-production, in microbe populations in animals subject to prophylactic antibiotic treatment, or microbes arising in agricultural crops subjected to soil ecology-changing pesticide regimes.

A contemplated application lies in the emerging area of personalized medicine. Certain therapeutic products affect people differently. Personalized medicine seeks to use genetic information about an individual patient both to predict or explain occurrence of disease and to select or optimize a therapeutic strategy. Although there are significant successes with this approach, in the vast majority of cases, the promise of personalized medicine remains unfulfilled. Even in the best circumstances outcomes will significantly benefit from more knowledge of the cell or tissue molecular phenotype, illuminated with several examples.

In breast cancer treatment, histological examination of a tumor specimen for HER2/neu, a tyrosine kinase involved in signal transduction pathways and cell proliferation, may point toward the use of trastumaab (Herceptin), a recombinant humanized monoclonal antibody directed to the HER2/neu extracellular domain. Successful treatment down-regulates HER2/neu expression as the proximate cause of cell proliferation, and may trigger immune killing of the cancer cells. Unfortunately in the majority of patients primary and acquired resistance to trastuzumab occurs; damaging off target effects on heart tissues may preclude its use in otherwise suitable patients with histories of coronary disease. In addition, in triple negative breast cancer patients, none of three cellular markers, HER2/neu, ER (estrogen receptor) and PR (progersterone receptor) are expressed: these cancers are typically more aggressive, more often diagnosed in younger women and African-American women, and lack either good diagnostic markers or therapeutic drug targets. Comprehensive cDNA profiling will likely offer insights into disease mechanisms, new diagnostic markers and possible therapeutic drug targets.

In certain embodiments, the disclosure relates to methods for cancer genome sequencing. In certain embodiments, the disclosure relates to methods of comparing specific genomes with parallel analyses of mRNAs of tumors and normal control cells to detect mutant proteins, activated gene cascades and other markers that account for the cancer phenotype such as those properties that specify a cell lineage is 'melanoma,' against a background of variations due to randomly accumulated passenger mutations. Identifying unique proteins of the cancer would provide targets for drug or immuno-suppressing therapies.

In certain embodiments, the disclosure relates to methods for immune system engineering. In dramatic pilot studies the immune systems of three patients afflicted with chronic lymphocytic anemia were re-engineered to attack a marker protein, CD19, expressed on normal and malignant immune (3-cells. N Engl J Med (2011); 365:725-733. In two cases this resulted in an autoimmune attack that eliminated signs of the disease; in a third, marked improvement was noted. Unfortunately, in similar studies directed against solid tumor cancers, serious and in several cases lethal off-target reactions damaged other vital organs that shared surface markers with the tumors because the average human cell expresses products of 25-30% of the protein coding gene complement. Learning more about specific protein variants expressed in vital tissues may guide the necessary refinement in target selection.

In certain embodiments, the disclosure relates to methods for selective drug therapies. Considerable attention has been devoted to selective modulation of receptors and enzymes. See Journal of Clinical Oncology, (2007) 1 25, 5815-5824. Most attention has been directed at characterizing the relative levels of co-activators and co-inhibitors present in target tissues. Comparatively little consideration has been given to the possibility that tissue-specific expression of the roughly two dozen splice variants of these receptors, or comparable variations in progesterone and androgen receptors, explain these differences. mRNA profiling using embodiments disclosed herein can capture information relevant to all of these possibilities.

Similarly kinases are effective pharmacological targets for a wide variety of conditions; in particular serine/threonine kinases appear to be at the root of numerous forms of cancer. Recently 518 genes were classified as members of the human protein kinase gene superfamily. See Science, 2002, 298(5600): 1912-34. Many of these may play distinct physiological roles in different tissues, in health and disease. The possibility that these may be in whole or in part pharmacologically distinguishable, could enable refinement of drug alternatives to identify compounds with minimal off-target effects.

In certain embodiments, the disclosure relates to methods for evaluating progressive diseases. Comprehensive analyses of cellular changes associated with a wide spectrum of progressive diseases are being widely pursued. Candidate disorders include Alzheimer's disease, Amyotrophic Lateral Sclerosis (ALS), Parkinson's disease, Multiple Sclerosis and congestive heart failure. Numerous genes have been detected in which mutations appear to alter mitochondria, synaptic function, broad control of alternative RNA splicing, and also generally, the turnover of protein mediated by the ubiquitin system. See Nature (2011) 477, 211-215. It appears that misregulation of some of these elements occurs even in the absence of identified mutations; phenotypic profiling may provide more over-arching indications of changes in gene activation and, at the same time, provide an inventory of mutations and/or splice variations associated with the disease progression.

In certain embodiments, the disclosure relates to methods for evaluating infectious diseases transcriptome analyses can reveal evidence for these infectious agents in an accelerated time frame.

Directing mRNA profiling at the immune system, in particular to survey immunoglobulins disproportionately up-regulated in a mature, successful response to an infectious agent, could allow direct cloning of human immunoglobulins, akin to monoclonal antibodies, that might be expressed as bio-engineered vaccines. Advanced rabies, for instance, progresses too rapidly for the immune system to catch-up, with generally high morbidity. This technology could augment the commercial development of monoclonal antibodies, often encumbered by the need to humanize mouse immune-globulins to overcome their own intrinsic immunogenicity.

An economically important area of clinical research concerns the use of Small Interfering RNAs (or siRNAs). These may be introduced as therapeutic agents to selectively degrade or prevent translation of specific mRNAs. Despite enormous advances in gene-specific targeting, and some successes in clinical regimens, a confounding problem has been an inability to evaluate target specificity. Unwanted gene suppression is often a side effect. The ability to profile the entire array of mRNAs in a target tissue before and after siRNAs expression constitutes a useful tool in advancing siRNA based therapeutic.

In certain embodiments, methods disclosed herein allow large numbers of cDNAs to be sequenced end-to-end and quantified in a single experiment, at minimal expense by an individual investigator: ($10^4$, $10^5$, $10^6$, $10^8$ cDNAs per experiment).

An especially powerful application lies in the full-length deep sequencing of mRNAs produced by the activation of transcription and post-transcriptional RNA processing in the course of expression of complex, interrupted genes of higher multi-cellular species. This captures a gain of information arising in the biochemical conduit between genome and proteome. This application is in support of the premise that molecular phenotype is more nearly specified by the proteins and functional RNAs expressed than by the genes activated for transcription.

Transcriptomics

While, in certain embodiments, this disclosure may be used for sequencing and de-novo assembly of any long polymer, like chromosomal DNA, described in this section is an application to transcriptomics. This embodiment allows comprehensive full-length sequencing and quantification of relative abundance of mRNA variants from the mixed population of messages in a cell or tissue transcriptome.

In this embodiment, the disclosure bypasses the ordinary step of cloning a cDNA replica of each full-length mRNA instead it allows the segregation according to molecular source ('virtual cloning') of sequence information after random, massively parallel sequencing of up to billions of cDNA fragments derived from a heterogeneous mixture of cDNAs, including forms that differ only in patterns of linkage of common sequence elements distributed over lengths greater than any individual sequence read.

The disclosure provides a combination of reagents, steps and procedures that enable a number of different DNA sequencing technology platforms to be used for sequencing and quantifying the profile of mRNAs from a cell or tissue ('transcriptome').

In certain embodiments, the methods typically encompass the following steps:

1) attaching a unique identifier sequence 'tag' to each polynucleotide in the mixture;

2) replicating the tagged polynucleotides, typically (but not necessarily) as tandem, tagged homopolymers;

3) shearing, e.g., physically, the tagged replicated products to break the cDNA replicas at random points;

4) cleaving enzymatically at a defined site within the identifying tag to position the identifier on one end of each enzyme cleavage product;

5) sequence every tagged fragment to capture the identifier tag and associated sequences from the random shear points;

6) segregating tagged sequence pairs according to the source molecules identified for single-molecule sequence assembly, for tallying polynucleotides of identical sequence, and for reconstruction of the statistical structure of the starting mRNA population.

The 'tag' typically possesses two elements: (1) a unique SMID, comprising a sequence-identifiable region of random sequence of sufficient complexity to ensure that the vast majority of polynucleotides are unlikely to receive the same identifier; (2) a region of invariant sequence ("SMID Wrapper") that allows the SMID to be identified unambiguously. Other aspects of tag design in specific embodiments are enumerated in Detailed Methods.

The design, synthesis, applications and methods of use of SMID reagents that enable this technology are provided in embodiments below. The identifier tag could be incorporated by end-ligation directly to mRNA; in certain embodiments, the tagging reagent possesses a poly-T tail; used to prime reverse transcription from the poly-A tail of mRNAs, the tagging reagent incorporates the tag into the 5' end of the resulting cDNA. Added in surplus, this reagent will capture mRNA in the suspension; added in less than stoichiometric amounts, it captures an unbiased random sample.

Tagged polynucleotides may be replicated by PCR, for example, a minimal protocol of limited efficiency. A preferable approach entails removing the mRNA from the cDNA/mRNA heteroduplex by enzymatic digestion, followed by circularization of the tagged, single stranded cDNA with an appropriate form of RNA ligase capable of acting on single stranded DNA. Any residual linear forms may be removed with exonuclease I. The single stranded cDNA may be ligated into covalent circles with variants of T4 RNA ligase (c.f. Epicentre; Promega Corp.) Some forms of this enzyme that originated from thermophilic bacteria have been further modified for optimal use at elevated temperature (e.g., CircLigase: Epicentre). This enzyme efficiently circularizes single stranded RNA or DNA with low levels of linear or circularized intermolecular ligation products and appears independent of oligonucleotide sequence. While the enzyme cannot ligate double stranded DNA, it was discovered that it can ligate a free single stranded 3' end to the 5' end of a single stranded molecule that is folded into a duplex configuration, at the 60 degree incubation temperature.

Circularized, tagged cDNA molecules are aliquoted into amounts dictated by the scale of sequencing to be performed; ideally every individual molecule in the sample will be covered by sequence reads at a predetermined depth (e.g., 5×, 10×, 25×, etc.). The aliquoted material (circularized, tagged cDNA molecules) are subjected to rolling circle amplification (RCA) with the highly processive, strand-displacing phi 29 DNA polymerase. RCA may be primed non-selectively with random-sequence primers; or with polynucleotides directed against invariant regions of the tag; or with polynucleotides directed against sequences specific to individual genes; or paralogous members of multi-gene families; or against sequences common to orthologous genes or multigene families. Each RCA product constitutes an extended homo-concatemer of a single cDNA, each copy linked to the next by a copy of a marker containing the SMID tag. Depending on the choice of primers, the RCA may yield a continuous single strand, or a branched (or "hyper-branched") double stranded product. Branched products may be debranched with S1 or Mung bean nuclease.

Fragmentation of the homopolymers is typically performed in two steps. First, debranched homopolymers are fragmented by enzymatic fragmentation, sonication, hydroshear or equivalent physical method, to sizes on the order of the average mRNA length for which sequences are desired—typically 2-6 kbp, or other sizes depending on the length of the target mRNA population. Second, the products of random physical fragmentation are cleaved with a restriction enzyme with a rare recognition sequence, for which one or more consensus sites have been designed into the SMID reagent. These steps create fragments, each with an internal sequence exposed by the random fragmentation on one end and a SMID on the other. Any of several massively parallel sequencing platforms may then be used to sequence the paired ends of each SMID labeled fragment. An adaptation to the mate-pair protocol of the Illumina High Seq is described herein as a proven example of method utility in efficiently sequencing tagged cDNA fragments.

In certain embodiments, the disclosure relates to the design, synthesis and applications of the source molecule identifying tags, and kits for their synthesis and applications and methods of use disclosed herein. The tagging reagents for mRNA sequencing and quantification are exemplified by Type I and Type II classes of DNA polynucleotide joiner/primers described herein. These are typically single stranded DNA molecules possessing an exposed single-stranded 3' extension of poly-dT capable of annealing with the poly-A tract of mRNA and priming retroviral reverse transcriptase synthesis of tagged single stranded cDNA.

Type I tagging reagents possess a SMID, other functional sequences, and may exhibit an absence of secondary structure. They may be obtained by commercial synthesis from the design sequence without further modification. Type II tags contain duplicate copies of the SMID. The tagging reagent may contain both copies of the SMID, or may be designed such that a single SMID is duplicated when copied into double stranded DNA.

Type II reagents, and their commercially synthesized precursors, possess secondary structures that: (A) are exploited in tagging reagent synthesis from commercially prepared precursors, and (B) serve useful functional roles in synthesizing enriched, SMID end-labeled cDNA fragment libraries for massively parallel sequencing. Described below are type II tagging reagent designs that differ in secondary structure and applications. They furthermore encompass more functional domains that provide versatility in reagent synthesis or final preparation of tagged cDNA sequencing libraries. Additional reagents described below include the Type II synthetic precursor polynucleotides and primers used for specific applications in library preparation.

Type II tagging reagent syntheses exploit secondary structure designed into a chemically synthesized precursor to directly elaborate a complex tagging reagent structure. Alternatively, secondary structure is used to elaborate a complex template upon which the final tagging reagent is synthesized and to permit their efficient purification as a reagent ready for use. This strategy permits the highly efficient synthesis and purification of these complex and variable reagents in pure forms, using a single synthetic enzyme.

In certain embodiments, the disclosure contemplates methods that include an alternative for synthesizing desired tagging reagent variations from a template affixed to a solid substrate.

Within certain embodiments, the analysis of data generated sequencing the tagged libraries typically entails the steps of:

1. SMID detection—the identifying randomized sequence is located either by means of flanking sequence elements (the 'wrapper'), or by the uniform placement at one end of each library strand, or both.

2. Read Sorting (Virtual Cloning)—sequencing reads are sorted according to SMID into separate "bins". A bin is a block of addresses in computer memory that stores related sequence data. Each read containing a SMID is assigned, along with its mate-pair read (or reads), to that SMID bin. Each bin represents an individual source molecule in the original sample (viz. a single complete mRNA molecule) and every sequence in that bin is traceable to that single molecule. This is the post-sequencing informational equivalent of cloning a physical cDNA from a mixture before sequencing (ergo 'virtual cloning').

3. Sequence trimming after the SMID tag is used to identify the strand represented by the associated reads where tag sequences are removed from the recorded reads, leaving only information derived from the source molecule.

4. Assembly of Source Molecule Sequence—trimmed reads within each bin are arranged in a maximally overlapping alignment to create a minimum number of contigs, each of maximal length. With adequate coverage, each bin yields a single contig comprising the end-to-end sequence of the source molecule. (Because each bin contains sequence reads from one relatively short cDNA source strand, complications that bedevil large scale (e.g., genome) assembly are circumvented. The main problem of transcriptome analysis, assigning sequence reads to individual transcripts, is removed. The entire assembly process is achievable with existing de-novo assembler software.

5. Referencing each assembled sequence to its source gene (or possibly genes, in the event of trans-splicing)-existing software can be used to update curation of exon/intron organization of each gene.

6. Identifying the source strand—information from tag orientation or reference to the source gene indicates whether the associated cDNA sequences correspond to the "sense" (protein coding) mRNA sequence, or its antisense complement. This can distinguish the sequences of mRNAs from poly-A labeled non-coding antisense sequences that could play regulatory roles in gene expression.

7. Summary reconstruction of the mRNA profile—the relative levels of steady-state expression of all expressed endogenous and exogenous (in the case of pathogen infections) genes are quantified, together with the relative expression levels of each sequence variant from every gene. These data provide associative information regarding linkages of sequence variations; e.g., associations of particular splice or RNA editing variants with particular alternative promoter sequences; concerted linkages of particular coding domains that may reflect interacting protein domains governing protein functional mechanisms, etc. Reconstructions can encompass comparative structures of messenger profiles from multiple tissues that might be sequenced together (multiplex sequencing), as in: samples from multiple tumors in a cancer patient and unaffected non-malignant control tissue; tissues sampled at various stages of development and differentiation; tissues sampled over the course of disease progression.

Reagents

In the context of certain embodiments of the disclosure, the follow terms are contemplated.

A "tag" refers to a polynucleotide attachment to a polynucleotide of interest (e.g., target sequence) that allows the resulting conjugate to be replicated and distinguished by identifying a part (or whole) of the attachment or replication thereof. Tags typically possess a multiplicity of elements that facilitate the preparation and analysis of sequencing libraries.

A "tagging reagent" refers to a polynucleotide reagent used to introduce a unique tag into a polynucleotide sample or samples. In certain contexts, the "tag reagent" refers to a group of polynucleotides with some parts of the polynucleotide containing sections with substantially overlapping sequences and sections with substantially non-overlapping sequences, i.e., wherein the population of overlapping sequences within non-overlapping sequence section are statistically low. Once the tag is conjugated to the polynucleotide it is typically replicated—thus, the tag creates multiple copies with identical sequences.

Figures 1A, 1B:
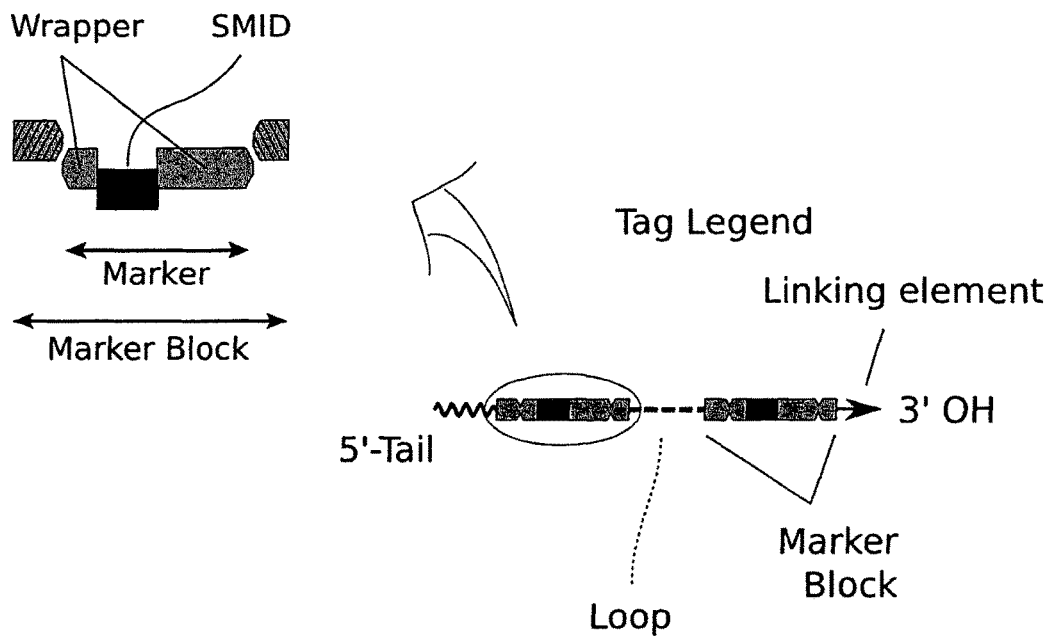
FIG. 1A schematically illustrates nested structures of a Marker-Block including SMID, 5' and 3' Wrapper sequences and flanking regions that include the 5' tail, 3' Linking Element (e.g., poly-T tail) and Loop structure. In this embodiment, the Marker-Block comprises those sequences retained in the final sequencing libraries and available for sorting reads according to batch, source and strand. The Marker Block may encompass numerous sequence elements, e.g., primer sequences and annealing sites used in tagging reagent strand (TRS) synthesis, or the PCR primer, cluster synthesis and sequencing elements, restriction enzyme cleavage sites of the sequencing protocol used in the adaptations illustrated herein.
FIG. 1B illustrates type I, type II-ps, type II-pa and type II-t tags showing 5' tail, Marker-Blocks, loops and 3' linker element. In examples described herein, the 3' linker element is a 3' single stranded oligo-dT ($T_{22}$ or $T_{22}V$). The variable residue (V=A, G, or C) primes synthesis from the extreme 3' base of the coded message immediately adjacent to the about 300-400 base poly-A tail. Tags are represented by four kinds of examples. Single-SMID single strand type I markers are highly efficient in priming cDNA synthesis and circularization reactions; these are prototype molecules in which only half of the restriction cleavage fragments generated during library preparation will be end-labeled. Type II-ps tags introduce two copies of SMID and both enzyme cleavage fragments will be end-labeled. This reagent does not directly identify the sense of the source molecule template, which may only be assessed by reference to the gene sequence. Type II-pa tags are similar to type II-ps, but also allow computational discrimination of the sense of template source strand, thus permitting identification of poly-A non-coding RNAs. Type II-t tags have the unique property that the SMID sequence is oriented in respect to the sense of the source strand, requiring no computational steps. These tags also permit specific SMID-identified cDNAs to be directly amplified by PCR for cloning and expression.

The "marker" refers to a part of the tagging reagent that is replicated in association with internal cDNA sequences. The marker identifies each sequenced fragment according to the individual molecule in the original suspension from which it was derived. Sometimes entire marker is, in principle available for final data assembly software. The marker may comprise two components. One the "SMID," or "Source Molecule Identifier" which refers to a sequence-identifiable region of random sequences, e.g., a series of random bases interspersed between invariant "check" bases: the random bases are sufficient in number to create high diversity in the tagging reagents, e.g. typically, but not limited to, greater than $10^9$ unique SMID sequences. Second, the "SMID wrapper" comprises invariant bases (overlapping sequences) flanking the SMID on one or both sides. Both the check bases and the wrapper facilitate detection of the tag in large arrays of library sequences. As illustrated in FIG. 1, the marker block contains the marker sequence (e.g., SMID plus flanking wrapper sequences) with additional adjacent sequence, which may include, for example, a PCR-primer sequence or its complement on one side of the marker, and recognition sequences for one or more restriction endonucleases on the other. The SMID, marker and Marker-Block thus comprise nested sequence elements of the tag.

For Type II tags described more herein, the "intervening loop," or "loop domain" may contain binding sites for one or more primers, or their complements. One or more restriction endonuclease recognition and cleavage sequences may also be present in the intervening loop.

The "clamp" refers to the annealing sequences flanking the intervening loop of the tagging reagent precursor (See FIG. 2A, "Anneal") that allow self-priming that extends the 3' end of the precursor, thereby creating an intramolecular, complementary copy of the Marker-Block, including the SMID. A 3' tail domain is typically poly-dT or a variant (e.g., dT22dV) used to prime cDNA synthesis from poly-adenylated mRNA. An optional 5' tail domain is typically a stretch of poly-dT or other sequence that will not, in general, hybridize with any other part of the tagging reagent. The 5' tail present a single stranded 5' end for efficient circularization of the completed cDNA by RNA ligase without the need for partially denaturing elevated temperature. The twin 5' and 3' tails of reagents which bear them allow their use in copying and circularizing cDNA from circularized RNA, as in embodiments of the method for sequencing Gppp capped mRNA. (Reagents may be characterized by having one (3' only) or two (5' and 3') tails, signified with a subscript as the last element in the tag designation (e.g., type II-ps$_1$ or type II-ps$_2$)

A "batch-code" refers any variation retained in the marker that may be used to distinguish library fragments on the basis of nucleic acid, e.g., mRNA, sample source. Multiple batch-codes may allow the simultaneous profiling of mRNA populations from several sources, as in a developmental series for a tissue, a tissue at various stages of progression of a disease, or comparisons between gene products from tissues of different species, etc.

Types of Tags

Different types of tags are contemplated: type I (single marker), type II-ps (two palindromic, symmetric markers), type II-pa (two palindromic, asymmetric markers), and type II-t (two markers in tandem, not palindromic).

Type I tags typically possess a marker together, one or more copies of a rare consensus binding and cleavage site for one restriction enzyme at the 5' flank of the marker and one or more copies of a second rare consensus binding and cleavage site for a second enzyme at the 3' flank of the marker. Tails may include 3' poly-dT to prime cDNA synthesis (from the poly A extension of messenger RNA or poly adenylated non-coding RNA), or 5' sequences that may facilitate circular ligation.

Figures 1C, 1D:
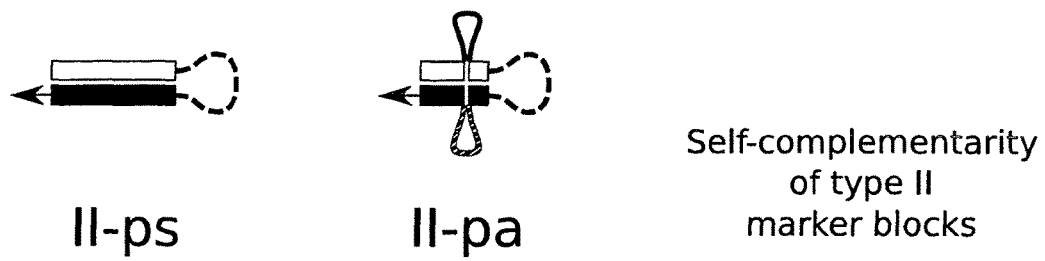
FIG. 1C illustrates the confirmation of tagging reagents. Two general configurations of type II-pa and type II-ps are illustrated.
FIG. 1D illustrates self-complementarity of Marker-Blocks; type I and type II-t generally lack secondary structure (c.f. B above). The complementarity of type II-pa and type II-ps tags leads to the introduction of two identical copies of unique molecular identifier (SMID) when the reverse transcript is converted to double stranded cDNA, doubling the efficiency of fragment tagging. The predilection for self-annealing of these regions allows efficient purification of the TRS after synthesis; it, furthermore, blocks amplification of fragments tagged at both ends (e.g. complete cDNAs) during library formation.
Figure 1E:
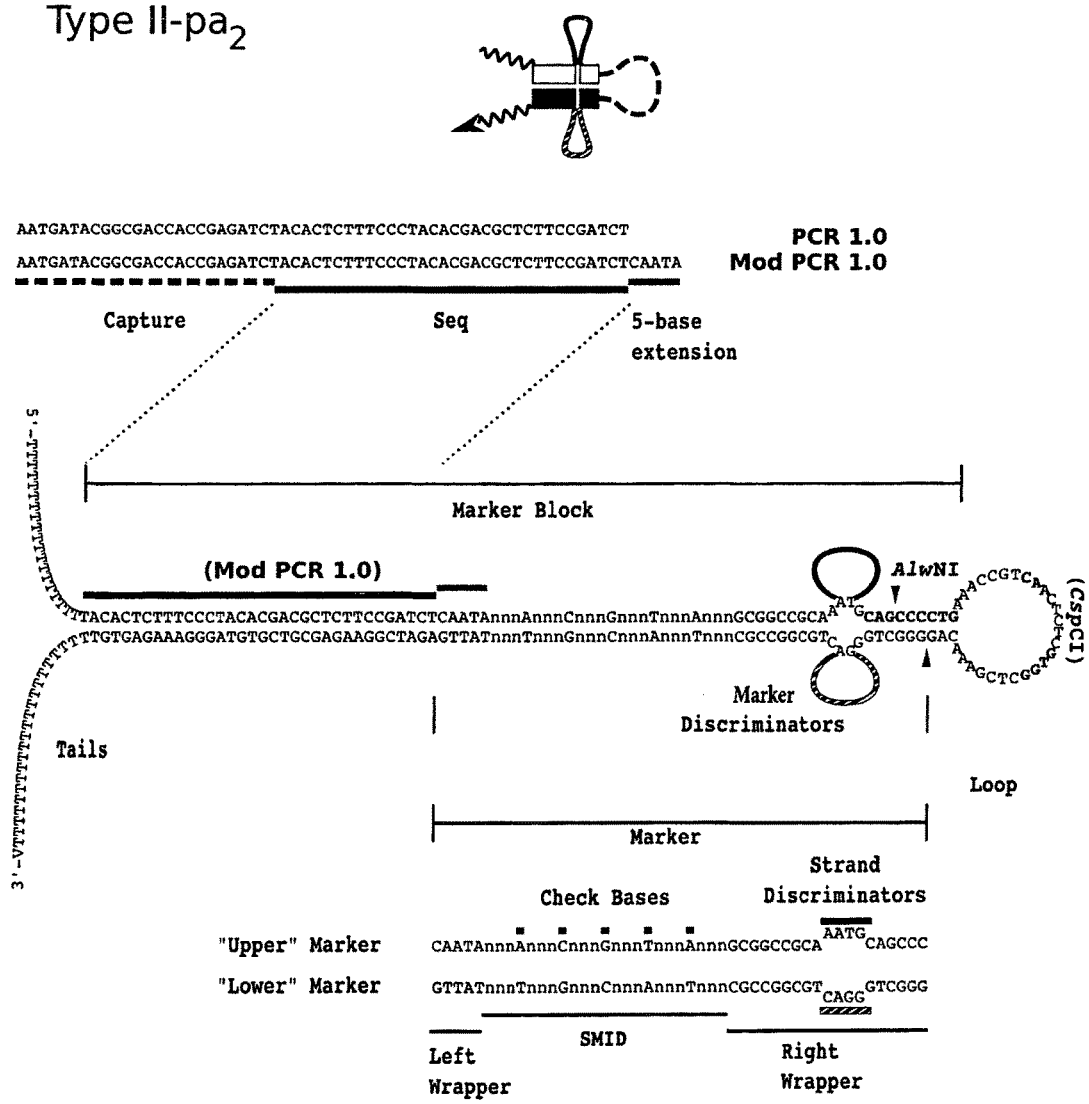
FIG. 1E illustrates tagging regents of type I and type II-pa with specific DNA sequences. In the type II-pa, within the Marker-Block shown, is a sequence for the Illumina adapter with PCR1.0, capture, cluster synthesis, sequencing and restriction enzyme sequences employed in mate-pair sequencing. Marker elements, including the SMID, strand sense-discriminators and restriction sites are illustrated.

An example of a type I tagging reagent is shown in FIG. 1E, schematically and as DNA sequence that exemplifies the attributes of the class. The reagent is a single stranded DNA polynucleotide that in general, but not without possibility of exception, lacks secondary structure. In this embodiment the reagent possesses a 3' tail comprising an oligo-dT tract of, but not limited to, 22 bases, capable of annealing with the poly-A tail of mature mRNA and priming cDNA synthesis by RNA dependent reverse transcriptase. The SMID of each tagging molecule represents a total of, but not limited to, 23 bases including 18 random bases distributed in six triplets separated by check bases. In the example of FIG. 1E, the marker-block encompasses duplicate rare consensus sequences for restriction enzymes, a pair of one type flanking the 3' and a pair of a second type flanking the 5' side of the marker. Thus, the SMID wrapper encompasses the interval between the respective 5' and 3' restriction cleavage sites and the boundary of the SMID.

A type II tag refers to a single stranded polynucleotide with, at a minimum, three consecutive domains in the order marker-block, intervening loop, marker-block; an optional tail domain may be included on either end, so the domain structure of a type II tag is, in general:

5'-[tail]-[marker-block]-[intervening loop]-[marker block]-[tail]-3' where tails indicate that the domain is optional. A tag with one or two tails is denoted by a subscript, e.g., Type II-pa$_1$ or Type II-ps$_2$ as examples of one and two-tailed forms, respectively.

One-tailed Type II tags efficiently prime cDNA synthesis from poly-A mRNA and are circularized with thermostable versions of RNA/DNA single-stranded ligase at elevated temperature. Two-tailed tags are more suited for circularization by generic RNA/DNA single stranded ligases without elevated temperature to remove secondary structure; they can be used to distinguish mature (capped) poly-A mRNA from immature 5' phosphorylated or 5' OH forms. In embodiments described here, the 3' linking element is a single stranded oligo-dT primer of cDNA synthesis, whereas 5' single-stranded tails may be oligo-dT, or alternative sequences according to their applications.

With one exception, a type II tag lacks any self-complementary regions that may form a stable duplex used for enzyme reactions in the synthesis or subsequent use of the tag reaction. The sole exception is the Marker-Block domain which contains the marker sequence and additional functional sequences.

In type II-p tags, the second marker block is the base complement of the first over a large extent of the domain, so that the tag polynucleotide will fold into a duplex produced by base-pairing between the complementary bases of the marker block domains. In this marker-block duplexed conformation, the other domains may remain largely without secondary structure.

In a type II-ps tag, the two marker block domains are complementary over their entire lengths. An example of a type II-ps tagging reagent is schematically shown in FIG. 1D. In this example, an extended 3' single-stranded tract of oligo-dT forms the 3' tail capable of annealing with the poly-A tail of a mRNA to prime cDNA synthesis. The II-ps possesses two marker-block sequences that are exactly complementary, thereby forming an uninterrupted duplex in solution: when copied into double stranded cDNA the two marker-blocks will create two identical copies of the SMID, each arranged in the same 5' to 3' orientation in the two strands.

In a type II-pa tag, one or both marker-blocks may contain an internal sequence segment that is not complementary to the other marker-block. When the two marker-block domains of a type II-pa tag hybridize, a length of single-strand will project from one or both arms of the duplex, forming an unpaired loop before rejoining the duplex. The purpose of the mismatch region within the marker-block is to make the two markers distinguishable during subsequent sequence analysis. This allows the marker sequence in an individual read to identify the sense of the original source molecule strand. This is not possible with a type II-ps tag where two identical copies of the marker are appended, in opposite sense, to the source strand.

An example of type II-pa tagging reagent is shown in FIG. 1E, schematically and as a DNA sequence. An extended 3' single-stranded tract of oligo-dT forms the 3' tail capable of annealing with the poly-A tail of an mRNA to prime cDNA synthesis. It possesses two Marker-Block sequences that are substantially complementary, thereby forming a duplex in solution: when copied into double stranded cDNA the two marker-blocks will create two identical copies of the SMID, each arranged in the same 5' to 3' orientation in the two strands. The Marker-Block encompasses, on the 3' flank of the marker, consensus sequences for rare restriction enzymes. Thus, when copied into double stranded cDNA, the action of these restriction enzymes serve to cleave 3' to each copy of the marker sequences in each strand, deleting the 'intervening loop' from the cDNA construct. The Marker-Block possesses, at the 5' side of the marker, a site for priming in order to allow for PCR amplification of the SMID during library preparation. See "Seq" in FIG. 1E. The tag also possesses two unpaired DNA segments in the marker-block, falling between the SMID and the restriction enzyme consensus sites at end of the Marker-Block that terminates in the intervening loop. See "marker discriminators" in FIG. 1E. When copied into double stranded cDNA and processed through the steps leading to the final library for sequencing, these distinct sequences will enable the strand of the original source molecule, associated with each particular SMID read to be distinguished.

In type II-t tags, the second marker-block is a tandem, exact duplicate of the first, in the same sense, (with the two copies separated by the intervening loop sequence). Both copies of the maker are therefore appended in the same sense to the source strand, so the sense of the source molecule may be inferred from the marker sequence in the sequencer output.

A type II-t tagging reagent is a single stranded DNA polynucleotide, typically without duplex structure, possessing two identical markers separated by an intervening loop. This reagent offers the same benefits as the type II-pa tagging reagent except that the marker always denotes the sense of the strand copied in DNA synthesis. The type II-t allows experimental determination of the strand sequenced without requiring computational manipulation. More importantly, the type II-t allows immediate and direct cloning of any individual cDNA.

Methods of Synthesizing One or Two Tailed Tagging Reagents:

Type I tagging reagents may be obtained by sequential solid phase synthesis, one nucleotide at a time or by coupling separately produced segments. Random base sites may be created by coupling a mixture of the nucleotides.

Type II-p (ps and pa) tagging reagents may be synthesized from a commercial polynucleotide precursor, employing properties of a biosynthetic enzyme, phi 29 DNA polymerase to exploit secondary structures designed into the precursor and reaction intermediates to elaborate the final reagents.

For the synthesis of a single-tailed type II-ps Tag (type II-ps$_1$), precursor molecule may be synthesized commercially that possesses the following four domains in 5' to 3' order:

(1) Complement to a 3'-single stranded tail desired in the final molecule (for example, but not limited to: 5'-WA$_{22}$ wherein W is the complement base to V)

(2) Marker-Block (5'-A-[B-SMID-C]-D 3'), where "[B-SMID-C]" is the marker itself (that element replicated and retained in the final sequencing library), and A and D are proximal 5'- and 3'-components of the Marker-Block.

(3) Intervening Loop; while this loop has no sites of complementarity within the precursor, it may contain a sequence complementary to a polynucleotide ("loop primer," LP) that may be used to prime the synthesis of a second strand intermediate in the reaction series.

(4) The complement to the portion of the Marker-Block 3' to the SMID (e.g., to part or all of C-D): this may be referred to as the intramolecular "clamp" for self-priming.

Figure 2A:
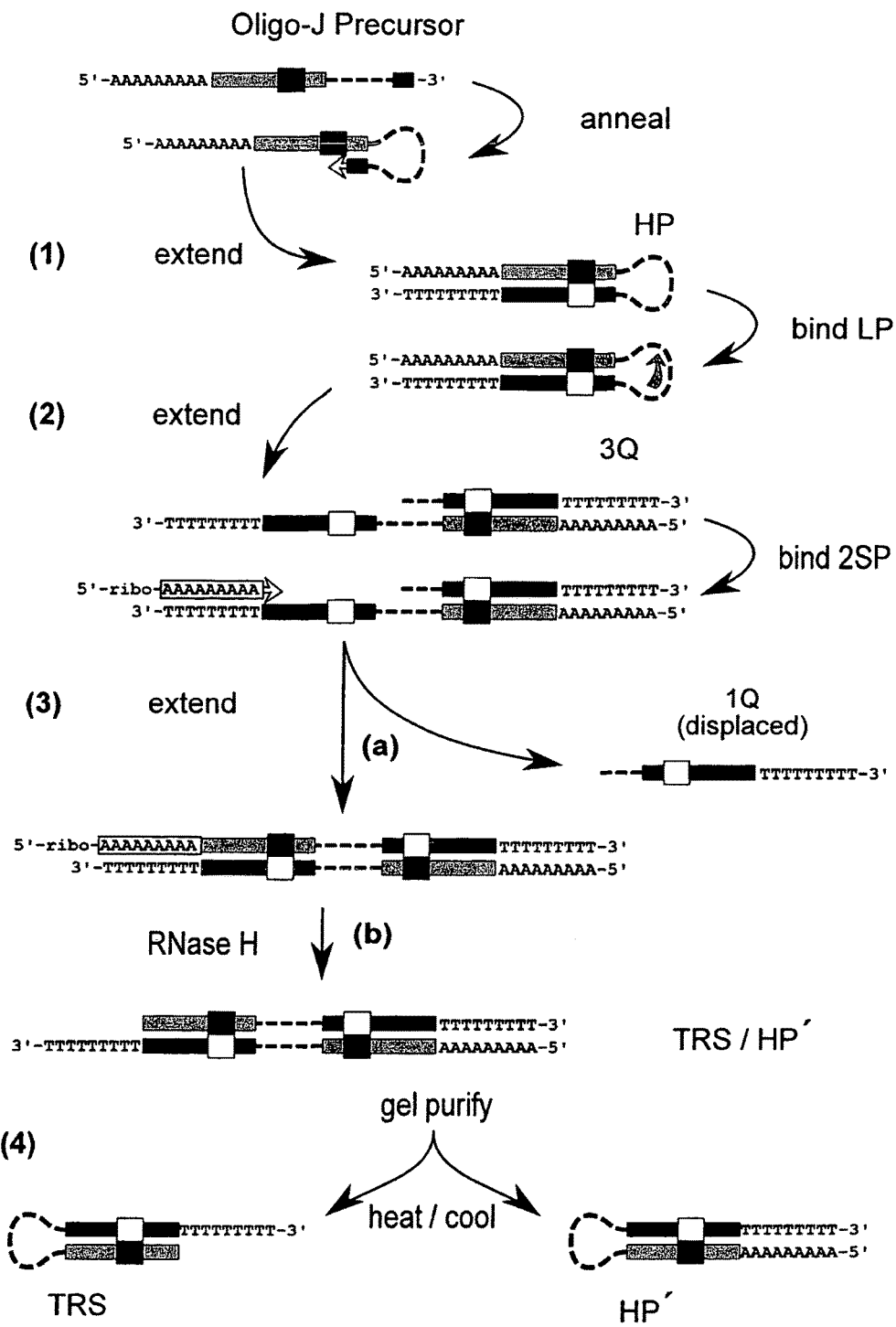
FIG. 2A illustrates the synthesis of type II tagging reagents for one-tailed type II-$ps_1$ and type II-$pa_1$ tagging reagents. The reactions described here may be performed in solution, not involving a solid phase, or with solid phase steps. Syntheses of both one and two-tailed type II-p forms share a common precursor and first step; distinctions between II-ps and II-pa forms originate from details of the marker block (c.f., FIG. 1C). (1) HP is a hair-pin configuration template upon which TRS is subsequently synthesized. HP is generated by extending the precursor Oligo-J with the enzyme DNA polymerase Phi 29. The Oligo-J precursor possesses a terminal clamp of moderate stability that causes the molecule to fold back onto itself to prime its extension, creating an intramolecular complement of the unique SMID element of the Marker. This reaction is typically quantitative (c.f.

The precursor will fold in solution to form a duplex between domain (4) and its complement in domain (2)—i.e., 5'-D'-C', the reverse complement of sub-domains C-D in the marker block: together these elements comprise a 'clamp.' See "Oligo-J precursor" in FIG. 2A.

This forms a stem-loop conformation, with the stem comprising the duplex and the loop being the intervening loop domain (3). Extending from the 5' end of the stem, on the side opposite the loop, is a single strand of DNA comprising the unpaired segment of domain (2) and the tail domain (1) discussed above.

This precursor polynucleotide is referred to as "oligo-J" because some versions of the folded structure resemble the letter "J," with the single stranded loop corresponding to the base of the letter. See FIG. 2A.

The "loop primer" (LP) polynucleotide is synthesized, which binds to the intervening loop domain (3) of oligo-J. The LP binding sequence may be offset by several bases on either side from marker-block domains, to permit unimpeded primer binding to the single-stranded loop and efficient priming of the polymerase reaction. In general, but not without exception, LP will not be phosphorylated on the 5' terminus, to guard against participation, (if retained in the final TRS preparation as a trace contaminant), in cDNA synthesis and the subsequent circularization reactions.

An RNA polynucleotide is synthesized that is identical to the 5' tail domain of oligo-J, referred to as the "RNA protector/primer" (RPP). In some embodiments, short DNA polynucleotide may be substituted for RPP, blocked to prevent DNA synthesis, added together with a separate primer for second strand synthesis.

Typically, in the first step of the synthesis, the 3' end of the duplex functions as a self-primer on oligo-J which is extended with a polymerase to copy the SMID and adjoining Marker-Block and tail domains. See FIG. 2A. This creates a blunt end stem-loop structure, where the stem now comprises the segment including the tail plus the entire marker block on one strand, and its exact complement on the other. Only the intervening loop domain is single-stranded. This structure is referred to as the "hairpin" (HP).

Typically in the second step of the synthesis, a free binding site for RPP is created on the 3' end of the HP as follows: A "loop primer" (LP) is bound to its complementary sequence in the single-stranded loop of HP. See FIG. 2A. This primer is extended with phi 29 polymerase, which copies the template up to its 5' extremity, displacing the 3' end of the strand from the stem in the process.

The product strand remains duplexed with the 5' half of the HP template, but the displaced template 3' half—including the complete marker block and tail domain—is now single stranded. This two-strand structure is referred to as "3Q." The short product strand alone is referred to as "1Q."

Structure of 3Q Duplex:
5' op-[D'-C'-SMID'-B'-A']-[tail]3'
3'[tail]-[A'-[B'-SMID'-C']-D']-Loop-[D--C--SMID--B--A]-[tail]5'

Typically in the third step of the synthesis, a complete copy of HP is created by binding RPP to the free 3' end of 3Q and extending with phi29 polymerase, which is readily primed with RNA polynucleotides. This synthesis copies the template strand and displaces the 1Q strand from the complex. See FIG. 2A.

The second and third steps are typically performed simultaneously. When the 3' end of the template is displaced in the loop-primed reaction, it may be degraded by 3' exonuclease activity of the polymerase. For this reason, both primers LP and RPP are added simultaneously so that RPP can hybridize to the template 3' end as it becomes exposed, protecting it from degradation.

In the fourth step of the synthesis, the RNA primer portion of the product is then removed with RNase H. The double stranded product contains the desired TRS duplexed with the HP template strand.

A variety of means may be used to remove primers and proteins, e.g., the "helper" strands 1Q which now represents a contaminating fraction of truncated copies of TRS and to separate the TRS and HP strands. Single stranded primers are generally degraded by the 3'→5' exonuclease activity of Phi 29. HP-TRS complex may be separated from 1Q by agarose gel electrophoresis, simultaneously removing residual polynucleotide primers of reactions 2 and 3, and any proteins. Purified HP-TRS is recovered from a gel slice by conventional methods (electro-elution; melting agar in chaotropic salt, extraction and membrane purification, etc.). If, during extraction from the gel, or afterwards, the HP-TRS duplex is transiently denatured, the strands will not subsequently reanneal. The overwhelmingly dominant kinetic pathway is for each molecule to collapse onto itself due to intramolecular complementarity. The resulting equimolar solution of HP and TRS may be used directly for tagging of mRNA. HP is inert in respect to annealing with mRNA and priming cDNA synthesis, and in respect to subsequent steps of the method (e.g., circularization of single stranded DNA).

Within a second embodiment, the oligo-J precursor is derivatized with a functional group that allows it to be attached to a solid support in such a way as to not interfere with enzyme activity on the polynucleotide. In one example of this embodiment, the oligo-J precursor may be modified with a chemical extension attached to biotin. After synthesis of the TRS-HP duplex, it, but not the contaminating 1Q or residual polynucleotide primers and enzymes, will bind to agarose or glass beads or other solid substrate to which streptavidin has been attached. 1Q, polynucleotide primers and any protein are removed by washing. The beads are then treated to transiently denature the TRS-HP duplex, resulting in regeneration of HP, attached to the substrate. TRS is released to solution, eluted with washing, and is in a form suitable ready for use in tagging reactions.

Figure 2B:
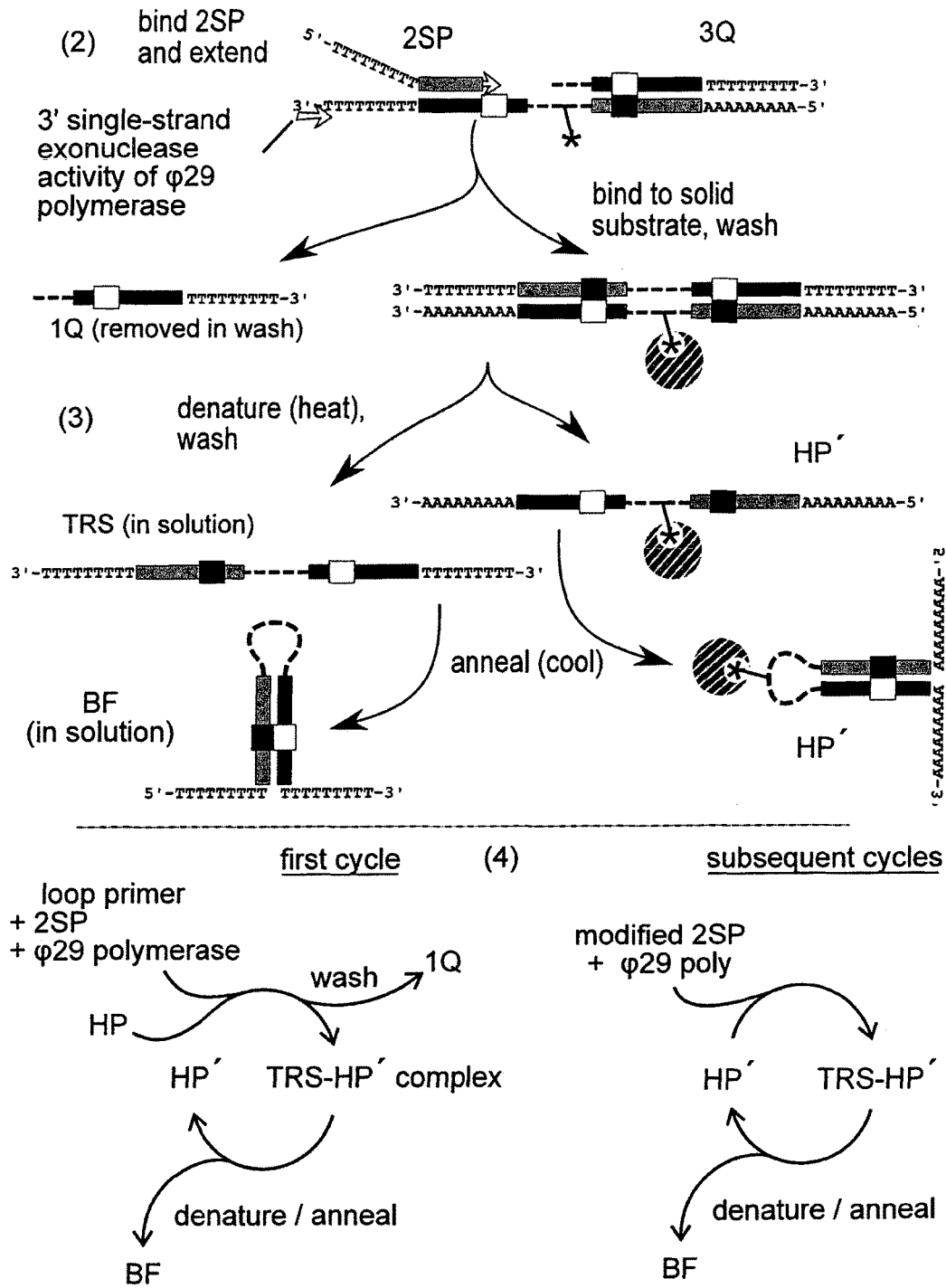
FIG. 2B illustrates the preparation of two-tailed type II-$ps_2$ and type II-$pa_2$ tagging reagents. These reactions are typically performed when some or all steps are performed with a solid substrate. The Oligo-J precursor is prepared commercially with a covalent extension that may be linked to a biotinyl group or may be a chemical linker for covalent attachment to sephadex, glass or other solid substrate (starred symbol). Here, use of a biotinylated version is shown, with the first steps in the reaction performed in solution. (1) HP extension and 3Q synthesis are performed as in FIG. 2A (1, 2) above. (2) TRS-HP' synthesis is primed with 2sP which anneals only to the 5' region of the wrapper sequence in the 3' single stranded end of 3Q. The non-complementary portion of 2sP is shown as oligo dT, but may be varied. 1Q is displaced as in 2A (3) above. 3' exonuclease activity of Phi 29 is intentionally not prevented, with the eventual elimination of the 3' single stranded portion of HP, followed by synthesis of a new 3' tail as a copy of the non-complementary portion of 2sP, to produce a modified template, designated HP'. (3) The TRS-HP' complex is adsorbed to Streptavidin beads; 1Q, primers and enzyme are removed by washing. Pure TRS is eluted following transient denaturation to separate the strands; mild denaturing conditions may be maintained during elution to prevent annealing with the complementary forked tails of HP'. The reaction is typically quantitative (c.f FIG. 7C). (4) Because HP' is regenerated on the solid phase, it may be used in future cycles to synthesize the TRS strand. This may best be performed if HP' is covalently attached to a solid phase. The use of the Loop primer to open the HP' structure to permit priming of TRS synthesis is no longer needed, and 1Q is not synthesized. A modified 2sP complementary to the exposed 3' fork of HP' (not shown) primes TRS synthesis: washing removes residual 2sP and enzyme. This allows repeated cycles of TRS synthesis from the same template. The cycles of solid phase synthesis are shown diagrammatically.

Synthesis of a two-tailed type II-ps tag (type II-$ps_2$) is illustrated in FIG. 2B. Synthesis of 1Q is initiated with Loop primer as in the previous embodiments in which the HP-precursor is derivatized with a biotinylated extension (or other extension suitable for interacting with a solid matrix) for the physical separation of final products. In this case, in the third reaction, performed at the same time as the second reaction, instead of RPP, a DNA polynucleotide (TRS primer) may be synthesized that is equivalent in sequence at its 3' end to a portion of the marker block in oligo-J, excluding the SMID (i.e., domains "A-B"). The 5' tail of this primer is not the complement of the 3' tail sequence of HP: (this non-complementary portion may vary as desired, and may be a 5' stretch of poly-dT). This primer binds to HP in the newly exposed 3' region in such a way that the 5' tail of the primer, and the 3' tail of HP both remain single stranded. Extension of this primer from its duplexed 3' end creates a TRS with non-complementary 5'- and 3' tails, and displaces 1Q. Upon release with transient denaturation, this strand will fold upon itself to form a stem-loop structure with a single-stranded tail on both 5' and 3' ends. HP and TRS are separated under mild denaturing conditions that prevent the 3' end of TRS and the free 5' end of HP from annealing.

Synthesis of a single-tailed type II-pa tag (type II$pa_1$) is prepared in the same way as a type II-$ps_1$ tag, with the exception that the 3' segment of the SMID wrapper (domain C in figure above) of the first marker-block is not entirely complementary to its counterpart (C') in the second marker-block, forming the clamp of the oligo-J precursor. The only constraint is that the two wrapper segments must be complementary adjacent to the SMID, and the extent of complementarity in this region must be sufficient to form a duplex stable enough to permit self-priming of the HP synthesis.

Synthesis of a two-tailed type II-pa tag (type II $pa_2$) is prepared exactly as for the two-tailed type II-$ps_2$ forms, beginning with the appropriate oligo-J precursor described in the embodiment above.

Solid-phase synthesis of type II-pa and type ups tagging reagents are attached covalently to a solid substrate such as glass via a chemical linkage.

In the syntheses of single-tailed forms, the oligo-J precursor polynucleotide includes a functional group that allows it to be attached covalently to a solid support, such as glass, in such a way as not to interfere with enzyme activity on the polynucleotide. In this way, reaction intermediates may be washed away and new reactants introduced with minimal manipulation or loss. The final product (TRS) is recovered simply by heating to melt the HP-TRS duplex. Upon cooling, the TRS and HP strands fold upon themselves to form hairpins. TRS is recovered in solution, and HP remains bound to the support.

In the syntheses of two-tailed forms, at the first cycle, synthesis of 1Q is initiated with Loop primer as in the previous embodiments. However in the third reaction, performed at the same time as the second reaction, instead of RPP, a DNA polynucleotide (TRS primer) may be synthesized that is equivalent in sequence at its 3' end to a portion of the marker block in oligo-J, excluding the SMID (i.e., domains "A-B"). The 5' tail of this primer is not the complement of the 3' tail sequence of HP: (this non-complementary portion may vary as desired, and may be a 5' stretch of poly-dT). This primer binds to HP at its newly exposed 3' end only, so the 5' tail of the primer, and the 3' tail of HP both remain single stranded. Extension of this primer from its duplexed 3' end creates a TRS with non-complementary 5'- and 3' tails, and displaces 1Q. Upon release with transient denaturation, this strand will fold upon itself to form a stem-loop structure with a single-stranded tail on both 5' and 3' ends.

If, in performing the solid phase synthesis of the two-tailed tagging reagent, exposure to 3' exonuclease activity of phi 29 polymerase is extensive, the free 3' end of HP will be degraded to the point of duplex with the TRS DNA primer, after which phi 29 polymerase copies the 5' end of the TRS primer to form a modified, covalently attached HP. After TRS is removed from the HP-TRS complex under denaturing conditions, the modified HP will adopt a forked end configuration with non-complementary 5' and 3' tails. Further synthesis of TRS with repeated cycles can thereupon be initiated with a primer directed only against the free 3' end of HP, without requiring prior synthesis of 1Q. The reaction is primed, the solid phase washed to remove reagents and the next cycle of TRS recovered under denaturing conditions. TRS is, in general, not allowed to recover secondary structure in the presence of the solid phase as it may re-anneal with the modified HP at the latter's free 3' end.

Thus, preparation of a fork-tailed, modified HP on a solid phase may be used for multiple cycles of TRS formation without the consumption of HP (and the cost of consuming additional oligo-J precursor). Such a solid-phase template can provide the basis for a kit for tagging reagent synthesis; repeating steps outlined in FIG. 2B can allow the solid-phase reagent to be modified to generate TRS with different 5' tails at the discretion of the investigator.

Figure 2C:
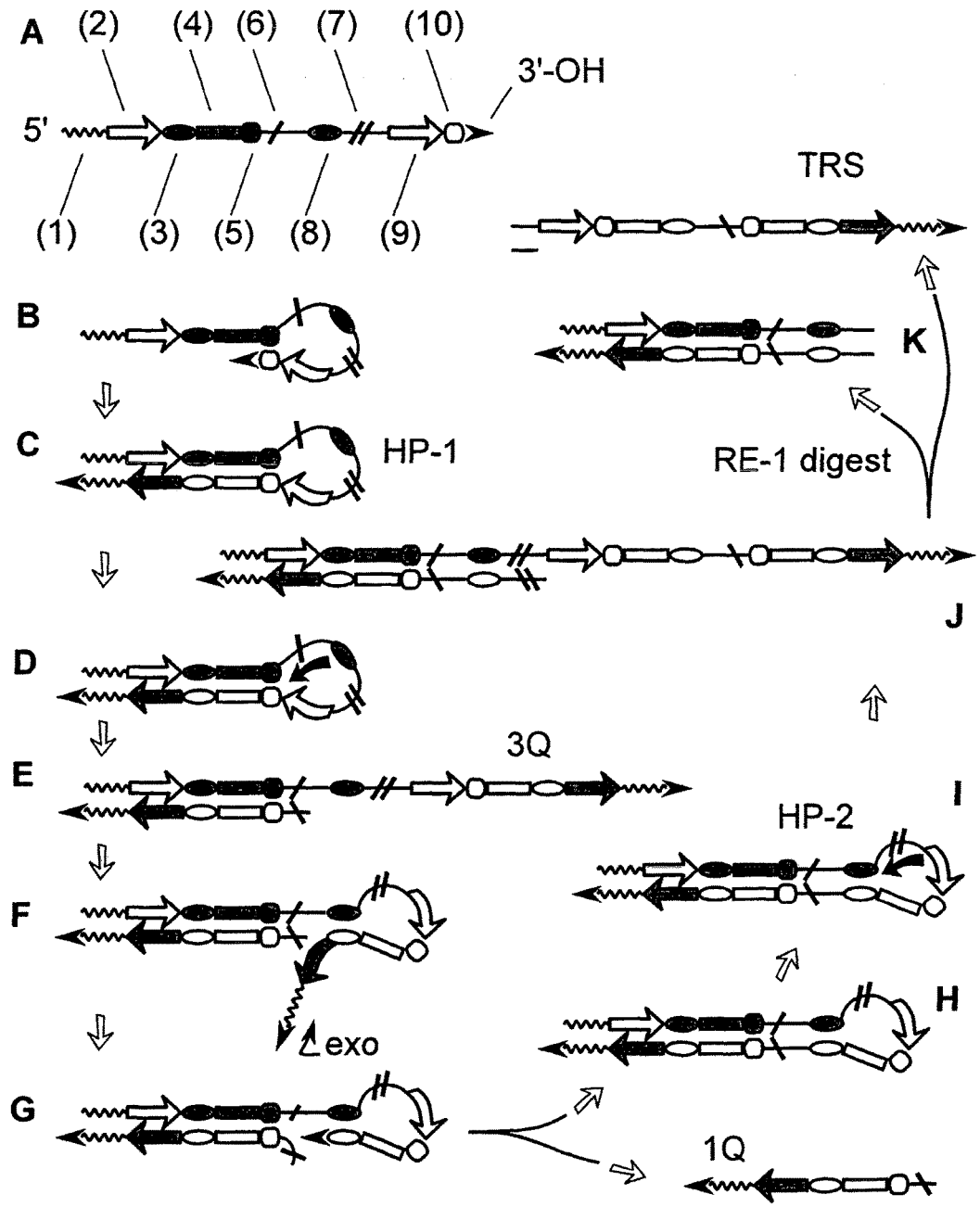
FIG. 2C illustrates the synthesis of Type II-t tags.
Figure 3A:
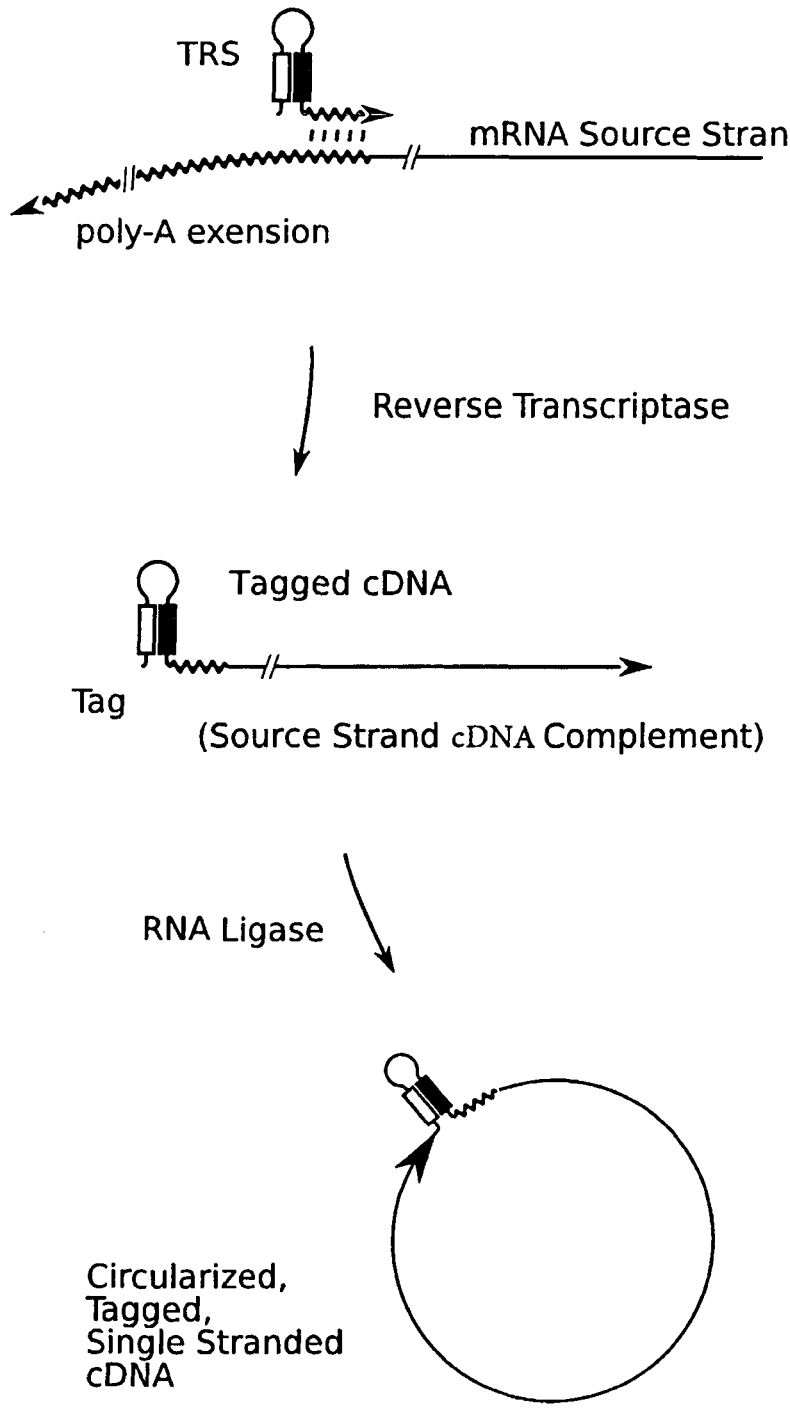
FIG. 3A illustrates an embodiment of methods used for library preparation. cDNAs are primed with a tagging reagent followed by removal of RNA and circularization with single strand RNA/DNA ligase. Linear remnants are removed with exonuclease I.
Figure 3B:
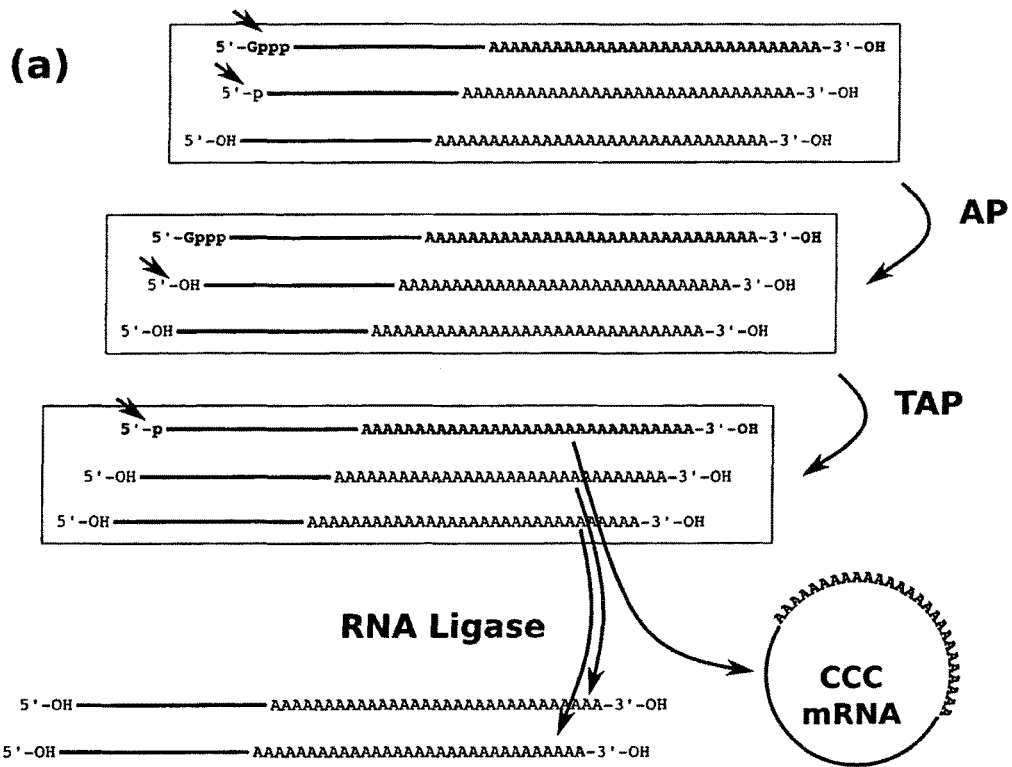
FIG. 3B illustrates distinguishing capped and uncapped mRNA. For some applications, distinguishing mature Gppp capped mRNAs from immature forms possessing terminal 5' phosphoryl or 5' OH groups may be desirable. (1) Tagging. (a) Capped forms: Total poly-A mRNA is treated with alkaline phosphatase to remove 5' phosphoryl termini, leaving uncapped molecules as 5' OH ends. Subsequent removal of the Gppp cap with tobacco acid phosphatase releases the 5' phosphoryl form that can be circularized with single strand RNA/DNA ligase. (Phosphorylated forms—omitting both enzyme steps used in (1) before circularization captures only endogenous 5' phosphoryl forms in the messenger population as circular RNA.) (b) Total uncapped forms. Treating poly-A mRNA with polynucleotide kinase prior to circularization and omitting the tobacco acid phosphatase step of (1), phosphorylates 5' OH forms. Leaving the capped molecules unmodified during subsequent treatment with single stand RN/DNA ligase subsequently results in circularization only of the uncapped mRNA population.
Figure 3B:
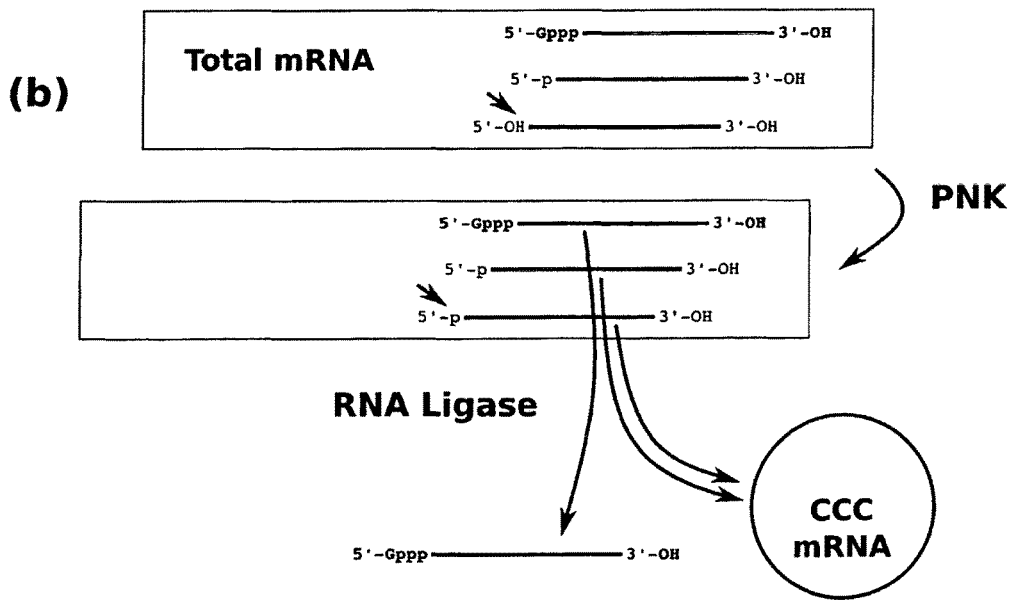
Figure 3C:
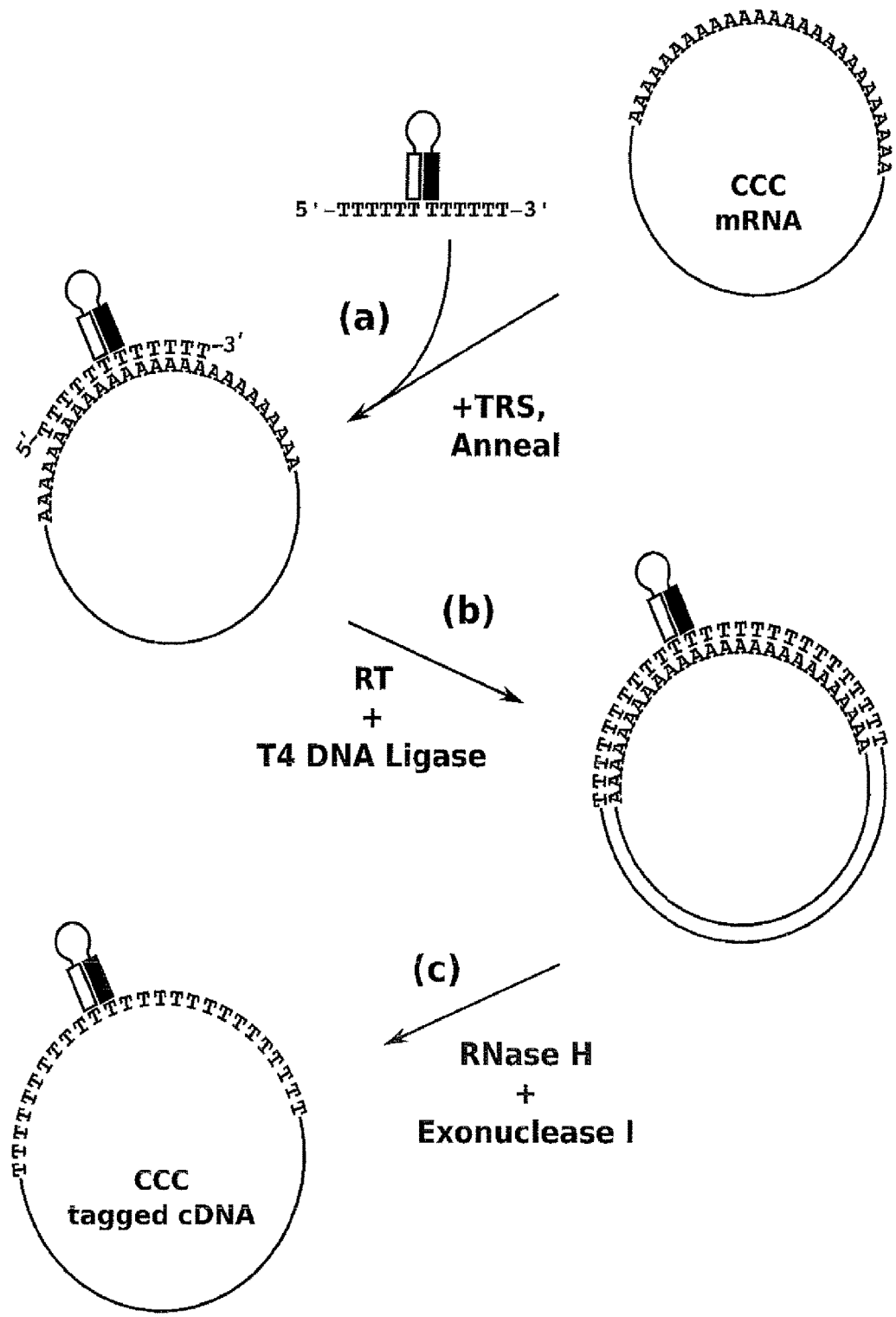
FIG. 3C illustrates cDNA synthesis. Sub-stoichiometric (<<1:10) two-tailed variant of type II reagent (e.g., type II-$ps_2$ or type II-$pa_2$) is annealed to previously circularized messenger and residual linear RNA followed by reverse transcription. cDNA synthesis is followed by efficient intramolecular ligation of cDNA by T4 DNA ligase to form circular cDNA. Circular but not linear mRNA provides a rate enhancing "splint" for the enzymatic action; moreover, in general, 3' poly-A messenger 'overhang' from the annealing site prevents circular intramolecular or intermolecular DNA ligation. RNA is removed with RNAse H. Linear single stranded cDNAs (not shown) are removed with exonuclease I. Resulting circularized single stranded cDNA is subsequently processed as are products generated from total poly-A mRNA (3A).
Figure 4:
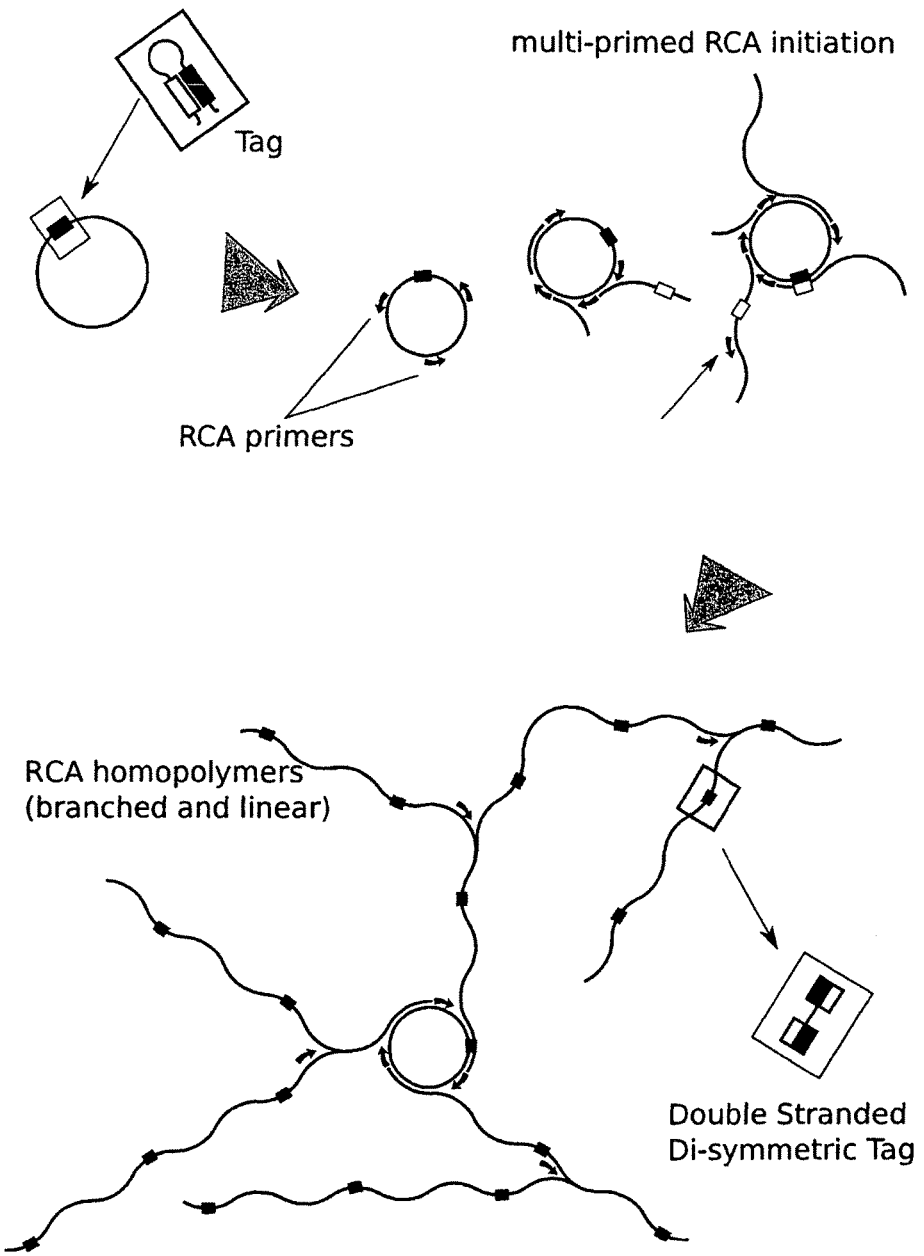
FIG. 4 illustrates rolling circle amplification. Each tagged, circularized single stranded cDNA is annealed to multiple primers (e.g., but not limited to thiophosphoryl random hexamers); second strand synthesis is catalyzed with the DNA polymerase Phi 29. As this highly processive enzyme circles the template and encounters the terminus of its own, or another enzyme's second strand, that strand is displaced as a long homopolymer; subsequent priming of this strand, in turn, results in a double stranded product, often branched at multiple priming sites of the reverse reaction. Linear homopolymers will also result. A second copy of the SMID is generated from type II-ps and type II-pa tags in the double stranded homopolymer DNA. Tandem copies of each cDNA are separated by an intervening copy of the tagging reagent, in this case encompassing symmetrically disposed duplicate copies of the unique SMID; separated from one another by a loop-derived segment bearing rare restriction cleavage sites. Homopolymers may be debranched with a single stranded nuclease (S1 or Mung Bean nucleases), prior to the next step.
Figure 5:
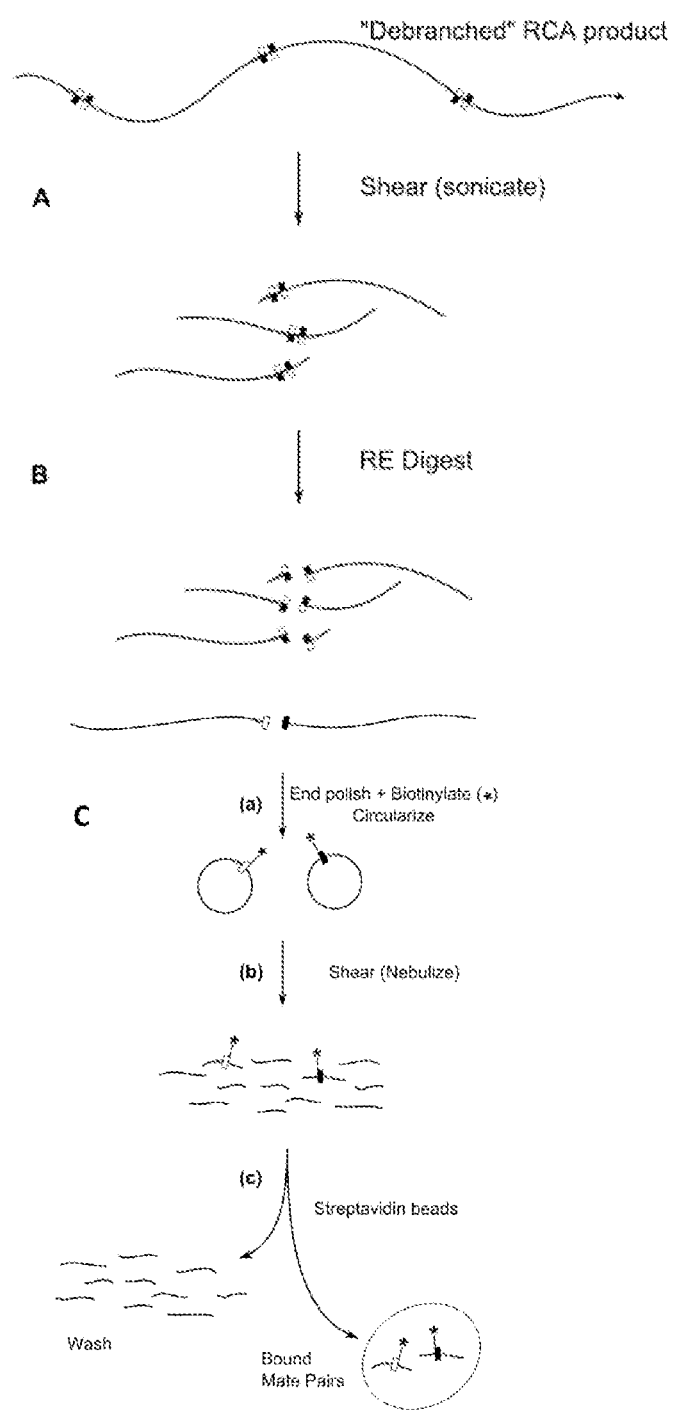
FIG. 5 illustrates the processing of RCA amplified cDNA homopolymers. A) Fragmentation. Following debranching, concatenated homopolymers are fragmented by sonication, enzymatic fragmentation, hydroshear, or comparable physical process into optional lengths of the order of the size of an average target cDNA. B) Restriction Cleavage. Random fragments are cleaved with a rare restriction enzyme (or other sequence-specific cleavage agent) at sites in the loop-derived connector between Marker-Blocks. Fragments possessing a tagged junction will give rise to two cleavage strands possessing the Marker Block including the unique SMID on one end and, on the other, produced by enzymatic fragmentation or a random end from a cDNA internal sequence produced by sonication. In general, these fragments are used to generate Paired-End or mate-pair Libraries with protocols for any of a number of Next generation shotgun sequencing platforms. This is here illustrated by an adaptation of the mate-pair protocol for the Illumina High Seq or Illumina MiSeq instruments. C) Fate of End-tagged fragments in the Illumina mate-pair protocol. The Illumina mate-pair protocol is widely used for genomic sequencing where it is useful to markedly extend the separation of ends to be sequenced. This applies to cDNA sequencing in which the terminal Marker must be associated with random reads throughout the length of each cDNA (avg.~1.7 kb, max~15 kb). Here the fate of end-tagged fragments in the initial steps of the standard Illumina mate-pair protocol is shown. Fragments lacking Marker Block will be carried through these steps, to be eliminated subsequently. (1) After initial shearing (sonication or enzymatic fragmentation) and restriction digestion, DNA fragments are subjected to end-repair, terminal biotinylation and circular ligation. Linear remnants are removed with exonuclease I and II. (2) Circularized cDNAs are disrupted by nebulization followed by gel purification of fragments of 300-500 bp. Biotinylated junctional fragments are captured by Streptavidin beads and non junctional fragments removed by washing.

Synthesis of type II-t reagents is illustrated in FIG. 2C. A precursor molecule may be synthesized commercially that possesses the following eleven domains in 5' to 3' order: (numbers in parentheses correspond to elements in FIG. 2C).

(1) Containing the complement to a 3' tail desired in the final molecule (for example, but not limited to: 5'-WA$_{22}$)

(2) (optional) Containing a PCR primer complementary sequence (3) Containing a sequence complementary to a DNA synthesis blocking polynucleotide.

(4) Containing sequence complementary to a self-priming clamp sequence (SP-2 complement).

(5) Containing the SMID complementary sequence (6) Containing sequence complementary to a self-priming clamp sequence (SP-1 complement)

(7) Containing sequence complementary to an polynucleotide ("LP-1"). The LP-1 binding site is offset by several bases from the 3'-end of domain (5) to allow proper binding of the loop primer LP-1 and efficient extension of the bound primer with phi 29 DNA polymerase. Domain (6) also contains a rare recognition sequence for a restriction endonuclease (RE-L (stroke in figure)) to be used in library preparation.

(8) Containing clamp sequence SP-2 complement (repeat of domain 3)

(9) Containing a sequence complementary to an polynucleotide ("LP-2"). The LP-2 binding site is offset by several bases from the 3'-end of domain (7) to allow proper binding of the loop primer LP-2 and efficient extension of the bound primer with phi 29 DNA polymerase. Domain (8) also contains a recognition sequence for a restriction endonuclease (RE-T: (double stroke in figure)) to be used in the tag synthesis. The LP-2 sequence may extend on its 3' end beyond domain (8) and into the next domain, if desired. The sequence RE-T must extend to the 3' end of LP-2, but should be offset from that position by a number of bases sufficient to allow the restriction endonuclease to cleave both strands of a double-stranded substrate with LP-2 at its terminus.

(10) Containing a PCR primer complementary sequence (repeat of domain 2, if present).

(11) Containing self-priming clamp sequence 1 (SP-1) complementary to domain (5)

Two "loop-primer" polynucleotides are synthesized, LP-1 and LP-2, with sequences complementary to their respective binding sites in domains (6) and (8) of the precursor polynucleotide.

A blocking DNA single stranded polynucleotide complementary to domain (3) is synthesized. The precursor polynucleotide forms a stem-loop conformation, with the stem comprising a duplex between domains (5) and (10) (SP-1 and its complement). The loop contains domains (6) to (9). Extending from the 5' end of the stem, on the side opposite the loop, is a single strand of DNA comprising domains (1)-(4). See FIG. 2C (A),(B).

The precursor is annealed to the blocking DNA polynucleotide, after which the 3' end of the precursor polynucleotide in the stem-loop conformation is extended with DNA polymerase (Klenow), priming from SP-1, copying the 5' single-strand to form a partial hairpin (HP-1, FIG. 2C (C)). The arm of the hairpin stem contains a newly synthesized clamp sequence SP-2, complementary to domain (4) on the template, but does not extend past the blocking polynucleotide.

The loop primer LP-1 is introduced and allowed to hybridize to the loop of the hairpin. Extension with phi 29 polymerase copies the 5' arm of the hairpin, displacing the 3' arm as a single stranded segment (FIG. 2C (E)) and displacing the blocking polynucleotide into solution. The newly synthesized product strand remains duplexed with the 5' half of the HP-1 template, but the displaced template 3' portion is now single stranded. This two-strand structure is referred to as "3Q." The short product strand alone is referred to as "1Q," (c.f. FIG. 2C (H)).

The new SP-2 sequence created during HP-1 synthesis is now unpaired, and hybridizes to its complement—domain (7)—in the loop (FIG. 2C (F)). The remaining unhybridized nucleotides on the 3' end are successively removed by the 3'→5' exonuclease activity of phi 29 polymerase, back to the SP-2 duplex (FIG. 2C (D)). With the hybridized SP-2 now serving as a primer, phi 29 polymerase extends the 3' end, displacing 1Q into solution (FIG. 2C (H)). This creates a longer hairpin (HP-2) whose single-stranded loop comprises domains (8)-(11) from the original precursor polynucleotide (FIG. 2C (H)).

The second loop primer LP-2 is introduced and allowed to hybridize with its complementary sequence (domain (8)) in the loop. Extension of this primer copies the 5' arm of HP-2, displacing the 3' arm as a single strand (FIG. 2C (F)). Cleavage of this product at RE-1 by digestion with the restriction endonuclease separates the double stranded portion from the single-stranded piece, which is the desired TRS—i.e., a type II-t reagent.

If the precursor polynucleotide is biotinylated, the TRS may be isolated from the double-stranded cleavage product by incubation with streptavidin beads and recovering TRS alone in the supernatant.

Reagents for Highly Parallel Sequencing Platforms

In the mate-pair and paired-end sequencing modes of the Illumina High Seq instrumentation, DNA fragments to be incorporated into the respective libraries are end-polished, A-tailed and ligated to forked adapters that possess several functional elements; PCR sites, capture sequences, sequences for cluster synthesis, consensus cleavage sites and sequencing primers.

As illustrated, following adapter ligation, PCR amplification results in the attachment of unique pairs of termini to opposite ends of the double stranded DNA (e.g. A and B complementary pairs of polynucleotides). Although the opposite ends of each adapter-modified DNA fragment forming the amplified library will possess an A-terminus and a B-terminus, strands are equally likely to have one of the B-polynucleotides on the 5' or the 3' end of each strand, or one of the A-polynucleotides on the 5' or 3' end of each strand.

A and B directed PCR primers (PCR 1.0 and PCR 2.0, respectively) amplify the DNA fragment captured within. To selectively generate library fragments that possess exclusively a marker on one end and a cDNA internal sequence on the other, one may employ modified adapters, modified PCR primers, or both.

In one embodiment, a modified adapter will comprise a single strand corresponding to the B-fork of the standard forked primer. Upon being copied in the first round of PCR, this provides only a small segment capable of interacting with PCR 1.0; at the annealing temperatures used, priming of DNA synthesis from the A-terminus is diminished or prohibited.

In a second embodiment, a modified adapter will comprise a single strand corresponding to the B-fork of the standard forked primer and a small complementary portion of a truncated A-fork. This provides only a small segment capable of interacting with PCR 1.0 at the annealing temperature; at the annealing temperatures used, priming of DNA synthesis from the A-terminus is diminished or prohibited.

In one embodiment, a modified version of the A-fork specific PCR 1.0 is synthesized which possesses a (but not limited to) 5 base overhang at the 3' end. Phosphoryl bonds linking the bases are modified as phosphothioate, methyl phosphonates, or phospho-amidate linkages; this diminishes the ability of exonuclease activity in the polymerase from eliminating the overhang. As a result, DNA synthesis from the A-terminus, whether from the unmodified forked primer, the modified adapter possessing a truncated A-strand, or the modified primer comprising the B-strand only, is greatly diminished. Combining the modified adapters with the modified PCR 1.0 greatly diminishes DNA synthesis from the A-terminus.

Within certain embodiments, the tagging reagent has been so designed as to include an annealing site for the modified PCR 1.0 primer. As a result of these several steps, PCR amplification with the modified A-prime (PCR 1.0, modified) can proceed only from the marker sequence, through the SMID and into the associated random break site. Amplification from the B-terminus is unaltered. The consequence of these restrictions is every Phase I sequence begins with the marker sequence, proceeding to a random internal break site in the cDNA. Every mate-pair Phase II sequence begins at a second random break site from within the cDNA. Under these conditions, nearly all of the sequencing read pairs possess markers and thus may be used to construct the sequences of the source cDNA molecules.

Methods

In certain embodiments, the disclosure relates to tagging polynucleotides in a heterogeneous suspension to maximize their distinguishability. In a heterogeneous solution of polynucleotides, individual molecules can only be distinguished insofar as their sequences are different. In order to reconstruct the quantitative population profile from massively parallel short sequence reads, each molecule is first modified so as to be ultimately distinguishable from all others based on its complete sequence.

In certain embodiments, the method permits the processing of tagged oligonucleotides in such a way as to amplify and then fragment copies of each in such a way that the original tag is replicated in association with the internal fragments produced. This allows computational recovery of the associative information required to reconstruct the sequences and relative numbers of all oligonucleotides in the original heterogeneous solution.

In certain embodiments, methods disclosed herein are capable of returning the sequences of substantially all messenger RNA, or an amount that is statistically representative thereto, in a cell or tissue together with estimates of their relative levels of expression. These messages comprise a subset of the "transcriptome." A messenger profile, $T_m$ relates to the equation $$\tau = \sum_{g=1}^{N} p_g \left( \sum_{i=1}^{k_g} q_{gi} \cdot S_i \right) = \sum_{g=1}^{N} p_g \cdot \tau_g.$$

a weighted distribution of messenger RNAs, where S, represents a specific messenger sequence; $q_{gi}$ represent the relative abundance of the $i^{th}$ message for gene g; and $p_g$ represents the relative level of transcripts for each of N expressed genes. This information provides the basis for analyzing the statistical structure of a transcriptome to reveal intricate mechanisms governing a gain of information between the genome and the expressed cellular molecular phenotype.

In certain embodiments, the disclosure relates to methods of distinguishing substantially all mRNAs in a sample, or an amount that is statistically representative thereto. In certain embodiments, the disclosure relates to methods of reconstructing a profile of mRNAs wherein poly adenylated mRNA is isolated and combined with a substoichiometric suspension of a tagging reagent, e.g., type II-$pa_1$ reagent. By virtue of the 3' single stranded oligo-dT extension, the tagging reagent anneals to the poly-A tail of the mRNA. In this embodiment, quantification of source molecules is thus generally independent of any differences in replication efficiency of later steps in the protocol. cDNA synthesis by reverse transcription is primed from the 3' tag terminus is initiated with a retroviral RNA dependent DNA polymerase (e.g. Maloney Murine Leukemia Virus reverse transcriptase, or reverse transcriptases of other origins), under conditions to efficiently generate full-length cDNA.

In certain embodiments, the disclosure relates to methods of distinguishing all Gppp capped mRNAs in a sample. Mature mRNA possesses a Gppp cap on one end and poly-A tail on the other. Immature forms possess a 5' phosphoryl group or 5' OH. Within an embodiment directed at capturing the profile of only capped mRNAs in a sample, poly adenylated mRNA is isolated according to standard protocols that will encompass Gppp capped forms; mRNA that lacks the terminal cap but possesses a 5' terminal phosphate; mRNA that lacks the terminal cap but possesses a 5' OH. The poly-A mRNA is treated with alkaline phosphatase (AP) to remove the terminal phosphate from uncapped, 5' phosphorylated species. The sample is treated with tobacco acid phosphatase (TAP) to remove the terminal Gppp group leaving a 5' terminal phosphate only on those molecules. Previously capped mRNAs bearing the 5' terminal phosphate in sample are ligated into circular RNA with RNA ligase, while 5' OH forms remain linear. The mixed circularized and linear mRNAs are combined with a suspension of type II tagging reagent that possess both 5' and 3' single stranded poly-dT tracts (e.g., type II $pa_2$). Tags annealed to the poly-A tail of mRNA prime reverse transcription with retroviral reverse transcriptase. The circularized RNA provides a template or 'splint' for efficient ligation into circular cDNA with T4 DNA ligase. Linear cDNAs duplexed with linear RNA molecules are inefficiently ligated and largely remain in the linearized form. The sample is treated by RNAse H to remove RNA from the mRNA/cDNA duplexes and RNAse R to remove residual, non-replicated linear RNA, followed by removal of linear cDNAs with exonuclease I. The remaining circularized cDNA, reflects the profile of mature, capped mRNA in the original sample; the circularized form may be incorporated into subsequent steps in the method described herein.

In certain embodiments, the disclosure relates to methods of distinguishing mRNA that is uncapped but that possesses a terminal 5' phosphate. This embodiment is identical to that above, except that Gppp caps are left intact; 5' phosphoryl forms are subjected to circular ligation, followed by the remaining steps in the previous example. The circularized forms may be incorporated into subsequent steps in the method described herein. In an alternative embodiment, one phosphorylates the 5' OH forms of mRNA, circularize the RNA, leaving the Gppp caps intact. This would capture the "immature forms" and could be used to contrast their composition to those of mature forms.

In certain embodiments, the methods disclosed herein comprising the step of circularizing the individually tagged cDNA polynucleotides. RNA/cDNA heteroduplexes resulting from reverse transcription is treated with RNAse H to remove the RNA strand, followed by heat inactivation of RNAse H. The 5'-tagged single-stranded cDNA is circularized with RNA ligase according to standard protocols, followed by inactivation of the ligase and removal of residual linear cDNA strands with exonuclease I. The number of circularized cDNA may be estimated from the (limiting) stoichiometry of primers added to prime cDNA synthesis, or may be estimated by spectroscopic or other means and is divided into aliquots suited to the scale of final sequencing and desired depth of coverage.

In certain embodiments, the methods disclosed herein comprising the step of replicating circularized cDNAs as branched, linear, tagged homopolymers. In one embodiment, an aliquot of circularized cDNA destined for sequencing is subjected to RCA with the highly possessive DNA polymerase phi 29, primed with random oligomers. The products of RCA are long, frequently branched homopolymers of double stranded DNA, each comprising concatenated repeats of a single cDNA separated by a repeat of the source molecule-specific tag. In an alternative embodiment, an aliquot of cDNA destined for sequencing is subjected to RCA with phi 29 polymerase, primed with oppositely directed oligomers that anneal to unique sequences in the tag. In an alternative embodiment, an aliquot of cDNA destined for sequencing is subject to RCA with phi 29 polymerase primed with oligomers complementary to sequences of a selected gene likely to be conserved among mRNA splice variants. In an alternative embodiment, an aliquot of cDNA destined for sequencing is subject to RCA with phi 29 polymerase primed with polynucleotides complementary to generally conserved sequences of paralogous members of a multigene family or superfamily. In an alternative embodiment, an aliquot of cDNA destined for sequencing is subject to RCA with phi 29 polymerase, primed with oligonucleotides complementary to sequences of members of orthologous genes from different species.

In certain embodiments, the methods disclosed herein comprising the step of associating random internal segments of individual polynucleotides with the distinguishing markers derived from the source molecule the tagging reagents. Random internal segments are converted into a form that they may be sequenced in conjunction with identifying markers derived from the tagging reagents introduced at the point of cDNA synthesis. The long-chain polynucleotides may be subject to debranching by cleaving the single stranded forks with a single strand nuclease such as S1 nuclease or Mung Bean nuclease. The debranched long-chain polynucleotides are fragmented by physical methods that may include but are not limited to sonication, enzymatic fragmentation, hydroshear or nebulization to an average size range specified by the investigator. In some embodiments the optimal average size will be near that of an average mRNA (about 1.7 kb), e.g., about 3 kbp. In some embodiments, the optimal size range will be smaller than the size of an average mRNA (e.g., about 500 bp). In some embodiments the optimal size will be near that of the largest mRNA to be sequenced (e.g., about 30 kbp). Within some embodiments, aliquots of the fragmented material may be retained for subsequent cloning of particular mRNAs subsequently identified in sequencing as being of interest, for functional expression or other studies.

In certain embodiments, the methods disclosed herein comprising the step of cleaving fragments of cDNA polymers originating with type I tagging reagents. For cDNA polymers generated with type I tagging reagents and possessing a single marker, following enzymatic debranching and physical fragmentation, aliquots of fragments will be separately treated with restriction enzymes directed against consensus sequences lying only on the 5' or only on the 3' side of the marker. Following cleavage, these fragment aliquots will be recombined.

In certain embodiments, the methods disclosed herein comprising the step of cleaving fragments of cDNA polymers originating with type II tagging reagents. Following enzymatic debranching and physical fragmentation, the replicated cDNA polynucleotides will be treated with a restriction enzyme with a rare consensus sequence previously engineered into the tag. Fragments possessing the tag anywhere within the end-to-end sequence will be cleaved to leave the marker on one end of each of the cleavage fragments and a random break site on the other. In this step, the loop sequence separating the two marker elements in the bi-functional tagging reagent will, in general but not in all cases, be excised.

Typically, the net effect of these steps is the generation of a plurality of fragments, many of which possess on one end a random break point from within the sequence of the individual cDNA and on the other end a copy of the marker that identifies the original, individual source molecule. These fragments, subject to any of a variety of massively parallel sequencing platforms, encompassing paired-end or mate-pair sequencing methods, will generate large ensembles of labeled reads or Paired-End reads that may be segregated based on the SMID of the marker assembled into full-length sequences reflecting those of the original mixture of polynucleotides in the starting sample or samples.

The following example describes an embodiment employing the Paired-End or Mate-Pair sequencing protocols of the Illumina High Seq instrument platform. The Paired-End protocol in general, but not in all cases, is limited in providing internal sequences a maximum of roughly 800 bp from a tagged fragment end, generally limiting the size of the cDNA full-length sequence to about 1.6 kb, close to the number average size of mRNA, restricting the profile to approximately half of the mRNA population. The Paired-End protocol, in contrast, has no such limitation and may be, in general, applied in profiling the entire mRNA population.

In certain embodiments, the methods disclosed herein comprising the step of preparing paired-end sequencing libraries. Illumina protocol for Paired-End sequencing may be adapted for full-length mRNA sequencing with the methods described herein. In the example given here, the marker-tagged fragments, prepared as described above, are adapted as follows.

Enzyme-cleaved marker-tagged fragments not larger than about 800 bp are end-repaired, A-tailed and ligated to Illumina forked adapters. After removal of excess adapters by washing, an indexed library is produced by PCR using primers specific for the forked adapters. The resulting library is sequenced as described below for mate-pair sequencing.

Fragments with a marker sequence on one end and a random break sequence on the other end will be captured, as will fragments possessing marker sequences on both ends and fragments devoid of marker sequences. In some embodiments, the use of modified adapters and PCR primers may be introduced to generate libraries possessing a marker on one end and a random break sequence on the other. These modified steps are described under mate-pair sequencing, below. These methods typically generate internal sequences that fall within 800 bp of the 5' or 3' terminus of the cDNA and will therefore fail to capture full-length sequences for cDNAs much larger than ~1.6 kbp in length.

The Illumina mate-pair protocol is a modified procedure that substantially extends the size of DNA for which full-length sequence is provided, and is therefore the typical approach for mRNA profiling. Enzyme cleaved marker-tagged fragments are generated as described above that may be in the size ranges outlined above. The fragments are end repaired and biotinylated on the 5' ends of each strand and circularized by the standard protocol. Biotinyl groups thus mark the junctions of the circularization reaction. Therefore, in fragments possessing a marker on one end and a random break point on the opposite end, circularization creates a physical linkage of the source-molecule identifying SMID with a random break point in the cDNA, and this junction is covalently attached to biotin residues.

Circularized, biotinylated cDNAs are again subjected to fragmentation by nebulization, generating a range of fragments averaging 300-500 bp in length. These fragments are subjected to end-repair and A-tailing and are ligated with either standard Illumina forked adapters, or custom modified versions of the adapters as described. These are adsorbed to streptavidin beads and non-junctional fragments removed by washing. Fragments ligated to Standard Illumina forked adapters are subjected to PCR with Illumina PCR 1.0 (A) or PCR 2.0 (B).

The net effect of PCR amplification is the generation of double stranded DNA fragments which possess on one end the A-primer sequence and its complement and on the other the B primer sequence and its complement. Replicated copies of identical cDNA segments will be generated in which the A and B pairs will be linked to either end. The A- and B-termini encompass primers for PCR with PCR 1.0 or PCR 2.0 primers, capture sequences with which single stranded DNA will be annealed to single stranded A and B specific polynucleotides in the sequencing chamber; priming sequences for cluster synthesis; cleavage sites for A or B terminus specific reagents used during the mate-pair sequencing protocol; and primer sites whereby the 3' ends of capture polynucleotides prime DNA synthesis in the sequencing process. In one embodiment, a modified adapter may be used comprising a single strand of T-tailed DNA corresponding to the B-strand of the standard forked adapter. In one embodiment, a Modified Adapter may be used comprising a single strand of T-tailed DNA corresponding to the B-strand of the standard forked adapter, annealed to a short segment of the A-strand of the standard forked adapter, but lacking segments that will permit annealing of the A-primer (PCR 1.0) under the conditions of the PCR reaction. In certain embodiments, nebulization fragments to which adapters have been added are adsorbed to streptavidin bead and unbiotinylated DNA fragments that do not encompass the junction of the circularization reaction are removed by washing. The biotinylated, adsorbed fragments are subjected to PCR with PCR 1.0 and PCR 2.0 primers, releasing into solution double stranded DNA with the A-primer pair on one end and the B-primer pair on the other. This constitutes a mate-pair library that captures the junctions of the circularization reaction.

In alternative embodiments, biotinylated, adsorbed fragments that possess terminal segments that are subject to priming of DNA synthesis by the PCR 2.0 but not PCR 1.0 are derived from one of the modified adapters. For these fragments, PCR primed with PCR 1.0 and PCR 2.0 proceed in which one strand is primed by PCR 2.0 annealed to the end terminal adapter strand, while synthesis in the opposite direction is primed with PCR 1.0 that binds to the A-strand sequence previously incorporated as a PCR primer site in the marker-block retained in the fragment, derived from the tagging reagent.

Within a further embodiment, the protocol is modified such that for these fragments, DNA synthesis may be primed in one direction with PCR 2.0 annealed to the end terminal adapter strand, while synthesis in the opposite direction is primed with PCR 1.0 (modified), where PCR 1.0 (modified) is rendered incapable of priming synthesis from the terminus by virtue of a several base overhang that is not complementary to the terminal adapter nor, in general, to the end of the target DNA sequence.

Within one embodiment the modified PCR 1.0 primer may be employed with the standard Illumina forked primer adapters. Within one embodiment, the modified PCR 1.0 primer may be employed with the modified single stranded B adapter. Within one embodiment, the modified PCR primer may be employed with the modified primer comprising a normal B-strand and truncated A-strand.

In some embodiments it is recognized that, by design, in libraries formed with type II-$ps_1$, type II ps-2, type II $pa_1$ and type II $pa_2$ but not type I or type II t markers, fragments possessing markers at both 5' and 3' ends will not be amplified in the final libraries because upon circularization prior to nebulization Marker-Blocks (but not the intervening loops) will be rejoined and in consequence of internal complementarity the sites for PCR 1.0 primer or PCR 1.0 modified primer annealing will not be available for the amplification reaction.

In some embodiments, it is recognized that in libraries formed with type II $ps_1$, type II $ps_2$, type II $pa_1$ and type II $pa_2$ but not type I or type II t markers, fragments devoid of markers anywhere in the sequence will lack the sites for PCR 1.0 primer or PCR 1.0 modified primer annealing and therefore not be amplified.

The net result of the modified standard protocols is the generation of a Mate-Pair library in which each fragment preferentially (>80%) possesses the A-primer/sequencing pair on one end and the B-primer/sequencing pair on the other, but in which the sequence immediately proximal to the A-primer pair will always be the marker (including the source molecule identifying SMID) linked directly to a random break sequence within the cDNA sequence. The B-primer/sequencing pair will be linked to a second random break sequence within the same cDNA sequence produced by nebulization, in general corresponding to a region downstream of the A-linked sequence separated by the average size of the nebulization fragment (e.g., 300-500 bp).

The net result of the modified standard protocols is that use of a single chamber in the High Seq instrument will yield generally >100,000,000 paired sequence reads, essentially all of which will be identifiably tagged with respect to source molecule SMID. Use of all 15 available chambers will yield generally >1,500,000,000 paired sequence reads, essentially all of which will be identifiably tagged with respect to source molecule SMID. Thus, depending on desired depth of coverage, a single chamber may yield assembled sequences of upwards of >1,000,000 full length messages and the combined chambers of the existing instrumentation may yield assembled sequences of >15,000,000 full length messages.

Certain methods utilize fluorescently labeled nucleotides attached to a growing double stranded sequence wherein the polymerization is controlled with chemical functional groups. Areas of a solid surface are enhanced with the same polynucleotide and the fluorescently labeled nucleotide indicates which base is being added. The approach described may also be extended to other protocols, including full-sequencing of intermediate sized fragments (>300 bp).

In the paired-end method of the Illumina High Seq instrumentation, the library comprises fragments typically of less than 800 bp. The library composed of the double stranded, vectorially modified, blunt ended DNA fragments are denatured into single strands. These are annealed to a lawn of covalently attached, single stranded polynucleotides (complementary to the 3' ends extensions B or A) on the surface tile of a capture chamber (flow cell).

The capture polynucleotides prime synthesis of a strand complementary to the annealed single stranded DNA, after which the product is denatured and the (non-covalent) template is washed away. The retained strand then anneals to a nearby capture polynucleotide complementary to its free 3' end. A second strand is extended from this capture polynucleotide, generating a double stranded "bridge", tethered at either end only by the 5' ends of the DNA duplex.

These bridges are denatured and the single strands are reannealed to new capture polynucleotides and the process is repeated until amplification creates, for each DNA fragment originally annealed to the chamber surface, a cluster of polynucleotides attached to the surface by either their A or B ends. This typically generates a large-number (e.g., 100,000,000-600,000,000) of clusters per flow cell sequencing chamber.

Sequencing is typically conducted in two phases. In phase I, the population of DNA bridges is cleaved with a reagent specific to one of the two linkers, and non-covalently linked strands are denatured and washed away. This leaves single stranded DNAs in only one of the two orientations (e.g., B covalent 5' end) to be sequenced from the free end, employing the A sequencing primer introduced with the forked adapter described above.

Sequencing is performed by priming from the A-capture polynucleotide the successive incorporation the appropriate base from a solution of four distinguishable fluorescent nucleotide triphosphate derivatives; following optical recording of each newly added base, the fluorophore is hydrolyzed and the reaction repeated. In this way up to 150 bases of the free (3') end may be recorded optically.

Following phase I, the untethered strands generated during sequencing are denatured and washed away. The retained template is then re-annealed at its free 3' end to a capture polynucleotide on the tile (e.g., A). A new strand of opposite orientation is synthesized by extending the capture polynucleotide. The resultant population of bridged polynucleotides is then cleaved at the second (e.g., B) linker, and the resulting untethered strands are denatured and washed away, as illustrated. The remaining population presents a free 3' ('B') end, sequenced as before, priming with 'B' polynucleotide to yield the complementary sequence of the opposite end of the first sequenced strand. After compiling sequences from the optical recordings for Phase I and Phase I for each cluster, these read pairs are reported together for each cluster.

In mate-pair sequencing nucleic acids are fragmented, (e.g., but not limited to, by sonication, enzymatic fragmentation, or hydroshear) into segments, typically several kb. The resulting sequence reads thus capture the intervening sequences of up to twice the size of the average fragment. In selecting an initial fragmentation size range, the maximum size for full-length assembled sequences is set at approximately twice the original fragment size. In other respects, the instrument sequencing steps are identical in Paired-End and mate-pair protocols, the differences lying only in the preparation of the libraries.

Sequences are assembled computationally (See FIG. 11). To summarize, read-pairs are segregated according to the unique SMID identifiers that specify the individual source molecule from which the sequenced cDNA was derived. Avoiding the physical handling of each cDNA is what permits the massive yield of sequence data; this captures the intended meaning of 'Virtual Cloning,' in which only the sequence information rather than the physical cDNA is segregated, each from the others in the suspension.

Individual source molecules are identified and thus counted. Simple statistical analysis quantifies the likelihood that every cDNA in the original sample has been sequenced. Identifying and quantifying relative transcripts of every gene expressed requires no prior knowledge of which genes to search for, as in micro-chip surveys, and captures both endogenous and exogenous (e.g. pathogen) gene products.

Individual source molecules from each individual gene are categorized in respect to sequence variants from each gene. Similarly, SNP variations revealing relative haplotype gene expression, epigenetic modulation of gene expression, or sequence variations reflecting somatic mutations, are quantified. Collectively these quantities provide the statistical structure of the mRNA population. This provides information regarding relative transcriptional activation of gene cascades that may be associated with particular promoter elements, together with information regarding concerted selection of sequence elements associated with RNA turnover, rates of translation, RNA trafficking and concerted selection of sequence elements that may reflect domains that interact to influence the molecular mechanisms of the expressed protein, thereby governing biochemical properties constituting molecular phenotype.

The steps of sequence analysis may be as follows. The identifying SMID is located either by means of flanking sequence elements (the 'wrapper'), or by the uniform placement at one end of each library strand. This may be accomplished with existing software.

Tagged read-pairs are sorted according to SMID into separate "bins". A bin is a block of addresses in computer memory that stores related sequence data. Each read containing a SMID is assigned, along with its mate-pair read (or reads), to that SMID bin. Each bin represents an individual source molecule in the original sample (viz. a single complete mRNA molecule) and every sequence in that bin is traceable to that single molecule. Read sorting may first segregate tagged-pairs in terms of sample source when multiplexed mRNA populations (e.g. different tissues) have been sequenced in the same experiment.

After the SMID tag is used to identify the strand represented by the associated reads, tag sequences are removed from the recorded reads, leaving only information derived from the source molecule. Each read-pair provides two internal reads created by random breakpoints during initial fragmentation and subsequent nebulization; these are, respectively, the segment proximal to the SMID identifier and that from a second random break point downstream by roughly the average length of library fragments. The two reads of each pair correspond to complementary strands and thus must be converted into the same sense before assembly.

Trimmed reads (transformed into the same sense) within each bin are arranged in a maximally overlapping alignment to create a minimum number of contigs, each of maximal length. With adequate coverage, each bin yields a single contig comprising the end-to-end sequence of the source molecule. The entire assembly process is achievable with existing de-novo assembler software (e.g., Velvet).

Each assembled sequence is referenced to its source gene (or multiple genes, in the event of trans-splicing). Existing software can be used to update curation of exon/intron organization of each gene (e.g. Spidey).

Identifying the source strand, whether derived from information from tag orientation (type II pa or type II-t tagging reagents) or by reference to the source gene indicates whether the associated cDNA sequences correspond to the "sense" (protein coding) mRNA sequence, or its antisense complement. This step can distinguish the sequences of mRNAs from poly-A labeled non-coding antisense sequences that could play regulatory or other, unanticipated roles in gene expression.

The relative levels of steady-state expression of expressed endogenous and exogenous (where pathogen are present) genes are quantified by the number of unique SMIDS found in messages from each gene, together with the similarly quantified relative expression levels of each sequence variant from every gene.

These data provide associative information regarding linkages of sequence variations; e.g., associations of particular splice or RNA editing variants with particular alternative promoter sequences; linkages of particular coding domains that may reflect interacting protein domains governing protein functional mechanisms, etc. Reconstructions can encompass comparative structures of messenger profiles from multiple tissues that might be sequenced together (multiplex sequencing), as in: samples from multiple tumors in a cancer patient and unaffected non-malignant control tissue; tissues sampled at various stages of development and differentiation; tissues sampled over the course of disease progression.

The information derived from the primary reconstruction of the mRNA profiles may subsequently be subjected to higher order analyses, such as a search for somatic or inherited mutations; a search for up or down-regulated genes; a search for tissue-characteristic patterns of multi-gene expression; a search for pathogen gene expression, etc.

In the event that full-length constructs of particular messengers identified in the data analysis are desired for functional or other analyses, a combination of SMID identifier specific and gene-specific PCR primers may be used to amplify full-length cDNAs of any particular source molecule, followed by subcloning and confirmatory sequencing, may be conducted.

The yields of individual sequencing runs are dependent on the instrumentation platform and characteristics of the derived sequence reads. Moreover, capacities of Next generation sequencing platforms continue to expand, and current estimates must be regarded as lower limits. The levels of coverage for each cDNA depend on applications. Thus, relatively low depth of coverage may be sufficient to ascertain SMID identity and to assess exon retention in splice variants: because of inherent error frequencies of high throughput methods, higher coverage may be required to call single base changes with a high level of accuracy.

Within some embodiments of the method, a complete sequence is contemplated that comprises a coverage, r, of 1, 2 or 3 tandem repeats of a transcript of length T (e.g., but not limited to 500 to 10,000 bp). Sequence reads considered may be, but are not limited to, of length L (25-200 bp). A "contig," for this purpose, refers to a region of the original sequence completely covered by a set of overlapping reads; i.e., every base within the contig is represented in at least one read, and every read within the covering set has at least one base in common with another read in the same set. To "cover" a sequence refers to every nucleotide of the sequence is contained within at least one read. A sequence may be completely covered by more than one contig. In that case there exist neighboring pairs of nucleotides in which both are covered by reads, but are never found together within the same read. Such "split pair" defines the boundary between two contigs, so the number of contigs covering a sequence is one more than the number of split pairs. A 45-base sequence is covered by 6 or 7-base reads defining 2 contigs. The split pair defining the contig boundary is shown.

An unambiguous full length sequence of a transcript is one in which no split pair occurs in transcripts repeats of the full sequence, because in that case there is no way to rule out the possibility that any intervening sequence may have been missed. A single sequence with no repeats must be covered by no more than one contig. A tandem repeat may be covered by two contigs, because the split pair in one copy is unsplit in the other.

Thus, if the sequence comprises r tandem repeats of a transcript, to obtain the full-length transcript sequence requires a number of contigs k≤r. Note that this is a minimum. We could require that every base within a contig be reachable from every other base within the same contig via overlapping reads that share a minimum number (say 3) of bases. This would give us greater confidence that the reads cover truly adjacent sequences. Without modeling this, we may instead ensure that the coverage exceeds the minimum obtained from this model by some agreed upon amount. A sequence of three tandem repeats by two contigs increases the number of overlapping contigs by a factor of 1.5 over the number required to cover a single copy, and increases the likelihood that contigs will have larger overlaps at their ends.

Coverage is calculated as covg=NL/T, where N is the total number of reads, L is the read length, and T the transcript length. If covg is obtained by covering r tandem repeats with k contigs, then the single-transcript coverage is r times the coverage of the complete sequence bearing the repeats.

$$k = N\exp(-NL/rT)$$

Solving for N gives:

$$N = -kA\ W_{-1}(-1/A)$$

where A=rT/kL, and $W_{-1}$ is a branch of the Lambert-W function on the reals which return real (i.e., not complex) values for N in our case (*Adv, Comparative Mathematics*, 5, 329-359, 1996).

Tables of data were computed from various values of L, r T, and k. This information is best visualized graphically, presented in FIGS. 8B,C. A plot of the number of reads versus coverage for all parameters computed shows overall behavior. Each line segment connects points for five values of k (1, 2, 3, 5 and 10) contigs per total sequence—including repeats) for one transcript length (T), one transcript repeat value (r), and one read length (L). The three repeat levels (r) segregate the plot into three groups: (r=1), (r=2), and (r=3). This shows how coverage of a single transcript increases if the transcript is copied in tandem but covered by a fixed number of contigs. The larger transcripts are on top, as more reads are required to cover them.

Plotting a subset of the data to demonstrate the effects of read length on the total coverage required to capture the entire cDNA sequence. Longer cDNAs (e.g. 10 kbp) require reading 3.5 to 4-fold more bases with 50 bp reads than with 150 bp reads for the same level of assurance of covering the cDNA.

The abbreviated table illustrated in FIG. 8D demonstrates that a depth of approximately 10× requires for cDNAs of 3 kbp requires approximately 230 read of 150 bp. A lower depth of coverage with a read length of 167 bp may require on the order of 100 reads. A typical run from one chamber of the Illumina High Seq platform at present yields approximately 200 million read pairs with 167 bp of sequence per read, sufficient to fully sequence approximately 2 million cDNAs on the order of twice the size of the number average mRNA size. Using the full 15 chamber capacity of this machine would therefore be sufficient to sequence on the order of 30 million cDNAs of average size.

Assuming the average cell expresses products of 7,000-8,000 protein coding genes, this permits a dynamic range of approximately 250 mRNAs per gene for a single chamber; or between 3,000 and 4,000 using all chambers in a run. Neglecting the fact that this range will only increase as instrumentation performance increases, this seems sufficient to profile all of the messages for even a moderately complex tissue.

Terms

The term "polynucleotide" or "polynucleotide" refers to a molecule comprised of two or more deoxyribonucleotides or ribonucleotides, preferably more than three, and usually more than ten. The exact size will depend on many factors, which in turn depends on the ultimate function or use of the polynucleotide. The polynucleotide may be generated in any manner, including chemical synthesis, DNA replication, reverse transcription, or a combination thereof.

The term "nucleic acid" refers to a polymer of nucleotides, or an polynucleotide, as described above. The term is used to designate a single molecule, or a collection of molecules. Nucleic acids may be single stranded or double stranded, and may include coding regions and regions of various control elements.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "palindromic sequence" refers to a nucleic acid sequence (DNA or RNA) that is the same whether read 5' (five-prime) to 3' (three prime) on one strand or 5' to 3' on the complementary strand-nucleotide sequence is said to be a palindrome if it is equal to its reverse complement. A palindromic nucleotide sequence can form a hairpin. The term is intended to include sequences where substantially complementarities exists but may include a few mismatched pairs, e.g., that do not disrupt self-hybridization, or form multiple loops.

Restriction sites, or restriction recognition sites, are locations on a nucleic acid molecule containing specific sequences of nucleotides, which are cut by restriction enzymes (nucleases) or other capable molecule. Within any of the embodiments disclosed herein, the restriction site may be referred to as a cleavage site. The sites are typically palindromic sequences, and a particular cleaving molecule, e.g., restriction enzyme, may cut the sequence between two nucleotides or more within its recognition site, or somewhere nearby. Naturally occurring restriction enzymes typically recognize sequences that are 4-6 bp long. These terms are synonymous with restriction enzyme consensus sequence. Non-naturally occurring cleaving enzymes and molecules are contemplated. Chu and Orgel report non-enzymatic sequence-specific cleavage of single-stranded DNA. See PNAS, 1985, 82:963-967. See also Dervan, Science, 1986, 232:464-47; Dreyer & Dervan PNSA, 1985, 82(4):968-972; and U.S. Pat. Nos. 6,555,692 and 4,795,700.

A "rare restriction site" refers to a site cut by a cleaving molecule or other restriction enzyme that is greater than 6, 7, or 8 bp long. Restriction-modification enzymes generate restriction endonucleases with longer recognition sites by mutating or engineering existing enzymes or producing chimeric restriction nucleases. Zinc finger proteins are often used in chimeric restriction enzymes with tailor-made sequence specificities. These proteins typically bind to the nucleic acids by inserting an alpha-helix into the major groove of the double helix. For example, one may design nucleases that will cut DNA at a preferred site by making fusions of zinc finger proteins to the cleavage domain of Fok I endonuclease. See Kim et al., *Proc. Natl. Acad. Sci. USA* 1996, 93, 1156-1160.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "primer" refers to an polynucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. The primer must be sufficiently long to prime the synthesis of extension products in the presence of the inducing agent. The exact lengths of the primers will depend on many factors, including temperature, source of primer and the use of the method.

The term "sequencing" refers to any number of methods that may be used to identify the order of nucleotides a particular nucleic acid. Methods and instrumentation for nucleic acid sequencing are known, and, in certain embodiments, the sequencing methods are not limited to the specific method, devices, or data/quality filtering utilized. Bokulich et al. report quality-filtering improves sequencing produced by Illumina GAIIx, HiSeq and MiSeq instruments. See Nature Methods, 2013, 10:57-59.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture. This process for amplifying the target sequence consists of introducing a large excess of two polynucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any polynucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, primers, nucleic acid template, and the amplification enzyme etc.) needed for amplification. Typically, amplification reagents along with other reaction components are placed and contained in a reaction vessel (test tube, microwell, etc.).

Within certain embodiments, methods disclosed herein are used in combination with paired-end, mate-pair methods described further below and described in Bentley et al., Nature, 2008, 456, 53-59 and Meyer et al., Nature protocols, 2008, 3, 267-278, hereby incorporated by reference.

Certain methods utilize fluorescently labeled nucleotides attached to a growing double stranded sequence wherein the polymerization is controlled with chemical functional groups. Areas of a solid surface are enhanced with the same oligonucleotide and the fluorescently labeled nucleotide indicates which base is being added. The approach described may also be extended to other protocols, including full-sequencing of intermediate sized fragments (>300 bp).

In the pair-end method, nucleic acids are broken into segments/fragments typically of less than 800 bp (e.g., but not limited to, enzymatic fragmentation, sonication, hydroshear, nebulization). The (double stranded) fragments are end-polished, A-tailed, and ligated to a forked adaptor bearing single stranded extensions that cause PCR amplification to introduce different (A and B) double stranded extensions to opposite ends of each fragment. The end pieces generated through PCR contain functional sites for later use in library PCR, cluster synthesis, and primer directed end-sequencing. PCR products are generated with the end labels (A and B) in both orientations in respect to the positive and negative strands of each DNA fragment.

After amplification by PCR and gel purification, the double stranded, vectorially modified, blunt ended DNA fragments are denatured into single strands. These are annealed to a lawn of covalently attached, single stranded oligonucleotides (complementary to the 3' ends extensions B or A) on the surface tile of a capture chamber (flow cell).

The capture oligonucleotides prime synthesis of a strand complementary to the annealed single stranded DNA, after which the product is denatured and the (non-covalent) template is washed away. The retained strand then anneals to a nearby capture oligonucleotide complementary to its free 3' end. A second strand is extended from this capture oligonucleotide, generating a double stranded "bridge", tethered at either end only by the 5' ends of the DNA duplex.

These bridges are denatured and the single strands are reannealed to new capture oligonucleotides and the process is repeated until amplification creates, for each DNA fragment originally annealed to the chamber surface, a cluster of oligonucleotides attached to the surface by either their A or B ends. This typically generates a large-number of clusters per flow cell.

Sequencing is typically conducted in two phases. In phase I, the population of DNA bridges is cleaved with a reagent specific to one of the two linkers, and non-covalently linked strands are denatured and washed away. This leaves single stranded DNAs in only one of the two orientations (e.g., B covalent 5' end) to be sequenced from the free end, employing the A sequencing primer introduced with the forked adapter.

Sequencing is performed by priming with the A oligonucleotide the successive incorporation the appropriate base from a solution of four distinguishable fluorescent nucleotide triphosphate derivatives; following optical recording of each newly added base, the fluorophore is hydrolyzed and the reaction repeated. In this way up to 150, 250, or more bases of the free end may be recorded optically.

Following phase I, the untethered strands generated during sequencing are denatured and washed away. The retained template is then re-annealed at its free 3' end to a capture oligonucleotide on the tile (e.g., A). A new strand of opposite orientation is synthesized by extending the capture oligonucleotide. The resultant population of bridged oligonucleotides is then cleaved at the second (e.g., B) linker, and the resulting untethered strands are denatured and washed away, as illustrated. The remaining population presents a free 3' ('B') end, sequenced as before, priming with 'B' oligonucleotide to yield the complementary sequence of the opposite end of the first sequenced strand. These read pairs are reported together for each cluster.

In mate-pair sequencing nucleic acids are fragmented, (e.g., but not limited to, by enzymatic fragmentation, sonication or hydroshear) into segments, typically several kb. These random fragments are end polished, biotinylated at their ends and circularized by enzymatic ligation; residual linear products are removed with exonucleases I and II.

Circularization joins together the two biotinylated ends of the shear fragments. The circular nucleic acid is broken randomly into shorter linear fragments, typically of 300-500 bp in length. The short fragments bearing the biotin are adsorbed to streptavidin beads and the unbiotinylated fragments are washed away and discarded. The retained fragments are end-polished, A-tailed, ligated to forked adapters (as described above) and size selected by gel purification. The resulting fragments constitute a library of pairs of randomly distributed sequence elements where each element or pair is separated from the other by a known average distance (the first shear length) on the nucleic acid. This mate-pair library is sequenced according to the protocol outlined in the previous section.

Example 1: Sequencing of mRNA with Tagging Reagents

Cells or tissue are derived poly-A mRNA isolated with a standard kit and removing remnants of genomic DNA is typical (DNA-Free™, LifeTechnology).

1. cDNA reverse is transcribed from RNA (Murine Maloney Leukemia Virus RTase) primed with tagging reagents containing SMID; RNAse H treatment of the heteroduplex. Murine Maloney Leukemia Virus RTase may be replaced with other viral reverse transcriptases, or any comparable enzymes of other origins capable of reverse transcription of RNA.

2. Labeled single stranded cDNA is circularized (T4 RNA, DNA Ligase (CircLigase; Epicentre)); removal of residual linear cDNAs with exonuclease I.

3. Circularized cDNA suspension is aliquoted and expanded with Rolling Circle Amplification (RCA) (phi 29 DNA polymerase) [cDNA population to be amplified can be varied with choice of primers.]

4. Hyperbranched RCA cDNA homopolymers are optionally debranched with S-1 nuclease or Mung Bean nuclease; transferred for enzymatic fragmentation or sonication buffer and fragmented (e.g. enzymatic fragmentation, sonication, hydroshear) to pre-selected average size ([e.g., 2-4 kb]).

5. Fragments are cleaved with restriction enzyme(s); buffer exchange. This material is submitted to a commercial Genome Center for library preparation and sequencing by standard methods. A primer/tagged specific modified PCR primer can be supplied to replace the A primer of the standard kit.

Example 2: Non-Polyadenylate RNAs

Salzman, J. et al. report circular RNAs Are the Predominant Transcript Isoform from Hundreds of Human Genes in Diverse Cell Types. PloS One, 2012, vol 7, issue 2, e30733. These are not polyadenylated. This class of RNA products is amenable to sequencing with this technology using tagging reagents, at low stoichiometry, bearing random 3' terminal sequences to make a copy of the RNAs, followed by circularization and processing as described herein.

The invention claimed is:

1. A method comprising:
   a) providing double stranded nucleic acid fragments comprising a tagging part and a target part, wherein the tagging part comprises a segment of overlapping sequences and a segment of varying sequences, wherein the overlapping sequences comprise a first primer site and a restriction site;
   b) mixing the double stranded fragments with a restriction enzyme to the restriction site providing cleaved fragments;
   c) mixing the cleaved fragments with an enzyme under conditions such that the cleaved fragments form circular fragments;
   d) breaking the circular fragments at random points providing sheared fragments;
   e) ligating an adaptor to the ends of the double stranded nucleic acids wherein the adaptor comprises a second primer site providing an adaptor nucleic acid conjugate;
   f) amplifying the adaptor nucleic acid conjugates with primers to the first and second primer sites, wherein the first primer comprises a first capture sequence on the 5' end and the second primer comprises a second capture sequence on the 5' end to provide a capture target tagged conjugate; and
   g) sequencing the capture target tag conjugate.

2. The method of claim 1, wherein the segment of varying sequences is between the first primer site and the target part.

3. The method of claim 1, wherein the first primer site is between the segment of varying sequences and the target part.

4. The method of claim 1, wherein the restriction site is between the segment of varying sequences and the first primer site.

5. The method of claim 1, wherein the segment of varying sequences is between the restriction site and the first primer site.

6. The method of claim 1, wherein the nucleic acid fragments comprises two segments of varying sequences wherein the varying segments are identical sequences and the restriction site is between the identical sequences.

7. A method comprising
 a) mixing a sample and a group of tagging polynucleotides, wherein the sample comprises a mixture of nucleic acids of different length and/or different sequence, wherein the tagging polynucleotides individually comprise overlapping sequences and a part with random sequences and wherein the tagging polynucleotides comprise a palindromic sequence configured to self-hybridize into a double stranded segment wherein the double stranded segment comprises a restriction site, wherein the part with random sequences is within the double stranded segment, and wherein the mixing is done under conditions such that the tagging polynucleotides bind the nucleic acids to form nucleic acids individually tagged with random sequences;
 b) replicating the nucleic acid mixture individually tagged with random sequences into a mixture of homopolymers, wherein the homopolymers comprise a repeating nucleic acid and a repeating sequence tag;
 c) mixing the homopolymer fragments with a restriction nuclease that cleaves a site correlated to the overlapping sequences on the tagging polynucleotides providing cleaved homopolymer fragments; and
 d) sequencing the cleaved homopolymer fragments.

\* \* \* \* \*

UNITED STATES PATENT AND TRADEMARK OFFICE
CERTIFICATE OF CORRECTION

PATENT NO. : 10,227,584 B2
APPLICATION NO. : 14/768749
DATED : March 12, 2019
INVENTOR(S) : Emerick et al.

It is certified that error appears in the above-identified patent and that said Letters Patent is hereby corrected as shown below:

In the Specification

Column 1, Lines 8-9:
"This is the U.S. National Stage of International Application No. PCT/US2014/016673, filed Feb. 17, 2015, which",
Should read:
-- This is the U.S. National Stage of International Application No. PCT/US2014/016673, filed Feb. 17, 2014, which --.

Signed and Sealed this
Nineteenth Day of April, 2022

Katherine Kelly Vidal
*Director of the United States Patent and Trademark Office*